US005622852A

United States Patent [19]

Korsmeyer

[11] Patent Number: 5,622,852

[45] Date of Patent: Apr. 22, 1997

[54] BCL-X/BCL-2 ASSOCIATED CELL DEATH REGULATOR

[75] Inventor: Stanley J. Korsmeyer, Clayton, Mo.

[73] Assignee: Washington University, St. Louis, Mo.

[21] Appl. No.: 333,565

[22] Filed: Oct. 31, 1994

[51] Int. Cl.$^6$ .............................. C12N 1/15; C12N 1/21; C12N 5/10; C12N 15/12; C07H 21/00

[52] U.S. Cl. ................ 435/325; 435/252.3; 435/252.33; 435/254.11; 435/348; 536/23.4; 536/23.5; 536/24.31; 536/24.33; 935/8; 935/11; 935/66

[58] Field of Search ................................ 536/23.4, 23.5, 536/24.31, 24.33; 435/252.3, 252.33, 240.1, 254.11; 935/66, 8, 11

[56] References Cited

PUBLICATIONS

Boise et al., "bcl–x, a bcl–2–Related Gene That Functions as a Dominant Regulator of Apoptotic Cell Death", *Cell*, 74:597–608 (1993).

Hengartner et al., "*Caenorhabditis elegans* gene ced–9 protects cells from programmed cell death", *Nature*, 356:494–499 (1992).

Hengartner et al., "*C. elegans* Cell Survival Gene ced–9 Encodes a Functional Homolog of the Mammalian Proto–Oncogene bcl–2", *Cell*, 76:665–676 (1994).

Oltvai et al., "Bcl–2 Heterodimerizes In Vivo with a Conserved Homolog, Bax, That Accelerates Programed Cell Death", *Cell*, 74:609–619 (1993).

Vaux et al., "Prevention of Programmed Cell Death in *Caenorhabditis elegans* by Human bcl–2" *Science*, 258:1955–1957 (1992).

Williams et al., "Molecular Regulation of Apoptosis: Genetic Controls on Cell Death", *Cell*, 74:777–779 (1993).

Nuñez et al. (1994) The Bcl–2 family of proteins:regulators of cell death and survival. Trends in Cell Biology 4: 399–403.

Yin et al. (1994) BH1 and BH2 domains of Bcl–2 are required for inhibition of apoptosis and heterodimerization with Bax. Nature 369: 321–323.

Sato et al. (1994) Interactions among members of the Bcl–2 protein family analyzed with a yeast two–hybrid system. Proc. Natl. Acad. Sci., USA, 91: 9238–9242.

Borner et al. (1994) Dissection of functional domains in Bcl–2α by site–directed mutagenesis. Biochemistry and Cell Biology 72: 463–469.

*Primary Examiner*—Charles L. Patterson, Jr.
*Assistant Examiner*—G. E. Bugaisky
*Attorney, Agent, or Firm*—Tracy J. Dunn

[57] ABSTRACT

The invention provides a bcl-2 related protein, Bad, Bad muteins, two-hybrid systems comprising interacting Bad polypeptide sequences, Bad polynucleotides, and uses thereof.

9 Claims, 15 Drawing Sheets

Mouse Polynucleotide Sequence Encoding *Bad* Polypeptide

SEQ ID NO: 3

5'-ATGGGAACCCCAAAGCAGCCCTCGCTGGCTCCTGCACACGCCCTAGGCTTGAGGAAGTCC
GATCCCGGAATCCGGAGCCTGGGGAGCGACGCGGGAGGAAGGCGGTGGAGACCAGCAGCCCAG
AGTATGTTCCAGATCCCAGAGTTTGAGCCGAGTGAGCAGGAAGACGCTAGTGCTACAGATAGG
GGCCTGGGCCCTAGCCTCACTGAGGACCAGCCAGGTCCCTACCTGGCCCCAGGTCTCCTGGGG
AGCAACATTCATCAGCAGGGACGGGCAGCCACCAACAGTCATCATGGAGGCGCAGGGGCTATG
GAGACTCGGAGTCGCCACAGTTCGTACCCAGCGGGGACCGAGGAGGATGAAGGGATGGAGGAG
GAGCTTAGCCCTTTTCGAGGACGCTCGCGTTCGGCTCCCCCCAATCTCTGGGCAGCGCAGCGC
TACGGCCGTGAGCTCCGAAGGATGAGCGATGAGTTTGAGGGTTCCTTCAAGGGACTTCCTCGC
CCAAAGAGCGCAGGCACTGCAACACAGATGCGACAAAGCGCCGGCTGGACGCGCATTATCCAG
TCCTGGTGGGATCGAAACTTGGGCAAAGGAGGCTCCACCCCCTCCCAGTGA-3'

```
GGCACGAGCGGACCCCGCCCCCTAGCTTGTGTCTGCAGGCCCCGCGTCCGGCCCGGGGCA
GCGTACGCACACCTATCCTGGCAGCAGAGGCCCCTGGAGCCCCACGGCTCGCCTTCCTGG
GCGCCCCGTCCCTTCTTCCGCACCCGGGCGGCCATCCTGCCGTAAAGGAGCTCCCGAAAT
GGCGCGGGGGGTTGTCCCCAAGACGGGCAGTGCAAGGCCCTCCACGATCGGGAAGAAGGA
GCTGGTCTTCCCATCCCGGTCACTCGGTCCAGGGGGAGCAATAACCATCGCAACGACCAT
TGCATCCGACGGCCGAGCTTCAGTGAACGGCTCTATAAGTAATCACTAAGCTGTTTACAG
AGTTTTCACCAGCTCCCCAGGGAGGTGTCATTAACCCCATTTTACAGGAGGGAATTCGGG
                                                        +1
    CCCAGAAGGGCTGGAGGACTTATCAGCCGAAGCAGGCCTCCAGGATCCAAATGGGAACCC  10
                                                         M  G  T

    CAAAGCAGCCCTCGCTGGCTCCTGCACACGCCCTAGGCTTGAGGAAGTCCGATCCCGGAA  70
  4 P  K  Q  P  S  L  A  P  A  H  A  L  G  L  R  K  S  D  P  G

    TCCGGAGCCTGGGGAGCGACGCGGGAGGAAGGCGGTGGAGACCAGCAGCCCAGAGTATGT 130
 24 I  R  S  L  G  S  D  A  G  G  R  R  W  R  P  A  A  Q  S  M

    TCCAGATCCCAGAGTTTGAGCCGAGTGAGCAGGAAGACGCTAGTGCTACAGATAGGGGCC 190
 44 F  Q  I  P  E  F  E  P  S  E  Q  E  D  A  S  A  T  D  R  G

    TGGGCCCTAGCCTCACTGAGGACCAGCCAGGTCCCTACCTGGCCCCAGGTCTCCTGGGGA 250
 64 L  G  P  S  L  T  E  D  Q  P  G  P  Y  L  A  P  G  L  L  G

    GCAACATTCATCAGCAGGGACGGGCAGCCACCAACAGTCATCATGGAGGCGCAGGGGCTA 310
 84 S  N  I  H  Q  Q  G  R  A  A  T  N  S  H  H  G  G  A  G  A

    TGGAGACTCGGAGTCGCCACAGTTCGTACCCAGCGGGGACCGAGGAGGATGAAGGGATGG 370
104 M  E  T  R  S  R  H  S  S  Y  P  A  G  T  E  E  D  E  G  M

    AGGAGGAGCTTAGCCCTTTTCGAGGACGCTCGCGTTCGGCTCCCCCCAATCTCTGGGCAG 430
124 E  E  E  L  S  P  F  R  G  R  S  R  S  A  P  P  N  L  W  A

    CGCAGCGCTACGGCCGTGAGCTCCGAAGGATGAGCGATGAGTTTGAGGGTTCCTTCAAGG 490
144 A  Q  R  Y  G  R  E  L  R  R  M  S  D  E  F  E  G  S  F  K

    GACTTCCTCGCCCAAAGAGCGCAGGCACTGCAACACAGATGCGACAAAGCGCCGGCTGGA 550
164 G  L  P  R  P  K  S  A  G  T  A  T  Q  M  R  Q  S  A  G  W

    CGCGCATTATCCAGTCCTGGTGGGATCGAAACTTGGGCAAAGGAGGCTCCACCCCCTCCC 610
184 T  R  I  I  Q  S  W  W  D  R  N  L  G  K  G  G  S  T  P  S

    AGTGATCTTCTGCTCCACATCCCGGAACTCTACCCGCTCCCGTCGCCCGCCATATTGGGT
204 Q  -
    GTGGGCGGAAGTCTTTCGAGGCCTTAGGAAAAAAAAAGAGGATCGCTGTGTCCCTTTAAC
    AGGGAGAAGAGCTGACGTACAGCTTGAGTCCCTTCCGGTGCGTGCAATAGCCACGGAGGG
    GTGGCTCCTGTTTGGAGTTTCAAAGTTTTCCACGCACCCCACCCCCTAAGCCTCCGGAAG
    TGGCTGTTTTCCCTCTCCTGTTCTGGACTGCCCTCGGGTGCCTGTGCTAAGTTGGGGGTC
    TGGGTGCTGTCCTGTCATAACTGGGGACCCGAGGTCGCGAGAAACGTGCTTTATAATAAA
    GCCTGCGCATGTGCAAAAAAAAAAAAAAAAAA
```

FIGURE 1

*Bad* Sequences

Figure 2a

Mouse *Bad* Polypeptide Deduced from cDNA

SEQ ID NO: 2

MGTPKQPSLAPAHALGLRKSDPGIRSLGSDAGGRRWRPAAQSMFQIPEFEPSEQEDASATD
RGLGPSLTEDQPGPYLAPGLLGSNIHQQGRAATNSHHGGAGAMETRSRHSSYPAGTEEDEG
MEEELSPFRGRSRSAPPNLWAAQRYGRELRRMSDEFEGSFKGLPRPKSAGTATQMRQSAGW
TRIIQSWWDRNLGKGGSTPSQ

Figure 2b

Mouse Polynucleotide Sequence Encoding *Bad* Polypeptide

SEQ ID NO: 3

5'-ATGGGAACCCCAAAGCAGCCCTCGCTGGCTCCTGCACACGCCCTAGGCTTGAGGAAGTCC
GATCCCGGAATCCGGAGCCTGGGGAGCGACGCGGGAGGAAGGCGGTGGAGACCAGCAGCCCAG
AGTATGTTCCAGATCCCAGAGTTTGAGCCGAGTGAGCAGGAAGACGCTAGTGCTACAGATAGG
GGCCTGGGCCCTAGCCTCACTGAGGACCAGCCAGGTCCCTACCTGGCCCCAGGTCTCCTGGGG
AGCAACATTCATCAGCAGGGACGGGCAGCCACCAACAGTCATCATGGAGGCGCAGGGGCTATG
GAGACTCGGAGTCGCCACAGTTCGTACCCAGCGGGGACCGAGGAGGATGAAGGGATGGAGGAG
GAGCTTAGCCCTTTTCGAGGACGCTCGCGTTCGGCTCCCCCCAATCTCTGGGCAGCGCAGCGC
TACGGCCGTGAGCTCCGAAGGATGAGCGATGAGTTTGAGGGTTCCTTCAAGGGACTTCCTCGC
CCAAAGAGCGCAGGCACTGCAACACAGATGCGACAAAGCGCCGGCTGGACGCGCATTATCCAG
TCCTGGTGGGATCGAAACTTGGGCAAAGGAGGCTCCACCCCCTCCCAGTGA-3'

Figure 3a Yeast Two-Hybrid System
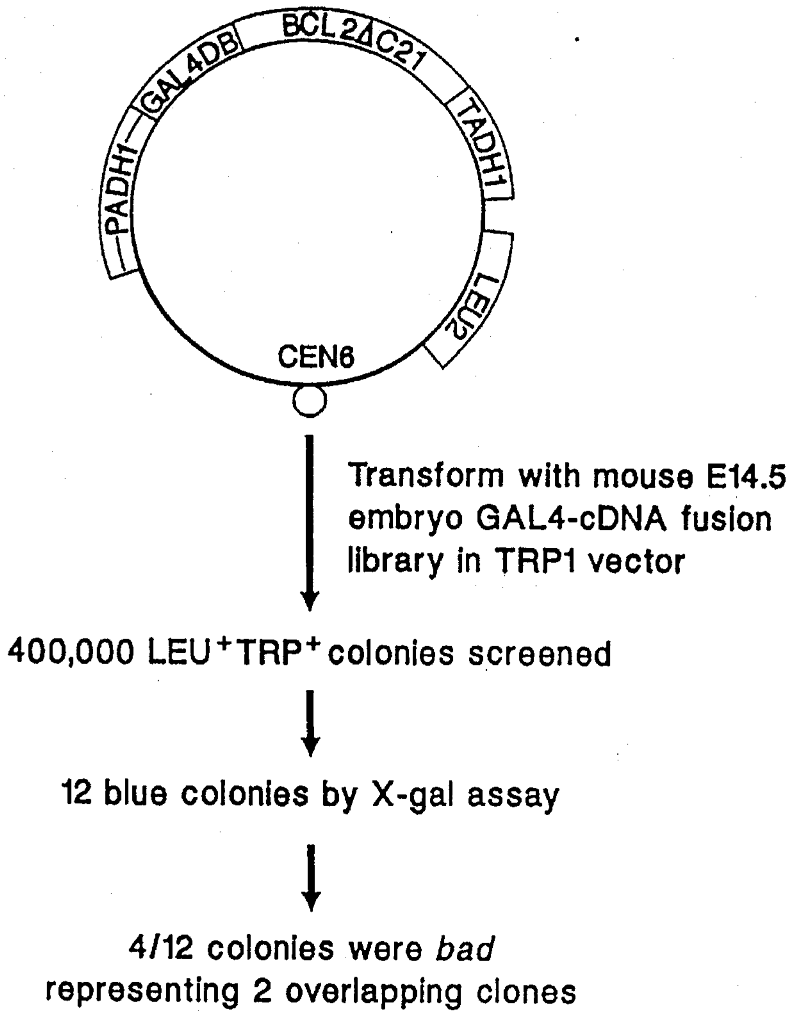
Figure 3b Expression Cloning
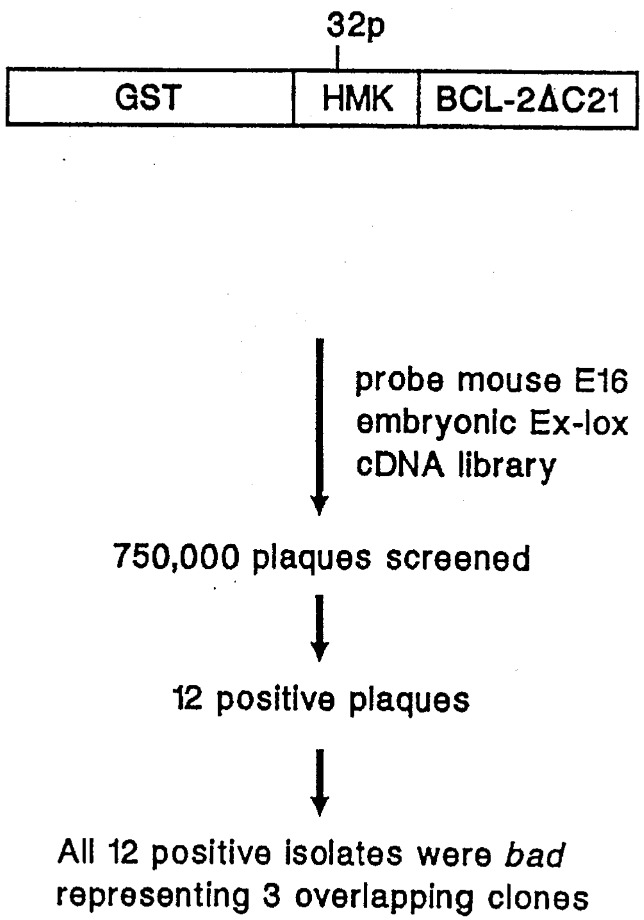

Figure 4a Yeast Two-Hybrid Isolates
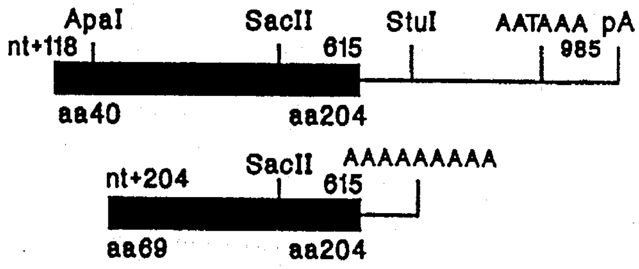
Figure 4b Expression Cloning Isolates
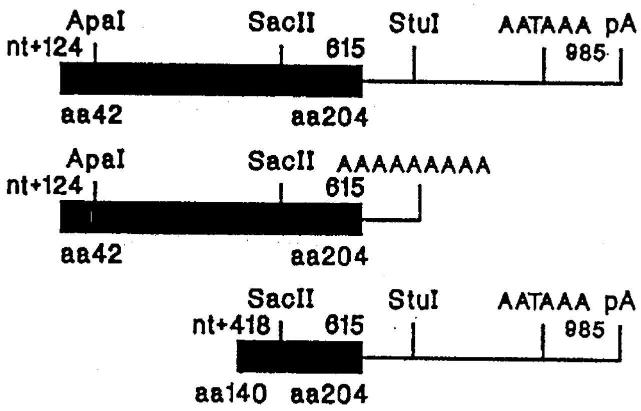
Figure 4c **Murine *bad* cDNA**
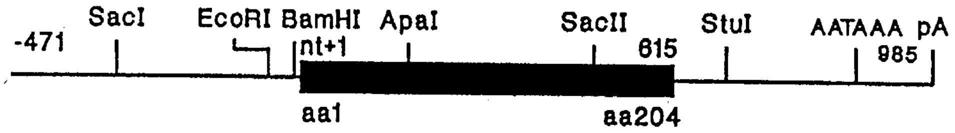

Figure 5a

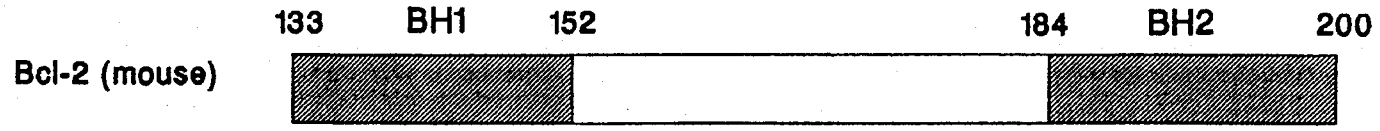

| | | | |
|---|---|---|---|
| Bcl-2 (mouse) | 133 | E F F R D G V - N W G R I V A F F E - - F G G | 152 |
| Bax (mouse) | 98 | D M F A D G N F N W G R V V A L F Y - - F A S | 118 |
| Bcl-$x_L$ (mouse) | 129 | E L F R D G V - N W G R I V A F F S - - F G G | 148 |
| A1 (mouse) | 77 | K E F E D G I I N W G R I V T I F A - - F G G | 97 |
| Mcl-1 (mouse) | 233 | H V F K D G V T N W G R I V T L I S - - F G A | 253 |
| Ced-9 (C. elegans) | 159 | A Q T D Q C P M S Y G R L I G L I S - - F G G | 179 |
| Bad (mouse) | 137 | P P N L W A A Q R Y G R E L R R M S D E F E G | 160 |

| | | | |
|---|---|---|---|
| Bcl-2 (mouse) | 184 | T W I Q D N - G G W D A F V E L Y G | 200 |
| Bax (mouse) | 150 | V W I Q D Q - G G W E G L L S Y F G | 166 |
| Bcl-$x_L$ (mouse) | 180 | P W I Q E N - G G W D T F V D L Y G | 191 |
| A1 (mouse) | 132 | E W I R Q N - G G W E D G F I K K F | 148 |
| Mcl-1 (mouse) | 285 | D W L V K Q R - G W D G F V E F F H | 301 |
| Ced-9 (C.elegans) | 213 | N W K E H N R S - W D D F M T L G K | 229 |
| Bad (mouse) | 182 | G W T R I I Q S W W D R N - - L G K | 197 |

| DNA BINDING DOMAIN | ACTIVATION DOMAIN | ONPG | X-GAL |
|---|---|---|---|
| pAS BAD | pACTII | 1.0 | |
| | pACTII BCL-2 | 98 | ● |
| | pACTII BAX | 0.6 | |
| | pACTII BCL-$X_L$ | 37 | ◍ |
| | pACTII BCL-$X_S$ | 0.7 | |
| | pACTII MCL-1 | 1.2 | |
| | pACTII A1 | 1.1 | |
| | pACTII BAD | 1.1 | |
| pAS BCL-2 | pACTII | 1.0 | |
| | pACTII BAD | 122 | ◍ |
| pAS BCL-$X_L$ | pACTII | 1.0 | |
| | pACTII BAD | 68 | ○ |
| pAS MCL-1 | pACTII | 1.0 | |
| | pACTII BAD | 0.8 | |

*FIG. 9.*

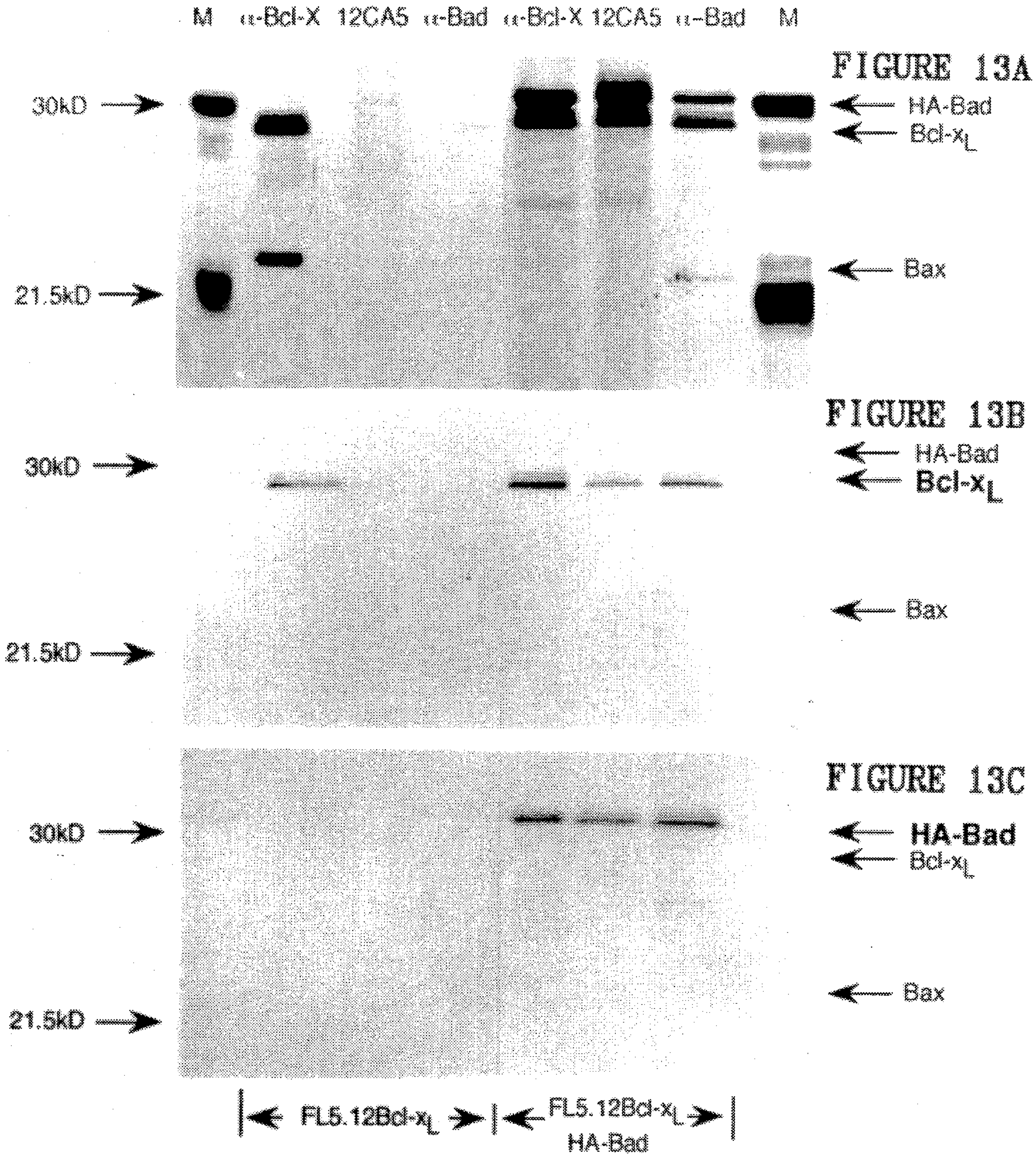
FIGURE 13A
FIGURE 13B
FIGURE 13C
FIGURE 13D
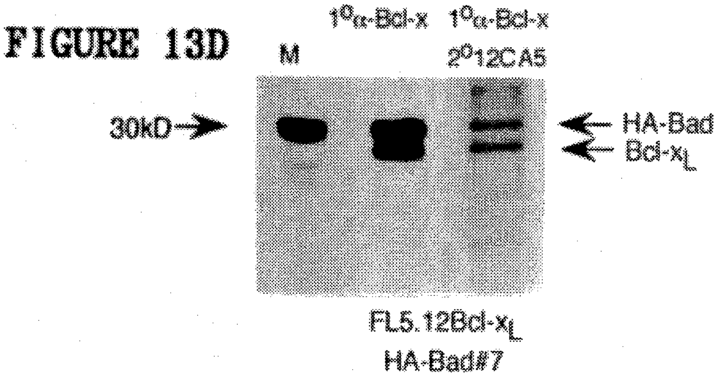

IP with anti-Bcl-x or 6C8

IP with 4D2
(on supernatants from A)

IP with 4D2 fraction of Bax not heterodimerized   0.97   0.52   0.81   0.53   0.39   0.47

BCL-X/BCL-2 ASSOCIATED CELL DEATH REGULATOR

STATEMENTS OF RIGHTS

The U.S. Government has a paid-up license in this invention and the right in limited circumstances to require the patent owner to license others on reasonable terms as provided for by the terms of Grant No. 49712-05 issued by the National Institute of Health.

FIELD OF THE INVENTION

The invention relates to the identification, purification, and isolation of a novel protein, termed Bad, which interacts with bcl-2 and bcl-x proteins and regulates cell death, polynucleotides encoding Bad polypeptides, polynucleotides which specifically hybridize to a naturally-occurring mammalian Bad gene or mRNA sequence, oligonucleotide primers for amplifying a naturally-occurring mammalian Bad gene or mRNA sequence, substantially purified Bad polypeptides and polynucleotides, methods and compositions for detecting Bad polypeptides and polynucleotides, methods and compositions for identifying agents which modulate cell death, and methods of treating or preventing disease by modulating cell death.

BACKGROUND OF THE INVENTION

Cell death is an important aspect during the embryonic or post-natal development of major organ systems. Apoptosis, or programmed cell death, also plays a critical role in maintaining homeostasis in many adult tissues. Apoptosis is a term used to refer to the process(es) of programmed cell death and has been described in several cell types (Waring et al. (1991) *Med. Res. Rev.* 11: 219; Williams G. T. (1991) Cell 65: 1097; Williams G. T. (1992) *Trends Cell Biol.* 2: 263; Yonisch-Rouach et al. (1991) *Nature* 352: 345). Apoptosis is likely involved in controlling the amount and distribution of certain differentiated cell types, such as lymphocytes and other cells of the hematopoietic lineage as well as other somatic and germ cells. The mechanism(s) by which apoptosis is produced in cells is incompletely understood, as are the regulatory pathways by which the induction of apoptosis occurs.

Apoptosis Mechanism(s)

Apoptosis was first described as a morphologic pattern of cell death characterized by cell shrinkage, membrane blebbing and chromatin condensation culminating in cell fragmentation (Kerr et al., 1972). One hallmark pattern early in the process of cell death is internucleosomal DNA cleavage (Wyllie, 1980). The death-sparing effects of interrupting RNA and protein synthesis and the stereotyped patterns of cell death during development were consistent with a cell autonomous genetic program for cell death (Wyllie et al. (1980) *Int. Rev. Cytol.* 68: 251; Sulston, J. and Horvitz, H. (1977) *Develop. Biol.* 56: 110; Abrams et al. (1993) *Development* 117: 29). The isolation of mutants defective for developmental cell death in the nematode *Caenorhabditis elegans* supported this view (Ellis, H. and Horvitz, H. (1986) *Cell* 44: 817; Hengartner et al. (1992) *Nature* 356: 494). Despite the identification of genes necessary for cell death and the ability to regulate apoptosis by known genes, the essential biochemical events in apoptotic death remain largely unknown.

The consistency of the morphologic and biochemical patterns defined as apoptosis within different cell types and species, during normal development and as a response to external stimuli are consistent with a common cause of cellular mortality. This thesis is supported by the concept of an endogenous program responsible for cell death and the presence of gene products which are positive and negative regulators of apoptosis. The best studied negative regulator of apoptosis is the bcl-2 proto-oncogene product. it provides the strongest evidence for a shared mammalian pathway of death by its ability to block a wide variety of cell death models.

The bcl-2 proto-oncogene is rather unique among cellular genes in its ability to block apoptotic deaths in multiple contexts (Korsmeyer, S. (1992) *Blood* 80: 879). Overexpression of bcl-2 in transgenic models leads to accumulation of cells due to evasion of normal cell death mechanisms (McDonnell et al. (1989) *Cell* 57: 79). Induction of apoptosis by diverse stimuli, such as radiation, hyperthermia, growth factor withdrawal, glucocorticoids and multiple classes of chemotherapeutic agents is inhibited by bcl-2 in in vitro models (Vaux et al. (1988) *Nature* 335: 440; Tsujimoto, Y. (1989) *Oncogene* 4: 1331; Nunez et al. (1990) *J. Immunol.* 144: 3602; Hockenbery et al. (1990) *Nature* 348: 334; Sentman et al. (1991) *Cell* 67: 879; Walton et al. (1993) *Cancer Res.* 53: 1853; Miyashita, T. and Reed, J. (1993) *Blood* 81: 151). These effects are proportional to the level of bcl-2 expression. Additionally, the endogenous pattern of bcl-2 expression is indicative of a role in the regulation of cell survival in vivo (Hockenbery et al. (1991) *Proc. Natl. Acad. Sci. USA* 88: 6961; LeBrun et al. (1993) *Am. J. Pathol.* 142: 743). The bcl-2 protein seems likely to function as an antagonist of a central mechanism operative in cell death.

bcl-2

The protein encoded by the bcl-2 proto-oncogene has been reported to be capable of inhibiting apoptosis in many hematopoietic cell systems. The proto-oncogene bcl-2 was isolated and characterized as a result of its frequent translocation adjacent to the immunoglobulin heavy chain enhancer in the t(14;18) chromosome translocation present in more than 80% of human follicular lymphomas (Chen-Levy et al. (1989) *Mol. Cell. Biol.* 9: 701; Cleary et al. (1986) *Cell* 47: 19). These neoplasias are characterized by an accumulation of mature resting B cells presumed to result from a block of apoptosis which would normally cause turnover of these cells. Transgenic mice expressing bcl-2 under the control of the Eμ enhancer similarly develop follicular lymphomas which have a high incidence of developing into malignant lymphomas (Hockenberry et al. (1990) *Nature* 348: 334; McDonnell T. J. and Korsmeyer S. J. (1991) *Nature* 349: 254; Strasser et al. (1991) *Cell* 67: 889; McDonnell et al. (1989) *Cell* 57: 79).

The bcl-2 protein is a 26 kD membrane-associated cytoplasmic protein (Tsujimoto et al. (1987) *Oncogene* 2: 3; U.S Pat. Nos. 5,202,429 and 5,015,568; Chen-Levy (1989) op.cit; Hockenberry (1990) op.cit; Hockenbery et al. (1991) *Proc. Natl. Acad. Sci.* (*USA*) 88: 6961; Monaghan et al. (1992) *J. Histochem. Cytochem.* 40: 1819; Nguyen et al. (1993) *J. Biol. Chem.* 268: 25265; Nguyen et al. (1994) *J. Biol. Chem.* 269: 16521). Unlike many other proto-oncogene products, the bcl-2 protein apparently functions, at least in part, by enhancing the survival of hematopoietic cells of T and B origins rather than by directly promoting proliferation of these cell types (Vaux et al. (1988) *Nature* 335: 440; Tsujimoto Y (1989) *Proc. Natl. Acad. Sci.* (*U.S.A.*)

86: 1958; Tsujimoto Y (1989) *Oncogene* 4: 1331; Reed et al. (1989) *Oncogene* 4: 1123; Nunez et al. (1989) *Proc. Natl. Acad. Sci.* (*U.S.A.*) 86: 4589; Nunez et al. (1990) *J. Immunol.* 144: 3602; Reed et al. (1990) *Proc. Natl. Acad. Sci.* (*U.S.A.*) 87: 3660; Alnemri et al. (1992) *Proc. Natl. Acad. Sci.* (*U.S.A.*) 89: 7295). The capacity of bcl-2 to enhance cell survival is related to its ability to inhibit apoptosis initiated by several factors, such as cytokine deprivation, radiation exposure, glucocorticoid treatment, and administration of anti-CD-3 antibody (Nunez et al. (1990) op.cit; Hockenbery et al. (1990) op.cit; Vaux et al. (1988) op.cit; Alnemri et al. (1992) *Cancer Res.* 52: 491; Sentman et al. (1991) *Cell* 67: 879; Strasser et al. (1991) op.cit). Upregulation of bcl-2 expression also inhibits apoptosis of EBV-infected B-cell lines (Henderson et al. (1991) *Cell* 65: 1107). The expression of bcl-2 has also been shown to block apoptosis resulting from expression of the positive cell growth regulatory proto-oncogene, c-myc, in the absence of serum or growth factors (Wagner et al (1993) *Mol. Cell. Biol.* 13: 2432).

Within vertebrates, bcl-2 is the best understood gene in a cell death pathway and functions as a cell death repressor. Other proteins which interact with and/or are structurally related to the bcl-2 gene product have also been identified, such as for example bcl-$x^L$ and bcl-$x^S$ (Boise et al. (1993) *Cell* 74: 597; Gonzalez-Garcia et al. (1994) *Development* 120: 3033; Gottschalk et al. (1994) *Proc. Natl. Acad. Sci.* (*USA*) 91: 7350), Bax (Oltvai et al. (1993) *Cell* 74: 609), Mcl-1 (Kozopas et al. (1993) *Proc. Natl. Acad. Sci.* (*USA*) 90: 3516), and A1 (Lin et al. (1993) *J. Immunol.* 151: 179). The family of bcl-2-related proteins also includes the nematode protein ced-9 (Vaux et al. (1992) *Science* 258: 1955; Hengartner et al. (1992) *Nature* 356: 494; Hengartner M. O. and Horvitz H. R. (1994) *Cell* 76: 665) and two DNA virus proteins, LMW5-HL and BHRF-1 of the Epstein Barr Virus. Thus, a family of bcl-2-like genes exists and evidence indicates that they participate in regulating cell death.

The family of bcl-2-related proteins has been noted to have homology that is principally, but not exclusively, clustered within two conserved regions entitled bcl-homology 1 and 2 (BH-1 and BH2) (Williams G. T. and Smith C. A. (1993) *Cell* 74: 777; Yin et al. (1994) op.cit). This includes Bax, bcl-$X_L$, Mcl-1, and A1, and several open reading frames in DNA viruses including BHRF1 of Epstein-Barr virus and LMW5-HL of African swine fever virus (Oltvai et al. (1993) op.cit; Boise et al. (1993) op.cit; Kozopas et al. (1993) op.cit; Lin et al. (1993) op.cit).

Bax

It has been discovered that bcl-2 also associates, in vivo with a 21 kD protein partner, called Bax (Oltvai et al. (1993) op. cit; Yin et al. (1994) *Nature* 369: 321). Bax shows extensive amino acid homology with bcl-2 and forms homodimers with itself and heterodimers with bcl-2 in vivo. Bax is encoded by 6 exons and demonstrates a complex pattern of alternative RNA splicing that predicts a 21 Kd membrane ($\alpha$) and two forms ($\beta$ and $\gamma$) of cytosolic protein. When Bax predominates and a substantial percentage of Bax is present as homomultimers (e.g., homodimers) and/or free (unbound) Bax monomer, programmed cell death is accelerated and the death repressor activity of bcl-2 is countered. When in excess, Bax counters the ability of bcl-2 to repress cell death. It was completely unexpected to find that Bax shared extensive homology with bcl-2, especially within two highly conserved domains. These domains are also the most highly conserved regions of human, mouse, and chicken bcl-2. These domains are also conserved in an open reading frame BHRF-1 within Epstein-Barr virus and Mcl-1, a gene recently isolated from a myeloid leukemia cell line following induction with phorbol ester (Kozopas et al. (1993) op.cit).

bcl-x

The bcl-x gene was identified by low-stringency hybridization using a bcl-2 polynucleotide probe (Boise et al. (1993) op.cit. and encodes two proteins, bcl-$x^L$ and bcl-$x^S$, via alternative RNA splicing. The bcl-$x^L$ cDNA encodes a polypeptide of 233 amino acids with similar domains to those of bcl-2. The bcl-$x^S$ cDNA encodes a polypeptide of 170 amino acids in which the region of highest homology to bcl-2 has been deleted. When the ability of these two proteins to regulate apoptotic cell death was compared, it was found that bcl-$x^L$ rendered cells resistant to apoptotic cell death induced by growth factor deprivation, whereas bcl-$x^S$ could prevent overexpression of bcl-2 from inducing resistance to apoptotic cell death. Thus, bcl-$x^L$ can serve as an inhibitor of apoptotic cell death in a variety of cell lines, whereas bcl-$x^S$ inhibits the ability of bcl-2 to inhibit cell death and can make cells more susceptible to apoptotic cell death.

Cell Proliferation Control and Neoplasia

Many pathological conditions result, at least in part, from aberrant control of cell proliferation, differentiation, and/or apoptosis. For example, neoplasia is characterized by a clonally derived cell population which has a diminished capacity for responding to normal cell proliferation control signals. Oncogenic transformation of cells leads to a number of changes in cellular metabolism, physiology, and morphology. One characteristic alteration of oncogenically transformed cells is a loss of responsiveness to constraints on cell proliferation and differentiation normally imposed by the appropriate expression of cell growth regulatory genes.

The precise molecular pathways and secondary changes leading to malignant transformation for many cell types are not clear. However, the characteristic translocation of the apoptosis-associated bcl-2 gene to the immunoglobulin heavy-chain locus t(14;18) in more than 80 percent of human follicular B cell lymphomas and 20 percent of diffuse lymphomas and the neoplastic follicular lymphoproliferation present in transgenic mice expressing high levels of bcl-2 indicates that the bcl-2 gene likely is causally involved in neoplastic diseases and other pathological conditions resulting from abnormal cell proliferation, differentiation, and/or apoptosis. Thus, it is desirable to identify agents which can modify the activity(ies) of bcl-2-related proteins so as to modulate cell proliferation, differentiation, and/or apoptosis for therapeutic or prophylactic benefit. Further, such agents can serve as commercial research reagents for control of cell proliferation, differentiation, and/or apoptosis in experimental applications, and/or for controlled proliferation and differentiation of predetermined hematopoietic stem cell populations in vitro, in ex vivo therapy, or in vivo.

Despite progress in developing a more defined model of the molecular mechanisms underlying the transformed phenotype and neoplasia, few significant therapeutic methods applicable to treating cancer beyond conventional chemotherapy have resulted. Such bcl-2-related protein modulating agents can provide novel chemotherapeutic agents for treatment of neoplasia, lymphoproliferative conditions, arthritis, inflammation, autoimmune diseases, and the like. The present invention fulfills these and other needs.

While identifying the bcl-2 cell death pathway is significant, a way of regulating the bcl-2 pathway has not been reported. The ability to down-regulate the cell death repressing effect of bcl-2 and/or up-regulate the cell death promoting activity of Bax would be advantageous in cancer therapy, in controlling hyperplasia such as benign prostatic hypertrophy (BPH) and eliminating self reactive clones in autoimmunity by favoring death effector molecules. Up-regulating the effect of bcl-2 and favoring death repressor molecules would be beneficial in the treatment and diagnosis of immunodeficiency diseases, including AIDS, senescence, neurodegenerative disease, ischemic cell death, wound-healing, and the like.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention relates to the unexpected discovery that bcl-2 interacts with other proteins and in particular with an associated 22.1 kD protein called Bad (bcl-xL/bcl-2 associated neath promoter). The deduced polypeptide sequence of the Bad cDNA is 204 amino acids in length and has homology to the bcl-2-related family clustered in the BH1 and BH2domains. It has been unexpectedly discovered that Bad heterodimerizes with bcl-$x^L$ and bcl-2 in yeast two-hybrid assays and in vivo in mammalian cells. It has also been discovered that overexpressed Bad counters the death inhibitory activity of bcl-$x^L$, but is much less effective at countering the death inhibitory activity of bcl-2. Bad expression can accelerate apoptotic cell death induced by cytokine deprivation in an IL-3 dependent cell line expressing bcl-$x^L$ and expressed Bad counters the death repressor activity of bcl-$x^L$. Bad competes with Bax for binding to bcl-$x^L$. By sequestering bcl-$x^L$ into Bad:bcl-$x^L$ heteromultimers, the expression of bcl-$x^L$ increases the ratio of Bax present as free (unbound) Bax monomers or Bax:Bax homomultimers as compared to heteromultimers containing Bax (e.g., Bax/bcl-$x^L$ heteromultimers), and thereby promotes susceptibility to apoptotic cell death. This discovery provides a model in which Bad can accelerate apoptotic cell death by reducing the relative amount of bcl-$x^L$:Bax heteromultimers and thereby increasing the relative amount of Bax:Bax homomultimers and free Bax, thereby increasing the susceptibility of the cell to death following an apoptotic stimulus.

The present invention provides several novel methods and compositions for modulating Bad and/or Bax and/or bcl-$x^L$ and/or bcl-2 activities and for screening for modulators of such activities. These methods utilize polynucleotide sequences encoding a Bad polypeptide and polynucleotides which are substantially identical to naturally-occurring polynucleotide sequences (e.g., cDNA or genomic gene) that encode such Bad polypeptides. The invention also provides methods for identifying agents which modulate Bad and/or Bax activity in vivo.

Accordingly, an embodiment of the invention involves the formation of a purified and/or isolated mammalian Bad protein and fragments thereof. In one aspect of the invention, Bad polypeptides and compositions thereof are provided. In an embodiment, the Bad polypeptides have the amino acid sequence of BH1 (PPNLWAAQRYGRELRRMSDEFEG) [SEQ. ID NO.:10] and/or BH2 (GWTRIIQSWWDRNTGK) [SEQ. ID NO:.17]. An embodiment involves a purified and/or isolated Bad protein comprising the amino acid sequence shown in FIG. 2(*a*) and denoted SEQ ID NO: 2:

MGTPKQPSLAPAHALGLR KSDPGIRSLGSDAGGRRWRPAAQSMFQIPEFEPSEQEDASATD SEQ ID NO: 2:
RGLGPSLTEDQPGPYLAPGLLGSNIHQQGRAATNSHHGGAGAMETRSRHSSYPAGTEEDEG
MEEELSPFRGRSRSAPPNLWAAQRYGRELRRMSDEFEGSFKGLPRPKSAGTATQMRQSAGW
TRIIQSWWDRNLGKGGSTPSQ or a substantially identical mutein, fragment, analog, or fusion protein thereof.

The invention provides Bad muteins comprising a BH1 domain (residues 137–160 of mouse Bad) and/or BH2 domain (residues 182–197 of mouse Bad) comprising an amino acid sequence having an amino acid substitution, addition, and/or deletion as compared to a naturally-occurring Bad protein (e.g., a naturally-occurring Bad protein obtained from a non-pathological mammalian specimen). In a variation, the invention provides Bad fragments comprising a BH-1 and/or BH2 domain, preferably both domains, wherein said fragments comprise a naturally-occurring Bad amino acid sequence and exhibit binding to bcl-2 and/or bcl-$x^L$ and/or inhibit cell death repressor function, or wherein such fragments comprise an amino acid substitution, addition, or deletion relative to the naturally-occurring Bad polypeptide sequence and which substantially lack binding to bcl-2, bcl-$x^L$, or other bcl-2-related protein, and/or have activity as a Bad competitive antagonist and/or enhance death repressor activity or block death repressor activity of endogenous bcl-2 or bcl-$x^L$ protein.

Another embodiment involves the formation of bcl-2 and Bax mutants wherein the native protein or fragment has at least one amino acid deleted or replaced by another amino acid and the mutants exhibits altered biological activity from the native protein or fragment.

Polynucleotide sequences encoding Bad polypeptides are provided. The characteristics of the cloned sequences are given, including the nucleotide and predicted amino acid sequences. Polynucleotides comprising these sequences can serve as templates for the recombinant expression of quantities of Bad polypeptides, such as full-length mammalian Bad. Many polynucleotides comprising these sequences can also serve as probes for nucleic acid hybridization to detect the transcription rate and mRNA abundance of Bad mRNA in individual cells (e.g., lymphocytes or other somatic or germ cell types) by in situ hybridization and the like, and in specific cell populations by Northern blot analysis and/or by in situ hybridization (Alwine et al.(1977) *Proc. Natl. Acad. Sci. U.S.A.* 74: 5350) and/or PCR amplification and/or LCR detection. Polynucleotide sequences encoding Bad polypeptides are also provided. The characteristics of the cloned sequences are given, including the nucleotide and predicted amino acid sequence in FIGS. 1 and 2. Polynucleotides comprising sequences encoding these amino acid sequences can serve as templates for the recombinant expression of quantities of Bad polypeptides, such as human Bad and murine Bad.

The invention also provides host cells expressing Bad polypeptides encoded by a polynucleotide other than a naturally-occurring Bad gene or homolog gene of the host cell (if present).

The invention provides screening assays for identifying agents which modulate (e.g., inhibit) binding of a Bad polypeptide to a bcl-2 or bcl-$x^L$ polypeptide and/or which modulate (e.g., inhibit) binding of a Bad polypeptide to an alternative bcl-2-related polypeptide.

In one embodiment, candidate therapeutic agents are identified by their ability to block the binding of a Bad polypeptide to a bcl-$x^L$ polypeptide under binding conditions. The Bad polypeptide preferably comprises the Bad BH1 and BH2 domains, and often is a full-length mature Bad protein. The bcl-$x^L$ polypeptide preferably comprises the bcl-$x^L$ BH1 and BH2 domains, and often is a full-length mature human bcl-$x^L$ protein. Compositions for identifying candidate therapeutic agents typically comprise: (1) a Bad polypeptide capable of binding to a Bad-interacting polypeptide (e.g., bcl-$x^L$, bcl-2), (2) a Bad-interacting polypeptide (e.g., bcl-$x^L$, bcl-2), (3) aqueous binding conditions (e.g., physiological conditions), and optionally (4) a host cell (e.g., a yeast cell, mammalian cell, bacterial cell), and optionally (5) a reporter polynucleotide, and optionally (6) a medium to support growth or maintenance of a host cell; an agent is typically added to such a composition for evaluation.

In an embodiment, a candidate therapeutic agent is identified by its ability to block the binding of a Bad fusion polypeptide to a bcl-$x^L$ fusion polypeptide in a yeast two-hybrid system, wherein the Bad fusion polypeptide comprises a Bad polypeptide sequence fused to a GAL4 DNA-binding domain vector (GAL4 DB) or a GAL4 activation domain vector (GAL4 AD) and wherein the bcl-$x^L$ fusion polypeptide comprises a bcl-$x^L$ polypeptide sequence fused to a GAL4 activation domain vector (GAL4 AD) or a GAL4 DNA-binding domain vector (GAL4 DB), respectively.

In an embodiment, a candidate therapeutic agent is identified by its ability to block the binding of a Bad fusion polypeptide to a bcl-2 fusion polypeptide in a yeast two-hybrid system, wherein the Bad fusion polypeptide comprises a Bad polypeptide sequence fused to a GAL4 DNA-binding domain vector (GAL4 DB) or a GAL4 activation domain vector (GAL4 AD) and wherein the bcl-2 fusion polypeptide comprises a bcl-2 polypeptide sequence fused to a GAL4 activation domain vector (GAL4 AD) or a GAL4 DNA-binding domain vector (GAL4 DB), respectively.

The invention also provides antisense polynucleotides complementary to polynucleotides encoding Bad polypeptide sequences. Such antisense polynucleotides are employed to inhibit transcription and/or translation of the Bad polypeptide mRNA species and thereby effect a reduction in the amount of the respective Bad polypeptide in a cell (e.g., a lymphocytic cell of a patient). Such antisense polynucleotides can function as Bad- or bcl-$x^L$-modulating agents by inhibiting the formation of Bad:bcl-$x^L$ complexes and increasing the relative abundance of free Bax and/or Bax:Bax complexes. The antisense polynucleotides can promote apoptotic cell death in susceptible cells (e.g., cells having an apoptotic stimulus). The Bad antisense polynucleotides are substantially identical to at least 25 contiguous nucleotides of the complementary sequence of the Bad cDNA sequence shown in FIG. 2(*b*) and denoted SEQ ID NO: 3. The Bad antisense polynucleotides are typically ssDNA, ssRNA, methylphosphonate backbone nucleic acids, phosphorothiolate backbone, polyamide nucleic acids, and the like antisense structures known in the art. In one aspect of the invention, an antisense polynucleotide is administered to inhibit transcription and/or translation of Bad in a cell.

In a variation of the invention, polynucleotides of the invention are employed for diagnosis of pathological conditions or genetic disease that involve neoplasia of other medical conditions related to Bad function, and more specifically conditions and diseases that involve alterations in the structure or abundance of a Bad polypeptide, RNA transcript or splicing intermediate, mRNA, or genomic gene locus.

The invention also provides antibodies which bind to Bad with an affinity of about at least $1\times10^7M^{-1}$ and which lack specific high affinity binding for a other bcl-2-related polypeptides. Such antibodies can be used as diagnostic reagents to identify cells exhibiting altered Bad function (e.g., senescent, preneoplastic, hyperplastic, or neoplastic cells) in a cellular sample from a patient (e.g., a lymphocyte sample, a solid tissue biopsy), as commercial reagents to identify, isolate, and/or quantitate Bad polypeptides in samples and histological specimens, and the like. Cells having a decreased relative amount of Bad protein are identified as being cells which have an decreased susceptibility to apoptosis (and hence an increased likelihood for cell proliferative disorders; hyperplasia, neoplasia) as compared to a control (or standardized) cell population of non-neoplastic cells of the same cell type(s). Frequently, anti-Bad antibodies are included as diagnostic reagents for immunohistopathology staining of cellular samples in situ. Additionally, anti-Bad antibodies may be used therapeutically by targeted delivery to neoplastic cells (e.g., by cationization or by liposome or immunoliposome delivery).

The invention also involves the use of the protein Bad or mutein or fragment thereof for performing immunochemical methods for the detection and determination of the protein or its associated protein bcl-$x^L$, in order to monitor cell survival versus death or to detect or monitor the course of diseases.

The invention also provides Bad polynucleotide probes for diagnosis of disease states (e.g., neoplasia or preneoplasia) by detection of a Bad mRNA or rearrangements or deletion of the Bad gene in cells explanted from a patient, or detection of a pathognomonic Bad allele (e.g., by RFLP or allele-specific PCR analysis). Typically, the detection will be by in situ hybridization using a labeled (e.g., $^{32}P$, $^{35}S$, $^{14}C$, $^{3}H$, fluorescent, biotinylated, digoxigeninylated) Bad polynucleotide, although Northern or Southern blotting, dot blotting, or solution hybridization on bulk genomic DNA, RNA, or poly $A^+$ RNA isolated from a cell sample may be used, as may PCR amplification using Bad-specific primers. Cells which contain an altered amount of Bad mRNA as compared to non-neoplastic cells of the same cell type(s) will be identified as candidate diseased cells. Similarly, the detection of pathognomonic rearrangements, deletion, or amplification of the Bad gene locus or closely linked loci in a cell sample will identify the presence of a pathological condition or a predisposition to developing a pathological condition (e.g., cancer, genetic disease). The polynucleotide probes are also used for forensic identification of individuals, such as for paternity testing or identification of criminal suspects or unknown decedents.

The present invention also provides a method for diagnosing a disease (e.g., neoplasia, preneoplasia, senescence) in a human patient, wherein a diagnostic assay (e.g., immunohistochemical staining of fixed cells by an antibody that specifically binds Bad polypeptides) is used to determine if a predetermined pathognomonic concentration of Bad polypeptide or its encoding mRNA is present in a biological sample from a human patient; if the assay indicates the presence of Bad polypeptide or its encoding mRNA outside of the normal range (e.g., outside the predetermined pathognomonic concentration range), the patient is diagnosed as having a disease condition or predisposition.

The invention also provides therapeutic agents which inhibit neoplasia or apoptosis by modulating Bad function by inhibiting or augmenting formation of complexes of Bad:bcl-$x^L$ polypeptides and/or Bad:bcl-2 polypeptides and/or complexes of Bad with other Bad-binding polypeptides; such agents can be used as pharmaceuticals. Such pharmaceuticals will be used to treat a variety of human and veterinary diseases, such as for example and not limitation: neoplasia, hyperplasia, benign prostatic hypertrophy, fibrocystic breast disease, reperfusion injury, myocardial infarction, stroke, traumatic brain injury, neurodegenerative diseases, aging, ischemia, toxemia, infection, AIDS, hepatitis, and the like.

The invention also provides methods for identifying polypeptide sequences which bind to a Bad polypeptide. For example, a yeast two-hybrid screening system can be used for identifying polypeptide sequences that bind to Bad. Yeast two-hybrid systems wherein one GAL4 fusion protein comprises a Bad polypeptide sequence, typically a full-length of near full-length Bad polypeptide sequence, and the other GAL4 fusion protein comprises a cDNA library member can be used to identify cDNAs encoding proteins which interact with the Bad polypeptide, can be screened according to the general method of Chien et al. (1991) *Proc. Natl. Acad. Sci. (USA)* 88: 9578. Alternatively, an *E. coli*/BCCP interactive screening system (Germino et al. (1993) *Proc. Natl. Acad. Sci. (U.S.A.)* 90: 933; Guarente L (1993) *Proc. Natl. Acad. Sci. (U.S.A.)* 90: 1639, incorporated herein by reference) can be used to identify interacting protein sequences. Also, an expression library, such as a λgt11 cDNA expression library, can be screened with a labelled Bad polypeptide to identify cDNAs encoding polypeptides which specifically bind to the Bad polypeptide. For these procedures, cDNA libraries usually comprise mammalian cDNA populations, typically human, mouse, simian, or rat, and may represent cDNA produced from RNA of one or more cell type, tissue, or organ and one or more developmental stage. Specific binding for screening cDNA expression libraries is usually provided by including one or more blocking agent (e.g., albumin, nonfat dry milk solids, etc.) prior to and/or concomitant with contacting the labeled Bad polypeptide (and/or labeled anti-Bad antibody).

The invention also provides a method of identifying candidate Bad modulating agents, comprising:

performing a heterodimerization assay which includes (1) a Bad polypeptide capable of binding to a bcl-2 and/or bcl-$x^L$ polypeptide species, (2) a bcl-2 polypeptide or bcl-$x^L$ polypeptide capable of binding to said Bad polypeptide under binding conditions, (3) and an agent;

determining whether the agent inhibits heterodimerization of the Bad polypeptide species to the bcl-2 or bcl-$x^L$ polypeptide;

identifying agents which inhibit said heterodimerization as candidate Bad modulating agents which modulate apoptosis, cell proliferation, senescence, and/or cell differentiation. Such candidate Bad modulating agents can serve as pharmaceuticals, commercial laboratory reagents, and solutes, among other uses.

The invention also provides a method of identifying candidate Bad-modulating agents, comprising:

performing a heterodimerization assay which includes a Bad polypeptide comprising a BH1 and/or BH2 domain with a bcl-2 or bcl-$x^L$ polypeptide comprising a BH1 and/or BH2 domain and an agent;

determining whether the agent inhibits heterodimerization of the Bad polypeptide to the bcl-2 or bcl-$x^L$ polypeptide;

identifying agents which inhibit said heterodimerization as candidate Bad-modulating agents which inhibit apoptosis.

The invention also provides a method of identifying candidate Bad-modulating agents, comprising:

performing a heterodimerization assay which includes a Bad polypeptide comprising a BH1 and/or BH2 domain with a bcl-2 or bcl-$x^L$ polypeptide comprising a BH1 and/or BH2 domain and an agent;

determining whether the agent inhibits heterodimerization of the Bad polypeptide to the bcl-2 or bcl-$x^L$ polypeptide;

identifying agents which enhance said heterodimerization as candidate Bad-modulating agents which enhance susceptibility to apoptosis and cell death.

In one aspect, the invention provides non-human animals (e.g., mice) which comprise a homozygous pair of functionally disrupted endogenous Bad alleles. Such functionally disrupted endogenous Bad alleles typically result from homologous gene targeting, and often comprise a naturally-occurring Bad allele which is (1) disrupted by deletion of an essential structural sequence (e.g., exon) or regulatory sequence (e.g., promoter, enhancer, polyadenylation site, splice junction site) or (2) disrupted by integration of an exogenous polynucleotide sequence (e.g., $neo^R$ gene) into an essential structural sequence (e.g., exon) or regulatory sequence (e.g., promoter, enhancer, polyadenylation site, splice junction site). Such Bad knockout animals can be sold commercially as test animals (e.g., as a preneoplastic animal for testing carcinogenic agents, such as a p53 knockout mouse or the Harvard OncoMouse™), bred to transfer the disrupted Bad allele(s) into other genetic backgrounds, and sold as disease models for screening for therapeutic agents, and the like. Such knockout animals have a wide variety of utilities, including serving as pets and sources of animal protein (e.g., as a foodstuff), among many other uses.

In one aspect of the invention, transgenic nonhuman animals, such as mice, bearing a transgene encoding a Bad polypeptide and/or a bcl-2 or bcl-$x^L$ polypeptide are provided. Such transgenes may be homologously recombined into the host chromosome or may be non-homologously integrated.

In an embodiment, the invention provides Bad polynucleotides for gene therapy and compositions of such Bad gene therapy vectors for treating or preventing disease.

Further included is a method for the treatment of a neurodegenerative disease, an immunodeficiency (e.g. AIDS), senescence, or ischemia, which comprises; decreasing the effective amount of Bad or administering a mutein or fragment thereof (or polynucleotide encoding same) to a patient to increase the effective ratio of bcl-2 to Bax and/or bcl-$x^L$ to Bax to promote the survival of cells by generating an excess of bcl-2 and/or bcl-$x^L$ available to bind Bax; and, a method for the treatment of hyperplasia, hypertrophies, cancers and autoimmunity disorders, which comprises: increasing the effective amount of Bad or administering a mutein or fragment thereof (or polynucleotide encoding same) to a patient to regulate the ratio of bcl-2 to Bax and/or bcl-$x^L$ to Bax so as to favor Bax:Bax homomultimer formation and promote cell death. In a variation, the method comprises administering an agent which modifies heterodimerization of Bad to bcl-2 and/or to bcl-$x^L$. In a variation, the method comprises administering a fragment, mutein, or peptidomimetic of a bcl-2-related protein (e.g., Bad, Bax, bcl-2, bcl-$x^L$, bcl-xS, Mcl-1, A1, or homologues).

Another embodiment involves an associated protein, which comprises Bad protein coupled with a Bad-associated protein or fragments thereof.

A further embodiment involves a polynucleotide (e.g., a DNA isolate) consisting essentially of a genomic DNA sequence encoding Bad and more particularly a composition consisting of c DNA molecules which encode the Bad protein.

A further embodiment involves a polynucleotide (e.g., a DNA isolate) consisting essentially of a genomic DNA sequence encoding human Bax and more particularly a composition consisting of c DNA molecules which encode the Bax protein.

Another aspect of the invention involves Bad pharmaceutical compositions, which contain pharmaceutically effective amounts of a Bad polypeptide, Bad polynucleotide, and/or Bad-modulating agent, and a suitable pharmaceutical carrier or delivery system.

The invention also comprises a method for identifying mutant Bad proteins which substantially lack binding to bcl-2 and/or bcl-$x^L$ and/or substantially enhance death repressor activity, said method comprising the steps of:

introducing a mutation into a Bad polynucleotide encoding a Bad polypeptide to produce a mutated Bad polynucleotide, whereby said mutated Bad polynucleotide encodes a mutant Bad polypeptide comprising an amino acid substitution or deletion in a BH1 or BH2 domain;

expressing said mutant Bad polypeptide in a mammalian cell which expresses bcl-2 and/or bcl-$x^L$ and which is capable of undergoing bcl-2-sensitive apoptosis;

determining whether expression of the mutant Bad polypeptide enhances death repressor activity of a bcl-2 or bcl-$x^L$ protein endogenous to said mammalian cell and/or whether said mutant Bad protein itself competes with endogenous, naturally-occurring Bad for bcl-2/bcl-$x^L$ binding and thereby enhances death repressor activity and/or is incapable of providing inhibition of said bcl-2/bcl-$x^L$-dependent repression of apoptosis; and identifying mutant Bad proteins which derepress endogenous bcl-2/bcl-$x^L$ death repressor activity in the presence of endogenous naturally-occurring Bad and/or which are capable of enhancing death repressor activity of bcl-2 and/or bcl-$x^L$ in a cell.

A further understanding of the nature and advantages of the invention will become apparent by reference to the remaining portions of the specification and drawings.

BRIEF DESCRIPTION OF THE DRAWINGS

FIG. 1 [SEQ. ID NO:1]. Sequence of murine Bad. Nucleotide and predicted amino acid sequence of murine Bad. Bold and double underlined residues are conserved amino acids in BH1 and BH2. The two stretches of dotted underlined amino acids indicate PEST sequences. Single underlined triplets in the 5' untranslated region are two in-frame stop codons. The polyadenylation site is shown in underlined italics. Numbers to the right of the sequence are nucleotide positions, numbers to the left are amino acid positions.

FIGS. 2(*a* & *b*). (2*a*) Polynucleotide coding sequence of mouse Bad cDNA [SEQ ID NO.:2]. (2*b*) Deduced amino acid sequence of mouse Bad [SEQ. ID NO.:3].

FIGS. 3(*a* & *b*). Isolation of Bad. (3*a*) The pPC97Bcl-2ΔC21 plasmid used as bait was transformed into PCY2 yeast cells; the resultant strain was then transformed with a GAL4-activation domain-cDNA fusion library, and plated on -ura-leu-trp media. (3*b*) The bacterially produced GST-HMK-Bcl-2ΔC21 fusion protein was labeled in vitro with $^{32}$p-γ-ATP and used to probe phage library filters. HMK, heart muscle kinase motif.

FIGS. 4(*a–c*). (4*a*) cDNA inserts from E14.5 cDNA fusion library. The stretch of 9 adenines in the 3' untranslated region served as an oligo-dt priming site for some isolates. (4*b*) cDNA inserts from E16 Ex-lox library. (4*c*) Composite full-length murine cDNA from newborn brain and adult thymus libraries.

FIGS. 5(*a–c*). Alignment of Bad and bcl-2 family members in BH1 and BH2 domains. (5*a*) Schematic representation of bcl-2 BH1 and BH2 domains. Numbers denote amino acid positions in the protein. (5*b* and 5*c*) The most conserved amino acids in BH1 and BH2 are shaded. Dashes denote gaps in the sequence to maximize alignment [Bcl-2 (mouse), aa 133–152 is SEQ ID NO.:4; Bax (mouse), aa 98–118 is SEQ ID NO.:5; Bcl-$x_L$ (mouse), aa 129–148 is SEQ ID NO.:6; A1 (mouse), aa 77–97 is SEQ ID NO.:7; Mcl-1 (mouse), aa 233–253 is SEQ ID NO.:8; Ced-9 (*C. elegans*), aa 159–179 is SEQ ID NO.:9; Bcl-2 (mouse), aa 184–200 is SEQ ID NO.:11; Bax-1 (mouse), aa 150–166 is SEQ ID NO.:12; Bcl-$x_L$ (mouse), aa 180–191 is SEQ ID NO.:13; A1 (mouse), aa 132–148 is SEQ ID NO.:14; Mcl-1 (mouse), aa 285–301 is SEQ ID NO.:15; Ced-9 (*C. elegans*), aa 213–229 is SEQ ID NO.:16].

FIG. 9. Interaction of Bad with bcl-2 family members in the yeast two-hybrid system. PCY2 yeast strain was transfromed with pairs of GAL4-DNA binding domain and GAL4-activating domain plasmids. Liquid cultures of transformants were spotted on nitrocellulose filters for X-gal assays. Standardized protein lysates were prepared from the same cultures for ONPG assays. The β-galactosidase activity for each gene within the pAS plasmid together with an empty pACTII plasmid was normalized to 1.0. pASBAX, pASBCL-$X_S$, and pASA1 constructs all displayed spurious transcription activation and could not be further assessed.

FIGS. 13(*a–d*). Co-immunoprecipitation of bcl-$x_L$ and Bad. (13*a*) Primary immunoprecipitation of the $^{35}$S-labeled FL5.12Bcl-$X_L$ line (lanes 2, 3, 4) and one of the pSFFVHA-Bad transfected clones (lanes 5, 6, 7), using anti-bcl-x Ab, anti-HAmAb (12CA5), and anti-Bad Ab. One-third of each sample was loaded on a 12.5% SDSPAGE gel and fluorographed. (13*b*) Western blot analysis of one-third of each primary immunoprecipitate using biotinylated anti-bcl-x Ab, developed with DAB. (13*c*) Western blot analysis of one-third of each primary immunoprecipitate using biotinylated anti-Bad Ab, developed with DAB. (13*d*) Primary immunoprecipitation of $^{35}$S-labeled FL5.12Bcl-$X_L$HA-Bad#7 with anti-bcl-x Ab (lane 2), and secondary immunoprecipitation of that supernatant with 12CA5 mAb (lane 3).

DESCRIPTION OF THE PREFERRED EMBODIMENTS

Figure 6A:
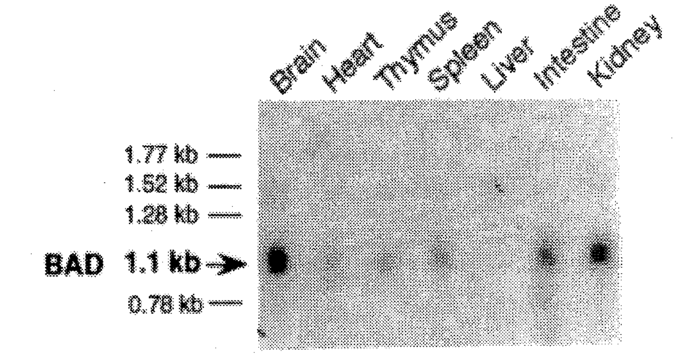
FIG. 6. Tissue Northern analysis and RT-PCR of Bad and bcl-$x_L$. Total RNAs from mouse tissues were probed with a PCR labeled Bad cDNA probe. The blot was reprobed with a PCR labeled bcl-$x_L$ cDNA probe. Finally, it was stripped and probed with glyceraldehyde-3-phosphate dehydrogenase to quantitate the amount of RNA loaded in each lane.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

Definitions

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Mass. (1991), which is incorporated herein by reference). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

As used herein, the term "Bad" refers to the mammalian Bad gene and mammalian Bad proteins, including isoforms thereof, unless otherwise identified; human and murine Bad proteins and genes are preferred exemplifications of mammalian Bad, and in its narrowest usage Bad refers to a Bad polynucleotide and polypeptide sequences having substantial identity to SEQ ID NO: 2, or is at least 85 percent substantially identical to SEQ ID NO: 2, or is at least 90–95 percent substantially identical to SEQ ID NO: 2.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 1 or FIG. 2(*b*), or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length Bad polynucleotide sequence shown in FIG. 1 or FIG. 2(*a*) or a segment of a Bad protein, such as a fragment spanning residues 137–160 (BH1) and/or 182–197 (BH2).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "Bad native protein" and "full-length Bad protein" as used herein refers to a full-length Bad polypeptide of 204 amino acids as shown herein (see, FIGS. 1 and 2(*a*)) or as naturally occurs in a mammalian species (e.g., mouse, human, simian, rat, etc.). A preferred Bad native protein is the polypeptide corresponding to the deduced amino acid sequence shown in FIG. 2(*a*) or corresponding to the deduced amino acid sequence of a cognate full-length Bad cDNA of another species (e.g., human). Also for example, a native Bad protein present in naturally-occurring somatic cells which express the Bad gene are considered full-length Bad proteins.

The term "fragment" as used herein refers to a polypeptide that has an amino-terminal and/or carboxy-terminal deletion, but where the remaining amino acid sequence is identical to the corresponding positions in the sequence deduced from a full-length cDNA sequence (e.g., the cDNA sequence shown in FIG. 2(*a*)). Fragments typically are at least 14 amino acids long, preferably at least 20 amino acids long, usually at least 50 amino acids long or longer, up to the length of a full-length naturally-occurring Bad polypeptide (e.g., about 204 amino acids).

The term "analog", "mutein" or "mutant" as used herein refers to polypeptides which are comprised of a segment of at least 10 amino acids that has substantial identity to a portion of the naturally occurring protein. For example, a Bad analog comprises a segment of at least 10 amino acids that has substantial identity to a Bad protein, such as the Bad protein of FIG. 2(*a*); preferably a deduced amino acid sequence of a mammalian Bad cDNA. In an embodiment, a Bad analog or mutein has at least one of the following properties: binding to bcl-2 or binding to native bcl-$x^L$ protein under suitable binding conditions. Typically, analog polypeptides comprise a conservative amino acid substitution (or addition or deletion) with respect to the naturally-occurring sequence. Analogs typically are at least 20 amino acids long, preferably at least 50 amino acids long or longer, most usually being as long as full-length naturally-occurring protein (e.g., 204 amino acid residues for mouse Bad). Some analogs may lack biological activity (e.g., bcl-2 or bcl-$x^L$ binding) but may still be employed for various uses, such as for raising antibodies to Bad epitopes, as an immunological reagent to detect and/or purify α-Bad antibodies by affinity chromatography, or as a competitive or noncompetitive agonist, antagonist, or partial agonist of native Bad protein function.

The term "Bad polypeptide" is used herein as a generic term to refer to native protein, fragments, or analogs of Bad, or such fused to a second polypeptide sequence (e.g., an epitope tag, β-gal, or other fusion). Hence, native Bad, fragments of Bad, and analogs of Bad, as well as Bad fusion proteins are species of the Bad polypeptide genus. Preferred Bad polypeptides include: a murine full-length Bad protein comprising the murine polypeptide sequence shown in FIG. 2(*a*), a full-length human Bad protein comprising a polypeptide sequence encoded by a human Bad cDNA which can be isolated by the methods described infra, polypeptides consisting essentially of the sequence of Bad domain I or domain II, and the naturally-occurring mouse Bad isoforms, including post-translationally modified isoforms. Generally, Bad polypeptides are less than 5,000 amino acids long, usually less than 1000 amino acids long.

The term "bcl-2 polypeptide" is used herein as a generic term to refer to native protein, fragments, analogs, or fusions of bcl-2, preferably human or murine bcl-2, usually human bcl-2.

The term "bcl-$x^L$ polypeptide" is used herein as a generic term to refer to native protein, fragments, analogs, or fusions of bcl-$x^L$, preferably human or murine bcl-$x^L$, usually human bcl-$x^L$.

The term "Bax polypeptide" is used herein as a generic term to refer to native protein, fragments, analogs, or fusions of Bax, preferably human or murine Bax, usually human Bax.

The term "Bad polynucleotide" as used herein refers to a polynucleotide of at least 15 nucleotides wherein the polynucleotide comprises a segment of at least 15 nucleotides which: (1) are at least 85 percent identical to a naturally-occurring Bad mRNA sequence or its complement or to a naturally-occurring Bad genomic structural gene sequence, and/or (2) encode a Bad polypeptide. Due to the degeneracy of the genetic code, some Bad polynucleotides encoding a Bad polypeptide will be less that 85 percent identical to a naturally-occurring Bad polynucleotide. Similarly, some Bad polynucleotides which are suitable as hybridization probes, PCR primers, LCR amplimers, and the like will not encode a Bad polypeptide.

The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition. Thus, the cognate human gene to the murine Bad gene is the human gene which encodes an expressed protein which has the greatest degree of sequence identity to the murine Bad protein and which exhibits an expression pattern similar to that of the murine Bad (e.g., expressed in an equivalent tissue-specific expression pattern). Preferred cognate Bad genes are: rat Bad, rabbit Bad, canine Bad, nonhuman primate Bad, porcine Bad, bovine Bad, and hamster Bad. Cognate genes to Bad in non-mammalian species (e.g., *C. elegans,* avians, fish) can also be isolated.

The term "agent" is used herein to denote a chemical compound, a mixture of chemical compounds, an array of spatially localized compounds (e.g., a VLSIPS peptide array, polynucleotide array, and/or combinatorial small molecule array), a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues. Agents are evaluated for potential activity as antineoplastics, anti-inflammatories, or apoptosis modulators by inclusion in screening assays described hereinbelow. Agents are evaluated for potential activity as specific protein interaction inhibitors (i.e., an agent which selectively inhibits a binding interaction between two predetermined polypeptides but which does not substantially interfere with cell viability) by inclusion in screening assays described hereinbelow.

The term "protein interaction inhibitor" is used herein to refer to an agent which is identified by one or more screening method(s) of the invention as an agent which selectively inhibits protein-protein binding between a first interacting polypeptide and a second interacting polypeptide. Some protein interaction inhibitors may have therapeutic potential as drugs for human use and/or may serve as commercial reagents for laboratory research or bioprocess control. Protein interaction inhibitors which are candidate drugs are then tested further for activity in assays which are routinely used to predict suitability for use as human and veterinary drugs, including in vivo administration to non-human animals and often including administration to human in approved clinical trials.

The term "antineoplastic agent" is used herein to refer to agents that have the functional property of inhibiting a development or progression of a neoplasm in a human, particularly a lymphocytic leukemia, lymphoma or pre-leukemic condition.

The term "bcl-2 antagonist" is used herein to refer to agents which inhibit bcl-2 activity and can produce a cell phenotype characteristic of cells having reduced or undetectable expression of bcl-2; bcl-2 antagonists typically will enhance apoptosis. In contradistinction, bcl-2 agonists will enhance bcl-2 activity and will usually reduce apoptosis.

The term "bcl-$x^L$ antagonist" is used herein to refer to agents which inhibit bcl-$x^L$ activity and can produce a cell phenotype characteristic of cells having reduced or undetectable expression of bcl-$x^L$; bcl-$x^L$ antagonists typically will enhance apoptosis. In contradistinction, bcl-$x^L$ agonists will enhance bcl-$x^L$ activity and will usually reduce apoptosis.

The term "Bad antagonist" is used herein to refer to agents which inhibit Bad activity and can produce a cell phenotype characteristic of cells having reduced or undetectable expression of Bad; Bad antagonists typically will reduce or inhibit apoptosis. In contradistinction, Bad agonists will enhance Bad activity and will usually enhance susceptibility to apoptosis.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3H$, $^{14}C$, $^{35}S$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), biotinyl groups, predetermined polypeptide epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein "normal blood" or "normal human blood" refers to blood from a healthy human individual who does not have an active neoplastic disease or other disorder of lymphocytic proliferation, or an identified predisposition for developing a neoplastic disease Similarly "normal cells", "normal cellular sample", "normal tissue", and "normal lymph node" refers to the respective sample obtained from a healthy human individual who does not have an active neoplastic disease or other lymphoproliferative disorder.

As used herein the terms "pathognomonic concentration", "pathognomonic amount", and "pathognomonic staining pattern" refer to a concentration, amount, or localization pattern, respectively, of a Bad protein or mRNA in a sample, that indicates the presence of a pathological (e.g., neoplastic, senescent, immunodeficient, neurodegenerative, inflammatory, etc.) condition or a predisposition to developing a neoplastic disease, such as carcinoma, sarcoma, or leukemia. A pathognomonic amount is an amount of a Bad protein or Bad mRNA in a cell or cellular sample that falls outside the range of normal clinical values that is established by prospective and/or retrospective statistical clinical studies. Generally, an individual having a neoplastic disease (e.g., carcinoma, sarcoma, or leukemia) will exhibit an amount of Bad protein or mRNA in a cell or tissue sample that is outside the range of concentrations that characterize normal, undiseased individuals; typically the pathognomonic concentration is at least about one standard deviation outside the mean normal value, more usually it is at least about two standard deviations or more above the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50–200 mM NaCl or KCl, pH 6.5–8.5, 20°–45° C. and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or metal chelators and/or nonionic detergents and/or membrane fractions and/or antifoam agents and/or scintillants.

As used herein, the terms "interacting polypeptide segment" and "interacting polypeptide sequence" refer to a portion of a hybrid protein which can form a specific binding interaction with a portion of a second hybrid protein under suitable binding conditions. Generally, a portion of the first hybrid protein preferentially binds to a portion of the second hybrid protein forming a heterodimer or higher order heteromultimer comprising the first and second hybrid proteins; the binding portions of each hybrid protein are termed interacting polypeptide segments. Generally, interacting polypeptides can form heterodimers with a dissociation constant ($K_D$) of at least about $1\times10^3M^{-1}$, usually at least $1\times10^4M^{-1}$, typically at least $1\times10^5M^{-1}$, preferably at least $1\times10^6M^{-1}$ to $1\times10^7M^{-1}$ or more, under suitable physiological conditions.

As used herein, the term "multimer" comprises dimer and higher order complexes (trimer, tetramer, pentamer, hexamer, heptamer, octamer, etc.). "Homomultimer" refers to complexes comprised of the same subunit species. "Heteromultimer" refers to complexes comprised of more than one subunit species.

The term "recombinant" used herein refers to Bax and bcl-2 produced by recombinant DNA techniques wherein the gene coding for protein is cloned by known recombinant DNA technology. For example, the human gene for Bax may be inserted into a suitable DNA vector, such as a bacterial plasmid, and the plasmid used to transform a suitable host. The gene is then expressed in the host to produce the recombinant protein. The transformed host may be prokaryotic or eukaryotic, including mammalian, yeast, Aspergillus and insect cells. One preferred embodiment employs bacterial cells as the host.

Overview

It is known that the development as well as the maintenance of many adult tissues is achieved by several dynamically regulated processes that include cell proliferation, differentiation and programmed cell death. In the latter process, cells are eliminated by a highly characteristic suicide program entitled apoptosis.

bcl-2 was first isolated at the chromosomal breakpoint of t(14;18) bearing follicular B cell lymphomas. Transgenic mice bearing a bcl-2-Ig mini-gene that recapitulates this translocation display a polyclonal follicular hyperplasia with a four-fold increase in resting B cells and as such B cells accumulate because of extended cell survival rather than increased proliferation.

A survey of adult tissues indicates that bcl-2 has played several roles in numerous cell lineages. Glandular epithelium that undergoes hyperplasia or involution in response to hormonal stimuli or growth factors express bcl-2. In complex epithelium, such as the skin and gut, bcl-2 is generally restricted to stem cells and proliferation zones. Within the adult nervous system bcl-2 is more prominent in the peripheral nervous system rather than the central nervous system. Thus, bcl-2 can be needed to save the progenitor and long-lived cells in a variety of cell lineages.

bcl-2 appears to function in several subcellular locations. It was been unexpectedly discovered that bcl-2 associates, in vivo with a 21 kD protein partner, called Bax. Bax shows extensive amino acid homology with bcl-2 and forms homodimers with itself and heterodimers with bcl-2 and bcl-$x^L$ in vivo. Bax is encoded by 6 exons and demonstrates a complex pattern of alternative RNA splicing that predicts a 21 Kd membrane ($\alpha$) and two forms ($\beta$ and $\gamma$) of cytosolic protein. When Bax predominates, programmed cell death is accelerated and the death repressor activity of bcl-2 and/or bcl-$x^L$ is countered.

It has been discovered that the ratio of bcl-2/Bax and/or bcl-$x^L$/Bax determines a cells susceptibility to death following an apoptotic stimulus. In the presence of IL-3 overexpressed Bax does not noticeably alter normal cell division or viability. Bax is present and associated with bcl-2 and/or bcl-$x^L$ prior to growth factor deprivation. Bax RNA is expressed in normal tissues and in a variety of cell lines prior to a death induction signal. The synthesis of Bax does not appear to be a de novo response that follows a death stimulus, and Bax in itself accelerates apoptotic cell death only following a death signal, such as IL-3 deprivation. Excess Bax also counters the death repressor activity of bcl-2. When bcl-2 is in excess cells are protected. However, when Bax is in excess and Bax homodimers dominate, cells are susceptible to apoptosis.

A basis of the present invention is the unexpected discovery of a naturally-occurring protein, Bad, which binds to bcl-$x^L$ and less avidly binds to bcl-2 in a two-hybrid system and in vivo. Bad binds to bcl-$x^L$ and/or bcl-2 and reduces the death repressor activity of bcl-$x^L$ and/or bcl-2, thereby making a cell more susceptible to apoptosis. Without wishing to be bound by any particular model or explanation, it is generally believed that by when Bad binds to bcl-$x^L$ and/or bcl-2, it effectively sequesters these species so that the formation of Bax:bcl-$x^L$ complexes and/or Bax:bcl-2 complexes is reduced, and the relative amount of free Bax and/or Bax:Bax homomultimers (homodimers) is increased, and thereby the susceptibility of a cell to an apoptosis stimulus and cell death is increased.

These discoveries are consistent with a model in which the response of a cell to a death signal is determined by a preset mechanism, such as the ratio of bcl-2/Bax and/or bcl-$X^L$/BaX, and Bad modulates the effective levels of non-sequestered bcl-2 and/or bcl-$x^L$ available to complex with Bax in a cell.

Because of these interactions it is possible to use this invention for the detection and determination of Bad, Bax bcl-$x^L$ and/or bcl-2 and complexes thereof, for example in a fraction from a tissue or organ separation operation, or immunochemical technique in view of the proteins antigenic properties. Specific antibodies can also be formed on immunization of animals with this protein.

Bad Polypeptides and Polynucleotides

The nomenclature used hereafter and the laboratory procedures in cell culture, molecular genetics, and nucleic acid chemistry and hybridization described below may involve well known and commonly employed procedures in the art. Standard techniques are used for recombinant nucleic acid methods, polynucleotide synthesis, and microbial culture and transformation (e.g., electroporation, lipofection). The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold spring Harbor, N.Y., which is incorporated herein by reference) which are provided throughout this document.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. H. A. Erlich, Freeman Press, New York, N.Y. (1992); *PCR Protocols: A Guide to Methods and Applications,* eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; PCR, eds. McPherson, Quirkes, and Taylor, IRL Press, Oxford; and U.S. Pat. No. 4,683,202, which are incorporated herein by reference).

Cloning of Bad Polynucleotides

Disclosure of the full coding sequences for murine Bad shown in FIG. 1 and FIGS. 2(*a*) and 2(*b*) makes possible the construction of isolated polynucleotides that can direct the expression of Bad, fragments thereof, or analogs thereof. Further, the sequences in FIG. 1 and FIGS. 2(*a*) and 2(*b*) make possible the construction of nucleic acid hybridization probes and PCR primers that can be used to detect RNA and DNA sequences encoding Bad.

Polynucleotides encoding full-length Bad or fragments or analogs thereof, may include sequences that facilitate transcription (expression sequences) and translation of the coding sequences, such that the encoded polypeptide product is produced. Construction of such polynucleotides is well known in the art and is described further in Maniatis et al., *Molecular Cloning: A Laboratory Manual,* 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a Bad polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large TAg poly A addition site).

Preferably, these amino acid sequences occur in the given order (in the amino-terminal to carboxy-terminal orientation) and may comprise other intervening and/or terminal sequences; generally such polypeptides are less than 1000 amino acids in length, more usually less than about 500 amino acids in lengths, and frequently approximately 204 amino acids in length. The degeneracy of the genetic code gives a finite set of polynucleotide sequences encoding these amino acid sequences; this set of degenerate sequences may be readily generated by hand or by computer using commercially available software (Wisconsin Genetics Software Package Relaes 7.0). Isolated Bad polynucleotides typically are less than approximately 10,000 nucleotides in length.

Additionally, where expression of a polypeptide is not desired, polynucleotides of this invention need not encode a functional protein. Polynucleotides of this invention may serve as hybridization probes and/or PCR primers (amplimers) and/or LCR oligomers for detecting Bad RNA or DNA sequences.

Alternatively, polynucleotides of this invention may serve as hybridization probes or primers for detecting RNA or DNA sequences of related genes, such genes may encode structurally or evolutionarily related proteins. For such hybridization and PCR applications, the polynucleotides of the invention need not encode a functional polypeptide. Thus, polynucleotides of the invention may contain substantial deletions, additions, nucleotide substitutions and/or transpositions, so long as specific hybridization or specific amplification to a Bad sequence is retained.

Genomic or cDNA clones encoding Bad may be isolated from clone libraries (e.g., available from Clontech, Palo Alto, Calif.) using hybridization probes designed on the basis of the nucleotide sequences shown in FIG. 1 and FIGS. 2(*a*) and 2(*b*) and using conventional hybridization screening methods (e.g., Benton W. D. and Davis R. W. (1977) *Science* 196: 180; Goodspeed et al. (1989) *Gene* 76: 1). Where a cDNA clone is desired, clone libraries containing cDNA derived from somatic cell mRNA or other Bad-expressing cell mRNA are preferred. Alternatively, synthetic polynucleotide sequences corresponding to all or part of the sequences shown in FIG. 1 and FIG. 2(*b*) may be constructed by chemical synthesis of oligonucleotides. Additionally, polymerase chain reaction (PCR) using primers based on the sequence data disclosed in FIG. 1 and FIGS. 2(*a*) and 2(*b*) may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIG. 1 and a second primer that is not based on that sequence data may be used. For example, a second primer that is homologous to or complementary to a polyadenylation segment may be used.

Provided in the invention are polynucleotides comprising a segment encoding a Bad epitope or a multiplicity of Bad epitopes. Preferred Bad epitopes are: -GTPKQPSLAPA-HAL-[SEQ ID NO.:18]; -RKSDPGIRSLGSDA-[SEQ ID NO.:19]; -RWRPAAQSMFQIPEFEP-[SEQ ID NO.:20]; -EQEDASATDRGLGPSLT-[SEQ ID NO.:21]; -PGPY-LAPGLLGSNIHQQ-[SEQ ID NO.:22]; -RAATNSHHG-GAGAMETRS-[SEQ ID NO.:23]; -HSSYPAGTEEDEG-[SEQ ID NO.:24]; -EELSPFRGRSRSAPPN-[SEQ ID NO.:25]; -WAAQRYGRELRRMSDE-[SEQ ID NO.:26]; -SFKGLPRPKSAGTATQM-[SEQ ID NO.:27]; -SAG-WTRIIQSWWDRNL-[SEQ ID NO.:28] -PPNL-WAAQRYGRELRRMSDEFEG-[SEQ ID NO.:10] and -GWTRIIQSWWDRNLGK-[SEQ ID NO.:17]. Polynucleotides encoding epitopes having substantial identity to these preferred epitopes are often employed. Such polynucleotides have a variety of uses, including as Bad probes, as templates for producing polypeptides comprising a Bad epitope whereby such proteins are Bad immunogens or commercial diagnostic reagents for standardizing a Bad immunoassay, as polynucleotide vaccines (immunogens) when fused to a secretory sequence for administering to an animal and making α-Bad antisera and hybridomas; such polynucleotides can also be used as foodstuffs, combustible energy sources, and viscosity-enhancing solutes.

Isolation of the Cognate Human Bad Gene

The human homolog of the murine Bad gene or cDNA is identified and isolated by screening a human genomic or cDNA clone library, such as a human genomic or cDNA library in yeast artificial chromosomes, cosmids, or bacteriophage λ (e.g., λ Charon 35), with a polynucleotide probe comprising a sequence of about at least 24 contiguous nucleotides (or their complement) of the cDNA sequence shown in FIG. 1 or FIG. 2(*b*). Typically, hybridization and washing conditions are performed at high stringency according to conventional hybridization procedures. Positive clones are isolated and sequenced. For illustration and not for limitation, a full-length polynucleotide corresponding to the sequence of FIG. 1 or FIG. 2(*b*) may be labeled and used as a hybridization probe to isolate genomic clones from a human or murine genomic clone library in λEMBL4 or λGEM11 (Promega Corporation, Madison, Wis.); typical hybridization conditions for screening plaque lifts (Benton and Davis (1978) *Science* 196: 180) can be: 50% formamide, 5×SSC or SSPE, 1–5×Denhardt's solution, 0.1–1% SDS, 100–200 μg sheared heterologous DNA or tRNA, 0–10% dextran sulfate, $1\times10^5$ to $1\times10^7$ cpm/ml of denatured probe with a specific activity of about $1\times10^8$ cpm/μg, and incubation at 42° C.–37° C. for about 6–36 hours. Prehybridization conditions are essentially identical except that probe is not included and incubation time is typically reduced. Washing conditions are typically 1–3×SSC, 0.1–1% SDS, 50°–70° C. with change of wash solution at about 5–30 minutes. For isolating human Bad polynucleotides with a mouse Bad polynucleotide probe, it is often preferred to hybridize at approximately 39° C. and to wash sequentially at the following step temperatures: room temperature, 37° C., 39° C., 42° C., 45° C., 50° C., 55° C., 60° C., 65° C., and 70° C., stopping after each step and monitoring the background probe signal (and optionally detecting signal by autoradiogram and/or phosphor imaging, if radiolabeled probe is used) and terminating the washing steps when suitable signal/noise ratio is achieved, as determined empirically.

Human and other non-mouse Bad cDNAs and genomic clones (i.e., cognate human and nonhuman genes) can be analogously isolated from various human or nonhuman cDNA and genomic clone libraries available in the art (e.g., Clontech, Palo Alto, Calif.) by using probes based on the sequences shown in FIG. 1 or FIGS. 2(*a*) and 2(*b*), with hybridization and washing conditions typically being less stringent than for isolation of mouse Bad clones.

Polynucleotides comprising sequences of approximately at least 30–50 nucleotides, preferably at least 100 nucleotides, corresponding to or complementary to the nucleotide sequences shown in FIG. 1 or FIG. 2(*b*) can serve as PCR primers and/or hybridization probes for identifying and isolating germline genes corresponding to Bad. These germline genes may be human or may be from a related mammalian species, preferably rodents or primates. Such germline genes may be isolated by various methods conventional in the art, including, but not limited to, by hybridization screening of genomic libraries in bacteriophage λ or cosmid libraries, or by PCR amplification of genomic sequences using primers derived from the sequences shown in FIG. 1 or FIG. 2(*b*). Human genomic libraries are publicly available or may be constructed de novo from human DNA.

It is apparent to one of skill in the art that nucleotide substitutions, deletions, and additions may be incorporated into the polynucleotides of the invention. Nucleotide sequence variation may result from sequence polymorphisms of various Bad alleles, minor sequencing errors, and the like. However, such nucleotide substitutions, deletions, and additions should not substantially disrupt the ability of the polynucleotide to hybridize to one of the polynucleotide sequences shown in FIG. 1 or FIG. 2(*b*) under hybridization conditions that are sufficiently stringent to result in specific hybridization.

Specific hybridization is defined herein as the formation of hybrids between a probe polynucleotide (e.g., a polynucleotide of the invention which may include substitutions, deletion, and/or additions) and a specific target polynucleotide (e.g., a polynucleotide having the sequence in FIG. 1 or FIG. 2(*b*), wherein the probe preferentially hybridizes to the specific target such that, for example, a single band corresponding to one or more of the RNA species of Bad (or alternatively spliced mRNA species) can be identified on a Northern blot of RNA prepared from a suitable cell source (e.g., a somatic cell expressing Bad). Polynucleotides of the invention and recombinantly produced Bad, and fragments or analogs thereof, may be prepared on the basis of the sequence data provided in FIG. 1 and FIGS. 2(*a*) and 2(*b*) according to methods known in the art and described in Maniatis et al., *Molecular Cloning: A Laboratory Manual,* 2nd Ed., (1989), Cold Spring Harbor, N.Y. and Berger and Kimmel, *Methods in Enzymology, Volume* 152, *Guide to Molecular Cloning Techniques* (1987), Academic Press, Inc., San Diego, Calif., which are incorporated herein by reference.

Bad polynucleotides may be short oligonucleotides (e.g., 20–100 bases long), such as for use as hybridization probes and PCR (or LCR) primers. Bad polynucleotide sequences may also comprise part of a larger polynucleotide (e.g., a cloning vector comprising a Bad clone) and may be fused, by polynucleotide linkage, in frame with another polynucleotide sequence encoding a different protein (e.g., glutathione S-transferase or β-galactosidase) for encoding expression of mRNA, for example to diagnose a lymphoproliferative disease characterized by the presence of an elevated or reduced Bad mRNA level in lymphocytes, or to perform tissue typing (i.e., identify tissues characterized by the expression of Bad mRNA), and the like. The sequences may also be used for detecting genomic Bad gene sequences in a DNA sample, such as for forensic DNA analysis (e.g., by RFLP analysis, PCR product length(s) distribution, etc.) or for diagnosis of diseases characterized by amplification and/or rearrangements of the Bad gene. Alternatively, Bad polynucleotides can be used as a foodstuff, combustible energy source, viscosity-enhancing solute, and the like. In a variation of the invention, polynucleotides of the invention are employed for diagnosis of pathological conditions or genetic disease that involve neoplasia of other medical conditions related to Bad function, and more specifically conditions and diseases that involve alterations in the structure or abundance of a Bad polypeptide.

For example and not limitation, the following pair of oligonucleotide primers can be used to amplify Bad polynucleotide sequences (e.g., cDNA) or as hybridization probes (e.g., as biotinylated or end-labeled oligonucleotide probes):

5'-ATAAAGCACGTTTCTCGCGACCTC-3' [SEQ ID NO.:29] and

5'-GGCACGAGCGGACCCCGCCCCCTAG-3' [SEQ ID NO.:30].

Other suitable PCR primers, LCR primers, hybridization probes, exon-specific hybridization probes and primers, degenerate oligonucleotides encoding Bad polypeptide sequences, and the like are apparent to those of skill in the art in view of FIG. 1, FIGS. 2(*a*) and 2(*b*), and other Bad sequences which can be obtained therewith.

For example and not limitation, a Bad polynucleotide can comprise the sequence [SEQ ID NO.:2]:

5'-ATGGGAACCCCAAAGCAGCCCTCGCTGGCTCCTGCACACGCCCTAGGCTTGAGGAAGTCC
GATCCCGGAATCCGGAGCCTGGGGAGCGACGCGGGAGGAAGGCGGTGGAGACCAGCAGCCCAG
AGTATGTTCCAGATCCCAGAGTTTGAGCCGAGTGAGCAGGAAGACGCTAGTGCTACAGATAGG
GGCCTGGGCCCTAGCCTCACTGAGGACCAGCCAGGTCCCTACCTGGCCCCAGGTCTCCTGGGG
AGCAACATTCATCAGCAGGGACGGGCAGCCACCAACAGTCATCATGGAGGCGCAGGGGCTATG
GAGACTCGGAGTCGCCACAGTTCGTACCCAGCGGGGACCGAGGAGGATGAAGGGATGGAGGAG
GAGCTTAGCCCTTTTCGAGGACGCTCGCGTTCGGCTCCCCCCAATCTCTGGGCAGCGCAGCGC
TACGGCCGTGAGCTCCGAAGGATGAGCGATGAGTTTGAGGGTTCCTTCAAGGGACTTCCTCGC
CCAAAGAGCGCAGGCACTGCAACACAGATGCGACAAAGCGCCGGCTGGACGCGCATTATCCAG
TCCTGGTGGGATCGAAACTTGGGCAAAGGAGGCTCCACCCCCTCCCAGTGA-3'.

a fusion protein. Typically, Bad polynucleotides comprise at least 25 consecutive nucleotides which are substantially identical to a naturally-occurring Bad sequence (e.g., FIG. 1), more usually Bad polynucleotides comprise at least 50 to 100 consecutive nucleotides which are substantially identical to a naturally-occurring Bad sequence. However, it will be recognized by those of skill that the minimum length of a Bad polynucleotide required for specific hybridization to a Bad target sequence will depend on several factors: G/C content, positioning of mismatched bases (if any), degree of uniqueness of the sequence as compared to the population of target polynucleotides, and chemical nature of the polynucleotide (e.g., methylphosphonate backbone, polyamide nucleic acid, phosphorothiolate, etc.), among others.

If desired, PCR amplimers for amplifying substantially full-length cDNA copies may be selected at the discretion of the practitioner. Similarly, amplimers to amplify single Bad exons or portions of the Bad gene (murine or human) may be selected.

Each of these sequences may be used as hybridization probes or PCR amplimers to detect the presence of Bad Also for example and not limitation, a Bad polynucleotide can comprise one or more sequences selected from the group consisting of:

5'-GGGAACCCCAAAGCAGCCCTCGCTG-3' [SEQ ID NO.:31];

5'-CACACGCCCTAGGCTTGAGGAAGTCC-3' [SEQ ID NO.:32];

5'-CGGAATCCGGAGCCTGGGGAGCG-3' [SEQ ID NO.:33];

5'-AGGAAGGCGGTGGAGACCAGCAGCCCAG-3' [SEQ ID NO.:34];

5'-AGTATGTTCCAGATCCCAGAGTTTGAGCC-3' [SEQ ID NO.:35];

5'-AGTGAGCAGGAAGACGCTAGTGCTACAGAT-3' [SEQ ID NO.:36];

5'-GCCTGGGCCCTAGCCTCACTGAGGAC-3' [SEQ ID NO.:37];

5'-CAGCCAGGTCCCTACCTGGCCCCAGGTCTC-3' [SEQ ID NO.:38];

5'-GCAACATTCATCAGCAGGGACGGGCAGCCA-3' [SEQ ID NO.:39];

5'-CAACAGTCATCATGGAGGCGCAGGGGCTATG-3' [SEQ ID NO.:40];
5'-GACTCGGAGTCGCCACAGTTCGTACCCAG-3' [SEQ ID NO.:41];
5'-CGGGGACCGAGGAGGATGAAGGGATGGAGGA-3' [SEQ ID NO.:42];
5'-AGCTTAGCCCTTTTCGAGGACGCTCGCGT-3' [SEQ ID NO.:43];
5'-GTTCGGCTC-CCCCCAATCTCTGGGCAGCGCAGCG-3' [SEQ ID NO.:44];
5'-ACGGCCGTGAGCTCCGAAGGATGAGCGATG-3' [SEQ ID NO.:45];
5'-GTTTGAGGGTTCCTTCAAGGGACTTCCTC-3' [SEQ ID NO.:46];
5'-CAAAGAGCGCAGGCACTGCAACACAGATG-3' [SEQ ID NO.:47];
5'-AGCGCCGGCTGGACGCGCATTATCCAG-3' [SEQ ID NO.:48];
5'-GCATTATCCAGTCCTGGTGGGATCGAAACTTG-3' [SEQ ID NO.:49]; and
5'-GGATCGAAACTTGGGCAAAGGAGGCTC-CACCCCCTCCCA-3' [SEQ ID NO.:50].

A preferred Bad polynucleotide comprises all of these sequences in the given order, with or without spacer polynucleotides between the given sequences. Non-coding sequences of a Bad polynucleotide, such as provided in FIG. 1 or equivalent non-mouse Bad polynucleotide, can also be used.

For example and not limitation, a Bad polynucleotide can comprise the nucleotide sequence shown in FIG. 1 (SEQ ID NO: 1).

For example, a human Bad cDNA and/or genomic clone can be identified and isolated from a human cDNA or genomic library, respectively, by hybridization of a labeled probe comprising the polynucleotide sequence of FIG. 1 and/or FIG. 2(*b*) or a pool of degenerate oligonucleotides encoding a segment of the polynucleotide sequence shown in FIG. 2(*a*). Suitable hybridization conditions for specific hybridization of these labeled probes to the human Bad cDNA or gene can be established empirically by performing a series of hybridizations and/or washing steps at several temperatures and/or ionic strength conditions; for example and not limitation, hybridization conditions comprising 50% formamide, 5×SSC or SSPE, 1–5×Denhardt's solution, 0.1–1% SDS, 100–200 μg sheared heterologous DNA or tRNA, 0–10% dextran sulfate, $1\times10^5$ to $1\times10^7$ cpm/ml of denatured probe with a specific activity of about $1\times10^8$ cpm/μg, and incubation at 42° C.–37° C. for about 6–36 hours is often a suitable initial point.

Transgenic Animal Embodiments

Genomic clones of Bad, particularly of the murine Bad gene, may be used to construct homologous targeting constructs for generating cells and transgenic nonhuman animals having at least one functionally disrupted Bad allele. Guidance for construction of homologous targeting constructs may be found in the art, including: Rahemtulla et al. (1991) *Nature* 353: 180; Jasin et al. (1990) *Genes Devel.* 4: 157; Koh et al. (1992) *Science* 256: 1210; Molina et al. (1992) *Nature* 357: 161; Grusby et al. (1991) *Science* 253: 1417; Bradley et al. (1992) *Bio/Technology* 10: 534, incorporated herein by reference). Homologous targeting can be used to generate so-called "knockout" mice, which are heterozygous or homozygous for an inactivated Lyar allele. Such mice may be sold commercially as research animals for investigation of immune system development, neoplasia, spermatogenesis, may be used as pets, may be used for animal protein (foodstuff), and other uses.

Chimeric targeted mice are derived according to Hogan, et al., *Manipulating the Mouse Embryo: A Laboratory Manual,* Cold Spring Harbor Laboratory (1988) and *Teratocarcinomas and Embryonic Stem Cells: A Practical Approach,* E. J. Robertson, ed., IRL Press, Washington, D.C., (1987) which are incorporated herein by reference. Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al. (1989) *Nature* 342:435; and Schwartzberg et al. (1989) *Science* 246: 799, each of which is incorporated herein by reference).

Additionally, a Bad cDNA or genomic gene copy may be used to construct transgenes for expressing Bad polypeptides at high levels and/or under the transcriptional control of transcription control sequences which do not naturally occur adjacent to the Bad gene. For example but not limitation, a constitutive promoter (e.g., a HSV-tk or pgk promoter) or a cell-lineage specific transcriptional regulatory sequence (e.g., a CD4 or CD8 gene promoter/enhancer) may be operably linked to a Bad-encoding polynucleotide sequence to form a transgene (typically in combination with a selectable marker such as a neo gene expression cassette). Such transgenes can be introduced into cells (e.g., ES cells, hematopoietic stem cells) and transgenic cells and transgenic nonhuman animals may be obtained according to conventional methods. Transgenic cells and/or transgenic nonhuman animals may be used to screen for antineoplastic agents and/or to screen for potential carcinogens, as overexpression of Lyar or inappropriate expression of Bad may result in a preneoplastic or neoplastic state.

Antisense Polynucleotides

Additional embodiments directed to modulation of neoplasia or apoptosis include methods that employ specific antisense polynucleotides complementary to all or part of the sequences shown in FIG. 1 or FIG. 2(*b*) or a cognate mammalian Bad sequence. Such complementary antisense polynucleotides may include nucleotide substitutions, additions, deletions, or transpositions, so long as specific hybridization to the relevant target sequence corresponding to FIG. 1 or FIG. 2(*b*) is retained as a functional property of the polynucleotide. Complementary antisense polynucleotides include soluble antisense RNA or DNA oligonucleotides which can hybridize specifically to Bad mRNA species and prevent transcription of the mRNA species and/or translation of the encoded polypeptide (Ching et al. (1989) *Proc. Natl. Acad. Sci. U.S.A.* 86: 10006; Broder et al. (1990) *Ann. Int. Med.* 113: 604; Loreau et al. (1990) *FEBS Letters* 274: 53; Holcenberg et al., WO91/11535; U.S. Ser. No. 07/530,165; WO91/09865; WO91/04753; WO90/13641; and EP 386563, each of which is incorporated herein by reference). The antisense polynucleotides therefore inhibit production of Bad polypeptides. Antisense polynucleotides that prevent transcription and/or translation of mRNA corresponding to Bad polypeptides may inhibit apoptosis, senescence, AIDS, and the like, and/or reverse the transformed phenotype of cells. Antisense polynucleotides of various lengths may be produced, although such antisense polynucleotides typically comprise a sequence of about at least 25 consecutive nucleotides which are substantially identical to a naturally-occurring Bad polynucleotide sequence, and typically which are identical to a sequence shown in FIG. 1 or FIG. 2(*b*) or a Bad sequence disclosed herein.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual. Alternatively, the antisense polynucleotides may comprise soluble oligonucleotides that are administered to the external milieu, either in the culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties. For general methods relating to antisense polynucleotides, see *Antisense RNA and DNA,* (1988), D. A. Melton, Ed., Cold Spring Harbor Laboratory, Cold Spring Harbor, N.Y.).

Production of Bax Polypeptides

The nucleotide and amino acid sequences shown in FIG. 1 and FIGS. 2(*a*) and 2(*b*) enable those of skill in the art to produce polypeptides corresponding to all or part of the full-length Bad polypeptide sequences. Such polypeptides may be produced in prokaryotic or eukaryotic host cells by expression of polynucleotides encoding Bad, or fragments and analogs thereof. Alternatively, such polypeptides may be synthesized by chemical methods or produced by in vitro translation systems using a polynucleotide template to direct translation. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y. and Berger and Kimmel, *Methods in Enzymology, Volume* 152, *Guide to Molecular Cloning Techniques* (1987), Academic Press, Inc., San Diego, Calif. Fragments or analogs of Bad may be prepared by those of skill in the art. Preferred amino- and carboxy-termini of fragments or analogs of Bad occur near boundaries of functional domains. For example, but not for limitation, such functional domains include domains conferring the property of binding to a bcl-2 or bcl-$x^L$ polypeptide, and/or (2) conserved domains (e.g. BH1 and BH2).

One method by which structural and functional domains may be identified is by comparison of the nucleotide and/or amino acid sequence data shown in FIGS. 1 and 2(*a*) to public or proprietary sequence databases. Preferably, computerized comparison methods are used to identify sequence motifs or predicted protein conformation domains that occur in other proteins of known structure and/or function, such as domain I (BH1) and domain II (BH2). For example, the NAD-binding domains of dehydrogenases, particularly lactate dehydrogenase and malate dehydrogenase, are similar in conformation and have amino acid sequences that are detectably homologous (*Proteins, Structures and Molecular Principles,* (1984) Creighton (ed.), W. H. Freeman and Company, New York, which is incorporated herein by reference). Further, a method to identify protein sequences that fold into a known three-dimensional structure are known (Bowie et al. (1991) *Science* 253: 164). Thus, the foregoing examples demonstrate that those of skill in the art can recognize sequence motifs and structural conformations that may be used to define structural and functional domains in the Bad sequences of the invention.

Additionally, computerized comparison of sequences shown in FIG. 1 or FIGS. 2(*a*) and 2(*b*) to existing sequence databases can identify sequence motifs and structural conformations found in other proteins or coding sequences that indicate similar domains of the Bad protein. For example but not for limitation, the programs GAP, BESTFIT, FASTA, and TFASTA in the Wisconsin Genetics Software Package (Genetics Computer Group, 575 Science Dr., Madison, Wis.) can be used to identify sequences in databases, such as GenBank/EMBL, that have regions of homology with a Bad sequences. Such homologous regions are candidate structural or functional domains. Alternatively, other algorithms are provided for identifying such domains from sequence data. Further, neural network methods, whether implemented in hardware or software, may be used to: (1) identify related protein sequences and nucleotide sequences, and (2) define structural or functional domains in Bad polypeptides (Brunak et al. (1991) *J. Mol. Biol.* 220: 49, which is incorporated herein by reference).

Fragments or analogs comprising substantially one or more functional domain may be fused to heterologous polypeptide sequences, wherein the resultant fusion protein exhibits the functional property(ies) conferred by the Bad fragment. Alternatively, Bad polypeptides wherein one or more functional domain have been deleted will exhibit a loss of the property normally conferred by the missing fragment.

By way of example and not limitation, the domain(s) conferring the property of binding to bcl-2 and/or bcl-$x^L$ may be fused to β-galactosidase to produce a fusion protein that can bind an immobilized bcl-2 and/or bcl-$x^L$ polypeptide in a binding reaction and which can enzymatically convert a chromogenic substrate to a chromophore.

Although one class of preferred embodiments are fragments having amino- and/or carboxy-termini corresponding to amino acid positions near functional domains borders, alternative Bad fragments may be prepared. The choice of the amino- and carboxy-termini of such fragments rests with the discretion of the practitioner and will be made based on experimental considerations such as ease of construction, stability to proteolysis, thermal stability, immunological reactivity, amino- or carboxyl-terminal residue modification, or other considerations.

In addition to fragments, analogs of Bad can be made. Such analogs may include one or more deletions or additions of amino acid sequence, either at the amino- or carboxy-termini, or internally, or both; analogs may further include sequence transpositions. Analogs may also comprise amino acid substitutions, preferably conservative substitutions. Additionally, analogs may include heterologous sequences generally linked at the amino- or carboxy-terminus, wherein the heterologous sequence(s) confer a functional property to the resultant analog which is not indigenous to the native Bad protein. However, Bad analogs must comprise a segment of 25 amino acids that has substantial similarity to a portion of the amino acid sequences shown in FIG. 1 or FIG. 2(*a*) or other mammalian Bad proteins, respectively, and which has at least one of the requisite functional properties (i.e., forms heterodimers with bcl-2 and/or forms homodimers with bcl-$x^L$. Preferred amino acid substitutions are those which: (1) reduce susceptibility to proteolysis, (2) reduce susceptibility to oxidation, (3) alter post-translational modification of the analog, possibly including phosphorylation, and (4) confer or modify other physicochemical or functional properties of such analogs. Bad analogs include various muteins of a Bad sequence other than the naturally-occurring peptide sequence. For example, single or multiple amino acid substitutions (preferably conservative amino acid substitutions) may be made in the naturally-occurring Bad sequence (preferably in the portion of the polypeptide outside domains I and II).

Conservative amino acid substitution is a substitution of an amino acid by a replacement amino acid which has similar characteristics (e.g., those with acidic properties: Asp and Glu). A conservative (or synonymous) amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles,* (1984) Creighton (ed.), W. H. Freeman and Company, New York; *Introduction to Protein Structure,* (1991), C. Branden and J. Tooze, Garland Publishing, New York, N.Y.; and Thornton et al. (1991) *Nature* 354: 105; which are incorporated herein by reference).

Similarly, full-length bcl-2 polypeptides and fragments, analogs, and/or fusions thereof can be made by those of skill in the art from the available bcl-2 gene, cDNA, and protein sequences (e.g., GenBank). A preferred bcl-2 polypeptide comprises:

-MAHAGRTGYDNREIVMKYIHYKLSQRGYEWDAGDVGAAPPGAAP
APGIFSSQPGHTPHPAASRDPVARTSPLQTPAAPGAAAGPALSP
VPPVVHLALRQAGDDFSRRYRGDFAEMSSQLHLTPFTARGRFAT
VVEELFRDGVNWGRIVAFFEFGGVMCVESVNREMSPLVDNIALW
MTEYLNRHLHTWIQDNGGWDAFVELYGPSMRPLFDFSWLSLKTL
LSLALVGACITLGAYLSHK- [SEQ ID NO.: 51]

or

-MAHAGRTGYDNREIVMKYIHYKLSQRGYEWDAGDVGAAPPGAAP
APGIFSSQPGHTPHPAASRDPVARTSPLQTPAAPGAAAGPALSP
VPPVVHLALRQAGDDFSRRYRGDFAEMSSQLHLTPFTARGRFAT
VVEELFRDGVNWGRIVAFFEFGGVMCVESVNREMSPLVDNIALW
MTEYLNRHLHTWIQDNGGWVGASGDVSLG- [SEQ ID NO.: 52]

Methods used to produce Bad polynucleotides and polypeptides can also be modified by those of skill in the art to produce bcl-2 and bcl-$x^L$ polypeptides. For example, a sequence of a human bcl-2 α protein is:

MAHAGRTGYDNREIVMKYIHYKLSQRGYEWDAGDVGAAPPGAAP
APGIFSSQPGHTPHPAASRDPVARTSPLQTPAAPGAAAGPALSP
VPPVVHLALRQAGDDFSRRYRGDFAEMSSQLHLTPFTARGRFAT
VVEELFRDGVNWGRIVAFFEFGGVMCVESVNREMSPLVDNIALW
MTEYLNRHLHTWIQDNGGWDAFVELYGPSMRPLFDFSWLSLKTL
LSLALVGACITLGAYLSHK. [SEQ ID NO.: 51]

A sequence of a human bcl-2 β protein is:

MAHAGRTGYDNREIVMKYIHYKLSQRGYEWDAGDVGAAPPGAAP
APGIFSSQPGHTPHPAASRDPVARTSPLQTPAAPGAAAGPALSP
VPPVVHLALRQAGDDFSRRYRGDFAEMSSQLHLTPFTARGRFAT
VVEELFRDGVNWGRIVAFFEFGGVMCVESVNREMSPLVDNIALW
MTEYLNRHLHTWIQDNGGWVGASGDVSLG. [SEQ ID NO.: 52]

Similarly, full-length bcl-$x^L$ polypeptides and fragments, analogs, and/or fusions thereof can be made by those of skill in the art from the available bcl-$x^L$ gene, cDNA, and protein sequences ( e.g. , GenBank ) . A preferred bcl-$x^L$ polypeptide comprises [SEQ ID NO.:59]:

-MSQSNRELVVDFLSYKLSQKGYSWSQFSDVEENRTEAPEGTESEMETPSAINGNPSWHLADS
PAVNGATGHSSSLDAREVIPMAAVKQALREAGDEFELRYRRAFSDLTSQLHITPGTAYQSFE
QVVNELFRDGVNWGRIVAFFSFGGALCVESVDKEMQVLVSRIAAWMATYLNDHLEPWIQENG
GWDTFVELYGNNAAAESRKGQERFNRWFLTGMTVAGVVLLGSLFSRK-.

Fusion proteins of bcl-$x^L$ and bcl-2 can be made, such as fusions with a GAL4 activation domain or DNA-binding domain, and the like.

Native Bad proteins, fragments thereof, or analogs thereof can be used as reagents in binding assays to detect binding to bcl-2 and/or bcl-$x^L$ for identifying agents that interfere with Bad and/or bcl-2 and/or bcl-$x^L$ function, said agents are thereby identified as candidate drugs which may be used, for example, to block apoptosis, to induce apoptosis (e.g., to treat lymphocytic leukemias, carcinomas, sarcomas, AIDS, neurodegenerative disease, senescence), and the like. Typically, in vitro binding assays that measure binding of Bad to bcl-2 or bcl-$x^L$ employ native Bad that contains domain I and domain II. The bcl-2, bcl-$x^L$, or Bad polypeptide is typically linked to a solid substrate by any of various means known to those of skill in the art; such linkage may be noncovalent (e.g., binding to a highly charged surface such as Nylon 66) or may be by covalent bonding (e.g., typically by chemical linkage). Bad polypeptides are typically labeled by incorporation of a radiolabeled amino acid or fluorescent label. The labeled Bad polypeptide is contacted with the immobilized bcl-2, bcl-$x^L$, or Bad polypeptide under aqueous conditions that permit specific binding in control binding reactions with a binding affinity of about $1\times10^5M^{-1}$ or greater (e.g., 10–250 mM NaCl or KCl and 5–100 mM Tris HCl pH 5–9, usually pH 6–8), generally including $Zn^{+2}$ and/or $Mn^{+2}$ and/or $Mg^{+2}$ in the nanomolar to micromolar range (1 nM to 999 μM). Specificity of binding is typically established by adding unlabeled competitor at various concentrations selected at the discretion of the practitioner. Examples of unlabeled protein competitors include, but are not limited to, the following: unlabeled Bad polypeptide, bovine serum albumin, and cellular protein extracts. Binding reactions wherein one or more agents are added are performed in parallel with a control binding reaction that does not include an agent. Agents which inhibit the specific binding of Bad polypeptides to bcl-2 polypeptides and/or bcl-$x^L$ polypeptides, as compared to a control reaction, are identified as candidate Bad-modulating drugs.

Methods used to produce Bax polynucleotides and polypeptides can also be modified by those of skill in the art to produce bcl-2 polypeptides. For example, a sequence of a human bcl-1 α protein is [SEQ ID NO.:51]:

MAHAGRTGYDNREIVMKYIHYKLSQRGYEWDAGDVGAAPPGAAP
APGIFSSQPGHTPHPAASRDPVARTSPLQTPAAPGAAAGPALSP
VPPVVHLALRQAGDDFSRRYRGDFAEMSSQLHLTPFTARGRFAT
VVEELFRDGVNWGRIVAFFEFGGVMCVESVNREMSPLVDNIALW
MTEYLNRHLHTWIQDNGGWDAFVELYGPSMRPLFDFSWLSLKTL
LSLALVGACITLGAYLSHK.

A sequence of a human bcl-2 β protein is [SEQ ID NO.:52]:

MAHAGRTGYDNREIVMKYIHYKLSQRGYEWDAGDVGAAPPGAAP
APGIFSSQPGHTPHPAASRDPVARTSPLQTPAAPGAAAGPALSP
VPPVVHLALRQAGDDFSRRYRGDFAEMSSQLHLTPFTARGRFAT
VVEELFRDGVNWGRIVAFFEFGGVMCVESVNREMSPLVDNIALW
MTEYLNRHLHTWIQDNGGWVGASGDVSLG.

A preferred bcl-$x^L$ polypeptide is [SEQ ID NO.:59]:

MSQSNRELVVDFLSYKLSQKGYSWSQFSDVEENRTEAPEGTESEMETPSAINGNPSWHLADS
PAVNGATGHSSSLDAREVIPMAAVKQALREAGDEFELRYRRAFSDLTSQLHITPGTAYQSFE
QVVNELFRDGVNWGRIVAFFSFGGALCVESVDKEMQVLVSRIAAWMATYLNDHLEPWIQENG
GWDTFVELYGNNAAAESRKGQERFNRWFLTGMTVAGVVLLGSLFSRK.

Other bcl-$x^L$, Bad, and bcl-2 polypeptides can be used.

Peptidomimetics

In addition to Bad, bcl-$x^L$, or bcl-2 polypeptides consisting only of naturally-occurring amino acids, Bad, bcl-$x^L$, or bcl-2 peptidomimetics are also provided. For example, peptidomimetics of the BH1 and/or BH2 domain of Bad, bcl-$x^L$, or bcl-2 can be suitable as drugs for inhibition of cell death repressor activity (i.e., to block bcl-2 and/or bcl-$x^L$ function).

Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p.392; and Evans et al. (1987) *J. Med. Chem* 30: 1229, which are incorporated herein by reference) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as human Bad, but have one or more peptide linkages optionally replaced by a linkage selected from the group consisting of: $—CH_2NH—$, $—CH_2S—$, $—CH_2—CH_2—$, $—CH{=}CH—$ (cis and trans), $—COCH_2—$, $—CH(OH)CH_2—$, and $—CH_2SO—$, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463–468 (general review); Hudson, D. et al., *Int J Pept Prot Res* (1979) 14:177–185 ($—CH_2NH—$, $CH_2CH_2—$); Spatola, A. F. et al., *Life Sci* (1986) 38:1243–1249 ($—CH_2—S$); Hann, M. M., *J Chem Soc Perkin Trans I* (1982) 307–314 ($—CH—CH—$, cis and trans); Almquist, R. G. et al., *J Med Chem* (1980) 23:1392–1398 ($—COCH_2—$); Jennings-White, C. et al., *Tetrahedron Lett* (1982) 23:2533 ($—COCH_2—$); Szelke, M. et al., European Appln. EP 45665 (1982) CA: 97:39405 (1982) ($—CH(OH)CH_2—$); Holladay, M. W. et al., *Tetrahedron Lett* (1983) 24:4401–4404 ($—C(OH)CH_2—$); and Hruby, V. J., *Life Sci* (1982) 31:189–199 ($—CH_2—S—$);

each of which is incorporated herein by reference. A particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labelling) of peptidomimetics should not substantially interfere with the desired biological or pharmacological activity of the peptidomimetic.

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) *Ann. Rev. Biochem.* 61: 387, incorporated herein by reference); for example, by adding internal cysteine residues capable of forming intramolecular disulfide bridges which cyclize the peptide. Cyclic peptides comprising a sequence of BH1 and/or BH2 frequently are preferred.

Another embodiment involves the formation of bcl-$x^L$ and Bad mutants wherein the native protein or fragment has at least one amino acid deleted or replaced by another amino acid and the mutants exhibits altered biological activity from the native protein or fragment.

The amino acid sequences of Bad polypeptides identified herein will enable those of skill in the art to produce polypeptides corresponding to Bad peptide sequences and sequence variants thereof. Such polypeptides may be produced in prokaryotic or eukaryotic host cells by expression of polynucleotides encoding a Bad peptide sequence, frequently as part of a larger polypeptide. Alternatively, such peptides may be synthesized by chemical methods. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y.; Berger and Kimmel, *Methods in Enzymology, Volume* 152, *Guide to Molecular Cloning Techniques* (1987) , Academic Press, Inc., San Diego, Calif.; Merrifield, J. (1969) *J. Am. Chem. Soc.* 91: 501; Chaiken I. M. (1981) *CRC Crit. Rev. Biochem.* 11: 255; Kaiser et al.(1989) *Science* 243: 187; Merrifield, B. (1986) *Science* 232: 342; Kent, S. B. H. (1988) *Ann. Rev. Biochem.* 57: 957; and Offord, R. E. (1980) Semisynthetic Proteins, Wiley Publishing, which are incorporated herein by reference).

Peptides comprising the sequence -PPNLWAAQRYGRELRRMSDEFEG- and/or -GWTRIIQSWWDRNTGK- and peptidomimetics thereof can be produced, typically by direct chemical synthesis or recombinant expression, and used as agents to competitively inhibit Bad/bcl-2 or Bad/bcl-$x^L$ heterodimer formation. The peptides are frequently produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal modifications such as amidation, as well as other terminal modifications, including cyclization, may be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Such peptides or peptidomimetics may be used therapeutically to treat disease by altering the process of apoptosis in a cell population of a patient.

Production and Applications of α-Bax Antibodies

Native Bad proteins, fragments thereof, or analogs thereof, may be used to immunize an animal for the production of specific antibodies. These antibodies may comprise a polyclonal antiserum or may comprise a monoclonal antibody produced by hybridoma cells. For general methods to prepare antibodies, see *Antibodies: A Laboratory Manual,* (1988) E. Harlow and D. Lane, Cold Spring Harbor Laboratory, Cold Spring Harbor, N.Y., which is incorporated herein by reference.

For example but not for limitation, a recombinantly produced fragment of Bad can be injected into a mouse along with an adjuvant following immunization protocols known to those of skill in the art so as to generate an immune response. Typically, approximately at least 1–50 μg of a Bad fragment or analog is used for the initial immunization, depending upon the length of the polypeptide. Alternatively or in combination with a recombinantly produced Bad polypeptide, a chemically synthesized peptide having a Bad sequence may be used as an immunogen to raise antibodies which bind a Bad protein, such as the native Bad polypeptide having the sequence shown essentially in FIG. 2(*a*), a native human Bad polypeptide, a polypeptide comprising a Bad epitope, or a Bad fusion protein. Immunoglobulins which bind the recombinant fragment with a binding affinity of at least $1\times10^7M^{-1}$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly-produced Bad polypeptide (or chemically synthesized Bad polypeptide) with an affinity of at least $1\times10^6M^{-1}$. Animals other than mice and rats may be used to raise antibodies; for example, goats, rabbits, sheep, and chickens may also be employed to raise antibodies reactive with a Bad protein. Transgenic mice having the capacity to produce substantially human antibodies also may be immunized and used for a source of α-Bad antiserum and/or for making monoclonal-secreting hybridomas.

Bacteriophage antibody display libraries may also be screened for binding to a Bad polypeptide, such as a full-length Bad protein, a Bad fragment, or a fusion protein comprising a Bad polypeptide sequence comprising a Bad epitope (generally at least 3–5 contiguous amino acids).

Generally such Bad peptides and the fusion protein portions consisting of Bad sequences for screening antibody libraries comprise about at least 3 to 5 contiguous amino acids of Bad, frequently at least 7 contiguous amino acids of Bad, usually comprise at least 10 contiguous amino acids of Bad, and most usually comprise a Bad sequence of at least 14 contiguous amino acids as shown in FIG. 1 or FIG. 2(*a*).

Combinatorial libraries of antibodies have been generated in bacteriophage lambda expression systems which may be screened as bacteriophage plaques or as colonies of lysogens (Huse et al. (1989) *Science* 246: 1275; Caton and Koprowski (1990) *Proc. Natl. Acad. Sci.* (*U.S.A.*) 87: 6450; Mullinax et al (1990) *Proc. Natl. Acad. Sci.* (*U.S.A.*) 87: 8095; Persson et al. (1991) *Proc. Natl. Acad. Sci.* (*U.S.A.*) 88: 2432). Various embodiments of bacteriophage antibody display libraries and lambda phage expression libraries have been described (Kang et al. (1991) *Proc. Natl. Acad. Sci.* (*U.S.A.*) 88: 4363; Clackson et al. (1991) *Nature* 352: 624; McCafferty et al. (1990) *Nature* 348: 552; Burton et al. (1991) *Proc. Natl. Acad. Sci.* (*U.S.A.*) 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci.* (*U.S.A.*) 89: 4457; Hawkins and Winter (1992) *J. Immunol.* 22: 867; Marks et al. (1992) *Biotechnology* 10: 779; Marks et al. (1992) *J. Biol. Chem.* 267: 16007; Lowman et al (1991) *Biochemistry* 30: 10832; Lerner et al. (1992) *Science* 258: 1313, incorporated herein by reference). Typically, a bacteriophage antibody display library is screened with a Bad polypeptide that is immobilized (e.g., by covalent linkage to a chromatography resin to enrich for reactive phage by affinity chromatography) and/or labeled (e.g., to screen plaque or colony lifts).

Bad polypeptides which are useful as immunogens, for diagnostic detection of α-Bad antibodies in a sample, for diagnostic detection and quantitation of Bad protein in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other proteins of humans, mice, or other contaminants.

For some applications of these antibodies, such as identifying immunocrossreactive proteins, the desired antiserum or monoclonal antibody(ies) is/are not monospecific. In these instances, it may be preferable to use a synthetic or recombinant fragment of Bad as an antigen rather than using the entire native protein. More specifically, where the object is to identify immunocrossreactive polypeptides that comprise a particular structural moiety, such as a bcl-2-binding domain or bcl-$x^L$-binding domain, it is preferable to use as an antigen a fragment corresponding to part or all of a commensurate structural domain in the Bad protein, often a BH1 or BH2 domain. Production of recombinant or synthetic fragments having such defined amino- and carboxy-termini is provided by the Bad sequences shown in FIG. 1 and FIG. 2(*a*).

If an antiserum is raised to a Bad fusion polypeptide, such as a fusion protein comprising a Bad immunogenic epitope fused to β-galactosidase or glutathione S-transferase, the antiserum is preferably preadsorbed with the non-Bad fusion partner (e.g, β-galactosidase or glutathione S-transferase) to deplete the antiserum of antibodies that react (i.e., specifically bind to) the non-Bad portion of the fusion protein that serves as the immunogen. Monoclonal or polyclonal antibodies which bind to the human and/or murine Bad protein can be used to detect the presence of human or murine Bad polypeptides in a sample, such as a Western blot of denatured protein (e.g., a nitrocellulose blot of an SDS-PAGE) obtained from a lymphocyte sample of a patient. Preferably quantitative detection is performed, such as by denistometric scanning and signal integration of a Western blot. The monoclonal or polyclonal antibodies will bind to the denatured Bad epitopes and may be identified visually or by other optical means with a labeled second antibody or labeled *Staphylococcus aureus* protein A by methods known in the art.

One use of such antibodies is to screen cDNA expression libraries, preferably containing cDNA derived from human or murine mRNA from various tissues, for identifying clones containing cDNA inserts which encode structurally-related, immunocrossreactive proteins, that are candidate novel Bad binding factors or Bad-related proteins. Such screening of cDNA expression libraries is well known in the art, and is further described in Young et al., *Proc. Natl. Acad. Sci. U.S.A.* 80:1194–1198 (1983), which is incorporated herein by reference) as well as other published sources. Another use of such antibodies is to identify and/or purify immunocrossreactive proteins that are structurally or evolutionarily related to the native Bad protein or to the corresponding Bad fragment (e.g., functional domain; bcl-2-binding domain; bcl-$x^L$-binding domain) used to generate the antibody. The anti-Bad antibodies of the invention can be used to measure levels of Bad protein in a cell or cell population, for example in a cell explant (e.g., lymphocyte sample) obtained from a patient. When used in conjunction with antibodies that specifically bind to bcl-2 or bcl-$x^L$, the anti-Bad antibodies of the present invention can be used to measure the ratio of Bad protein to bcl-2 or bcl-$x^L$ protein (i.e., indirectly Bax:bcl-2 ratio or Bax:bcl-$x^L$ ratio) in a cell or cell population. The anti-Bad, anti-bcl-$x^L$ and anti-bcl-2 antibodies can be used to measure the corresponding protein levels (Bad, bcl-$x^L$, or bcl-2, respectively) by various methods, including but not limited to: (1) standardized ELISA on cell extracts, (2) immunoprecipitation of cell extracts followed by polyacrylamide gel electrophoresis of the immunoprecipitated products and quantitative detection of the band(s) corresponding to Bad and/or bcl-2 and/or bcl-$x^L$, and (3) in situ detection by immunohistochemical straining with the anti-Bad and/or anti-bcl-2 and/or anti-bcl-$x^L$ antibodies and detection with a labeled second antibody. The measurement of the Bad:bcl-2 or Bad:bcl-$x^L$ ratio in a cell or cell population is informative regarding the apoptosis status of the cell or cell population.

Various other uses of such antibodies are to diagnose and/or stage leukemias or other neoplasms, and for therapeutic application (e.g., as cationized antibodies or by targeted liposomal delivery) to treat neoplasia, autoimmune disease, AIDS, and the like.

An antiserum which can be utilized for this purpose can be obtained by conventional procedures. One exemplary procedure involves the immunization of a mammal, such as rabbits, which induces the formation of polyclonal antibodies against Bad. Monoclonal antibodies are also being generated from already immunized hamsters. This antibody can be used to detect the presence and level of the Bad protein.

It is also possible to use the proteins for the immunological detection of Bad, bcl-$x^L$, bcl-2 and associations thereof with standard assays as well as assays using markers, which are radioimmunoassays or enzyme immunoassays.

The detection and determination of Bad and/or bcl-2 and/or bcl-$x^L$ has significant diagnostic importance. For example, the detection of proteins favoring death effector molecules would be advantageous in cancer therapy and controlling hypertrophies and eliminating self reactive clones in autoimmunity. The detection or determination of proteins favoring death repressor molecules will be beneficial in immunodeficiency disease, including HIV-I, II and III, and in neurodegenerative and ischemic cell death. Thus these proteins and their antibodies can be employed as a marker to monitor, check or detect the course of disease.

More particularly, the protein Bad may be used for performing immunochemical methods for the detection and determination of the protein or its associated protein bcl-2 and bcl-$x^L$, in order to monitor cell growth or to detect or monitor the course of diseases. It can also be used as a method for the treatment of a neurodegenerative disease, or immunodeficiency, or an ischemia induced injury such as myocardial infarction and neurologic stroke, which comprises; administering an effective amount of a compound to a patient to regulate the ratio of bcl-2 to Bad or bcl-$x^L$ to Bad to promote the survival of cells by generating an excess of bcl-2 (i.e., an agent which binds to Bad and prevents it from sequestering bcl-$x^L$ or bcl-2) or to promote apoptosis and cell death by sequestering bcl-$x^L$ or bcl-2 and thereby increasing the amount of free Bad and/or Bad:Bad homomultimers.

Cross-linked complexes of Bad:bcl-$x^L$ and/or Bad:bcl-2 can be used as immunogens, and the resultant antisera preadsorbed with Bad, bcl-$x^L$, and bcl-2 such that the remaining antisera comprises antibodies which bind conformational epitopes present on the complexes but not the monomers (e.g., complex-specific epitopes). Complex-specific hybridomas and monoclonal antibodies can be similarly generated. Such antibodies can be used diagnostically to detect and quantitate the presence of specific complexes and correlate this data with disease or cell type, and the like.

Identification and Isolation of Proteins That Bind Bad

Proteins that bind to Bad and/or a Bad:bcl-$x^L$ complex and/or Bad:bcl-2 complex are potentially important regulatory proteins. Such proteins may be targets for novel antineoplastic agents or anti-inflammatory agents, immunomodulatory agents, and the like. These proteins are referred to herein as accessory proteins. Accessory proteins may be isolated by various methods known in the art.

One preferred method of isolating accessory proteins is by contacting a Bad polypeptide to an antibody that binds the Bad polypeptide, and isolating resultant immune complexes. These immune complexes may contain accessory proteins bound to the Bad polypeptide. The accessory proteins may be identified and isolated by denaturing the immune complexes with a denaturing agent and, preferably, a reducing agent. The denatured, and preferably reduced, proteins can be electrophoresed on a polyacrylamide gel. Putative accessory proteins can be identified on the polyacrylamide gel by one or more of various well known methods (e.g., Coomassie staining, Western blotting, silver staining, etc.), and isolated by resection of a portion of the polyacrylamide gel containing the relevant identified polypeptide and elution of the polypeptide from the gel portion.

A putative accessory protein may be identified as an accessory protein by demonstration that the protein binds to Bad and/or a Bad:bcl-$x^L$ complex and/or a Bad:bcl-2 complex. Such binding may be shown in vitro by various means, including, but not limited to, binding assays employing a putative accessory protein that has been renatured subsequent to isolation by a polyacrylamide gel electrophoresis method. Alternatively, binding assays employing recombinant or chemically synthesized putative accessory protein may be used. For example, a putative accessory protein may be isolated and all or part of its amino acid sequence determined by chemical sequencing, such as Edman degradation. The amino acid sequence information may be used to chemically synthesize the putative accessory protein. The amino acid sequence may also be used to produce a recombinant putative accessory protein by: (1) isolating a cDNA clone encoding the putative accessory protein by screening a cDNA library with degenerate oligonucleotide probes according to the amino acid sequence data, (2) expressing the cDNA in a host cell, and (3) isolating the putative accessory protein. Alternatively, a polynucleotide encoding a Bad polypeptide may be constructed by oligonucleotide synthesis, placed in an expression vector, and expressed in a host cell.

Putative accessory proteins that bind Bad and/or Bad complexes in vitro are identified as accessory proteins. Accessory proteins may also be identified by crosslinking in vivo with bifunctional crosslinking reagents (e.g., dimethylsuberimidate, glutaraldehyde, etc.) and subsequent isolation of crosslinked products that include a Bad polypeptide. For a general discussion of cross-linking, see Kunkel et al. (1981) *Mol. Cell. Biochem.* 34: 3, which is incorporated herein by reference. Preferably, the bifunctional crosslinking reagent will produce crosslinks which may be reversed under specific conditions after isolation of the crosslinked complex so as to facilitate isolation of the accessory protein from the Lyar polypeptide. Isolation of crosslinked complexes that include a Lyar polypeptide is preferably accomplished by binding an antibody that binds a Bad polypeptide with an affinity of at least $1\times10^7 M^{-1}$ to a population of crosslinked complexes and recovering only those complexes that bind to the antibody with an affinity of at least $1\times10^7 M^{-1}$. Polypeptides that are crosslinked to a Bad polypeptide are identified as accessory proteins.

Also, an expression library, such as a λgt11 cDNA expression library (Dunn et al. (1989) *J. Biol. Chem.* 264: 13057), can be screened with a labelled Bad polypeptide to identify cDNAs encoding polypeptides which specifically bind to the Bad polypeptide. For these procedures, cDNA libraries usually comprise mammalian cDNA populations, typically human, mouse, or rat, and may represent cDNA produced from RNA of one cell type, tissue, or organ and one or more developmental stage. Specific binding for screening cDNA expression libraries is usually provided by including one or more blocking agent (e.g., albumin, nonfat dry milk solids, etc.) prior to and/or concomitant with contacting the labeled Bad polypeptide (and/or labeled anti-Bad antibody).

Screening assays can be developed for identifying candidate antineoplastic agents as being agents which inhibit binding of Bad to an accessory protein under suitable binding conditions.

Yeast Two-Hybrid Screening Assays

An approach to identifying polypeptide sequences which bind to a predetermined polypeptide sequence has been to use a so-called "two-hybrid" system wherein the predetermined polypeptide sequence is present in a fusion protein (Chien et al. (1991) *Proc. Natl. Acad. Sci.* (*USA*) 88: 9578). This approach identifies protein-protein interactions in vivo through reconstitution of a transcriptional activator (Fields S. and Song O. (1989) *Nature* 340: 245), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3) which is operably linked to a Gal4 binding site. Typically, the two-hybrid method is used to identify novel polypeptide sequences which interact with a known protein (Silver S. C. and Hunt S. W. (1993) *Mol. Biol. Rep.* 17: 155; Durfee et al. (1993) *Genes Devel.* 7; 555; Yang et al. (1992) *Science* 257: 680; Luban et al. (1993) *Cell* 73: 1067; Hardy et al. (1992) *Genes Devel.* 6; 801; Bartel et al. (1993) *Biotechniques* 14: 920; and Vojtek et al. (1993) *Cell* 74: 205). However, variations of the two-hybrid method have been used to identify mutations of a known protein that affect its binding to a second known protein (Li B. and Fields S. (1993) *FASEB J.* 2: 957; Lalo et al. (1993) *Proc. Natl. Acad. Sci.* (*USA*) 90: 5524; Jackson et al. (1993) *Mol. Cell. Biol.* 13; 2899; and Madura et al. (1993) *J. Biol. Chem.* 268: 12046). Two-hybrid systems have also been used to identify interacting structural domains of two known proteins (Bardwell et al. (1993) *med. Microbiol.* 8: 1177; Chakraborty et al. (1992) *J. Biol. Chem.* 267: 17498; Staudinger et al. (1993) *J. Biol. Chem.* 268: 4608; and Milne G. T. and Weaver D. T. (1993) *Genes Devel.* 7; 1755) or domains responsible for oligomerization of a single protein (Iwabuchi et al. (1993) *Oncogene* 8; 1693; Bogerd et al. (1993) *J. Virol.* 67: 5030). Variations of two-hybrid systems have been used to study the in vivo activity of a proteolytic enzyme (Dasmahapatra et al. (1992) *Proc. Natl. Acad. Sci.* (*USA*) 89: 4159). Alternatively, an *E. coli*/BCCP interactive screening system (Germino et al. (1993) *Proc. Natl. Acad. Sci.* (*U.S.A.*) 90: 933; Guarente L (1993) *Proc. Natl. Acad. Sci.* (*U.S.A.*) 90: 1639) can be used to identify interacting protein sequences (i.e., protein sequences which heterodimerize or form higher order heteromultimers).

Each of these two-hybrid methods rely upon a positive association between two Gal4 fusion proteins thereby reconstituting a functional Gal4 transcriptional activator which then induces transcription of a reporter gene operably linked to a Gal4 binding site. Transcription of the reporter gene produces a positive readout, typically manifested either (1) as an enzyme activity (e.g., β-galactosidase) that can be identified by a colorimetric enzyme assay or (2) as enhanced cell growth on a defined medium (e.g., HIS3). A positive readout condition is generally identified as one or more of the following detectable conditions: (1) an increased transcription rate of a predetermined reporter gene, (2) an increased concentration or abundance of a polypeptide product encoded by a predetermined reporter gene, typically such as an enzyme which can be readily assayed in vivo, and/or (3) a selectable or otherwise identifiable phenotypic change in an organism (e.g., yeast) harboring the reverse two-hybrid system. Generally, a selectable or otherwise identifiable phenotypic change that characterizes a positive readout condition confers upon the organism either: a selective growth advantage on a defined medium, a mating phenotype, a characteristic morphology or developmental stage, drug resistance, or a detectable enzymatic activity (e.g., β-galactosidase, luciferase, alkaline phosphatase, and the like).

Transcriptional activators are proteins that positively regulate the expression of specific genes. They can be functionally dissected into two structural domains: one region that binds to specific DNA sequences and thereby confers specificity, and another region termed the activation domain that binds to protein components of the basal gene expression machinery (Ma and Ptashne (1988) *Cell* 55: 443). These two domains need to be physically connected in order to function as a transcriptional activator. Two-hybrid systems exploit this finding by hooking up an isolated DNA binding domain to one protein (protein X), while hooking up the isolated activation domain to another protein (protein Y). When X and Y interact to a significant extent, the DNA binding and activation domains will now be connected and the transcriptional activator function reconstituted (Fields and Song (1989) *Nature* 340: 245). The yeast host strain is engineered so that the reconstituted transcriptional activator drives the expression of a specific reporter gene such as HIS3 or lacZ, which provides the read-out for the protein-protein interaction (Field and Song (1989) op.cit.; Chein et al. (1991) op.cit.). One advantage of two-hybrid systems for monitoring protein-protein interactions is their sensitivity in detection of physically weak, but physiologically important, protein-protein interactions. As such it offers a significant advantage over other methods for detecting protein-protein interactions (e.g., ELISA assay).

The invention also provides host organisms (typically unicellular organisms) which harbor a Bad protein two-hybrid system, typically in the form of polynucleotides encoding a first hybrid protein, a second hybrid protein, and a reporter gene, wherein said polynucleotide(s) are either stably replicated or introduced for transient expression. In an embodiment, the host organism is a yeast cell (e.g., *Saccharomyces cervisiae*) and in which the reporter gene transcriptional regulatory sequence comprises a Gal4-responsive promoter.

Yeast comprising (1) an expression cassette encoding a GAL4 DNA binding domain (or GAL4 activator domain) fused to a binding fragment of Bad capable of binding to a bcl-$x^L$ and/or bcl-2 polypeptide, (2) an expression cassette encoding a GAL4 DNA activator domain (or GAL4 binding domain, respectively) fused to a member of a cDNA library or a binding fragment of bcl-$x^L$ or bcl-2 capable of binding to a Bad polypeptide, and (3) a reporter gene (e.g., β-galactosidase) comprising a cis-linked GAL4 transcriptional response element can be used for agent screening. Such yeast are incubated with a test agent and expression of the reporter gene (e.g., β-galactosidase) is determined; the capacity of the agent to inhibit expression of the reporter gene as compared to a control culture identifies the agent as a candidate Bad modulatory agent.

Yeast two-hybrid systems may be used to screen a mammalian (typically human) cDNA expression library, wherein cDNA is fused to a GAL4 DNA binding domain or activator domain, and either a Bad, bcl-$x^L$, or bcl-2 polypeptide sequence is fused to a GAL4 activator domain or DNA binding domain, respectively. Such a yeast two-hybrid system can screen for cDNAs that encode proteins which bind to Bad, bcl-$x^L$, or bcl-2 sequences. For example, a cDNA library can be produced from mRNA from a human mature B cell (Namalwa) line (Ambrus et al. (1993) *Proc. Natl. Acad. Sci.* (*U.S.A.*) or other suitable cell type. Such a cDNA library cloned in a yeast two-hybrid expression system (Chien et al. (1991) *Proc. Natl. Acad. Sci.* (*U.S.A.*) 88: 9578) can be used to identify cDNAs which encode proteins that interact with Bad, bcl-$x^L$, or bcl-2 and thereby produce expression of the GAL4-dependent reporter gene. Polypeptides which interact with Bad, bcl-$x^L$, or bcl-2 can also be identified by immunoprecipitation of Bad, bcl-$x^L$, or bcl-2 with antibody and identification of co-precipitating species.

Further, polypeptides that bind Bad, bcl-$x^L$, or bcl-2 can be identified by screening a peptide library (e.g., a bacteriophage peptide display library, a spatially defined VLSIPS peptide array, and the like) with a Bad, bcl-$x^L$, or bcl-2 polypeptide.

The invention also provides a kit comprising a two-hybrid system having (1) a first hybrid protein comprising a Bad polypeptide and a transcriptional activator activation domain, (2) a second hybrid protein comprising a bcl-$x^L$ or bcl-2 polypeptide and a transcriptional activator DNA-binding domain, a host cell, and an instruction manual. Alternatively, the Bad polypeptide may be fused to the DNA-binding domain and the bcl-$x^L$ or bcl-2 polypeptide used to the activation domains. Such kits may optionally include a panel of agents for testing for the capacity to alter intermolecular binding between the first and second hybrid proteins.

Methods of Identifying Novel and Apoptosis-Modulating Agents

A basis of the present invention is the experimental finding that a novel protein, Bad, is present in many cell types which undergo apoptosis and Bad binds specifically to bcl-$x^L$ and less avidly to bcl-2, proteins known to modulate (inhibit) apoptosis in cells. For example, agents which block Bad function and/or block bcl-2 function and/or block bcl-$x^L$ function may be developed as potential human therapeutic drugs.

Therapeutic agents which inhibit cell death by modulating Bad function (i.e., sequestration of bcl-2 and/or bcl-$x^L$ and enhancement of formation of Bax/Bax homodimers and free Bax and/or induction of apoptosis), for example by augmenting formation of bcl-2/Bax heteromultimers or bcl-$x^L$:Bax heteromultimers and thereby reducing formation of Bax:Bax homomultimers, or by sequestering bcl-$x^L$ and/or bcl-2 and enhancing the relative amount of unbound Bax and/or Bax:Bax homomultimers can be used as pharmaceuticals. Such pharmaceuticals will be used to treat a variety of human and veterinary diseases, such as: reperfusion injury, myocardial infarction, stroke, traumatic brain injury, neurodegenerative diseases, aging, ischemia, toxemia, infection, neoplasia, hyperplasia, AIDS, hepatitis, and the like.

Therapeutic agents which augment (induce) cell death by modulating the levels of Bad:bcl-2 heteromultimers and/or Bad:bcl-$x^L$ heteromultimers and thereby affect the level of Bax/Bax homomultimers can be used as pharmaceuticals. Such pharmaceuticals can be used to treat a variety of diseases including but not limited to: hyperplasia, neoplasia, autoimmune diseases, transplant rejection, lymphoproliferative diseases, and the like.

Bad-modulating agents which enhance the death repressor activity of bcl-$x^L$ or bcl-2 (e.g., by competitively inhibiting endogenous naturally-occurring Bad from sequestering bcl-$x^L$ or bcl-2) are candidate antineoplastic agents. Candidate antineoplastic agents are then tested further for antineoplastic activity in assays which are routinely used to predict suitability for use as human antineoplastic drugs. Examples of these assays include, but are not limited to: (1) ability of the candidate agent to inhibit the ability of anchorage-independent transformed cells to grow in soft agar, (2) ability to reduce tumorigenicity of transformed cells transplanted into nu/nu mice, (3) ability to reverse morphological transformation of transformed cells, (4) ability to reduce growth of transplanted tumors in nu/nu mice, (5) ability to inhibit formation of tumors or preneoplastic cells in animal models of spontaneous or chemically-induced carcinogenesis, and (6) ability to induce a more differentiated phenotype in transformed cells to which the agent is applied.

Bad:bcl-2 and Bad:bcl-$x^L$ Intermolecular Binding

A basis of the present invention is the surprising finding that the Bad protein forms a complex with the bcl-2 and/or bcl-$x^L$ protein under physiological conditions. This finding indicates that the Bad protein serves as a modulator of bcl-2 and/or bcl-$x^L$ function, and indirectly Bax function. Such functional modulation can serve to couple a signal transduction pathway (via Bad) to an apoptosis regulatory protein (i.e., bcl-2, bcl-$x^L$, and Bax).

Assays for detecting the ability of agents to inhibit or augment the binding of Bad to bcl-2 or bcl-$x^L$ provide for facile high-throughput screening of agent banks (e.g., compound libraries, peptide libraries, and the like) to identify Bad or bcl-2 or bcl-$x^L$ antagonists or agonists. Such Bad or bcl-2 or bcl-$x^L$ antagonists and agonists may modulate Bad and/or bcl-2 and/or bcl-$x^L$ and/or Bax activity and thereby modulate apoptosis.

Administration of an efficacious dose of an agent capable of specifically inhibiting Bad:bcl-2 or Bad:bcl-$x^L$ complex formation to a patient can be used as a therapeutic or prophylactic method for treating pathological conditions (e.g., cancer, inflammation, lymphoproliferative diseases, autoimmune disease, neurodegenerative diseases, and the like) which are effectively treated by modulating Bad and/or bcl-2 and/or bcl-$x^L$ activity and apoptosis.

Binding assays generally take one of two forms: immobilized Bad polypeptide(s) can be used to bind labeled bcl-2 or bcl-$x^L$ polypeptide(s), or conversely, immobilized bcl-2 or bcl-$x^L$ polypeptide(s) can be used to bind labeled Bad polypeptides. In each case, the labeled polypeptide is contacted with the immobilized polypeptide under aqueous conditions that permit specific binding of the polypeptides(s) to form a Bad:bcl-2 complex or Bad:bcl-xL complex in the absence of added agent. Particular aqueous conditions may be selected by the practitioner according to conventional methods. For general guidance, the following buffered aqueous conditions may be used: 10–250 mM NaCl, 5–50 mM Tris HCl, pH 5–8, with optional addition of divalent cation(s) and/or metal chelators and/or nonionic detergents and/or membrane fractions. It is appreciated by those in the art that additions, deletions, modifications (such as pH) and substitutions (such as KCl substituting for NaCl or buffer substitution) may be made to these basic conditions. Modifications can be made to the basic binding reaction conditions so long as specific binding of Bad polypeptide(s) to bcl-2 or bcl-$x^L$ polypeptides occurs in the control reaction(s). Conditions that do not permit specific binding in control reactions (no agent included) are not suitable for use in binding assays.

In some embodiments, the assay detects the formation of Bax:Bax homomultimers in the presence of bcl-$x^L$ or bcl-2 and Bad, and the assay identifies agents which reduce the capacity, efficacy, or potency of Bad to inhibit bcl-$x^L$ or bcl-2 to act as a death repressor by inhibiting formation of Bax:Bax homomultimers. Modifications can be made to the basic binding reaction conditions so long as specific binding of a Bax polypeptide to a Bax polypeptide and binding of a Bad polypeptide to a bcl-$x^L$ polypeptide or bcl-2 polypeptide occurs in the control reaction(s) (i.e., without agent).

Preferably, at least one polypeptide species is labeled with a detectable marker. Suitable labeling includes, but is not limited to, radiolabeling by incorporation of a radiolabeled amino acid (e.g., $^{14}$C-labeled leucine, $^{3}$H-labeled glycine, $^{35}$S-labeled methionine), radiolabeling by post-translational radioiodination with $^{125}$I or $^{131}$I (e.g., Bolton-Hunter reaction and chloramine T), labeling by post-translational phosphorylation with $^{32}$P (e.g., phosphorylase and inorganic radiolabeled phosphate) fluorescent labeling by incorporation of a fluorescent label (e.g., fluorescein or rhodamine), or labeling by other conventional methods known in the art. In embodiments where one of the polypeptide species is immobilized by linkage to a substrate, the other polypeptide is generally labeled with a detectable marker.

Additionally, in some embodiments a Bad or bcl-2 or bcl-$x^L$ polypeptide may be used in combination with an accessory protein (e.g., a protein which forms a complex with the polypeptide in vivo), it is preferred that different labels are used for each polypeptide species, so that binding of individual and/or heterodimeric and/or multimeric complexes can be distinguished. For example but not limitation, a Bad polypeptide may be labeled with fluorescein and an accessory polypeptide may be labeled with a fluorescent marker that fluorescesces with either a different excitation wavelength or emission wavelength, or both. Alternatively, double-label scintillation counting may be used, wherein a Bad polypeptide is labeled with one isotope (e.g., $^{3}$H) and a second polypeptide species is labeled with a different isotope (e.g., $^{14}$C) that can be distinguished by scintillation counting using discrimination techniques.

Labeled polypeptide(s) are contacted with immobilized polypeptide(s) under aqueous conditions as described herein. The time and temperature of incubation of a binding reaction may be varied, so long as the selected conditions permit specific binding to occur in a control reaction where no agent is present. Preferable embodiments employ a reaction temperature of about at least 15 degrees Centigrade, more preferably 35 to 42 degrees Centigrade, and a time of incubation of approximately at least 15 seconds, although longer incubation periods are preferable so that, in some embodiments, a binding equilibrium is attained. Binding kinetics and the thermodynamic stability of bound Bad:bcl-2 or Bad:bcl-$x^L$ complexes determine the latitude available for varying the time, temperature, salt, pH, and other reaction conditions. However, for any particular embodiment, desired binding reaction conditions can be calibrated readily by the practitioner using conventional methods in the art, which may include binding analysis using Scatchard analysis, Hill analysis, and other methods (*Proteins, Structures and Molecular Principles,* (1984) Creighton (ed.), W. H. Freeman and Company, New York).

Specific binding of labeled Bad or bcl-2 polypeptide to immobilized bcl-2 or Bad polypeptide, respectively, is determined by including unlabeled competitor protein(s) (e.g., albumin). Similarly, specific binding of labeled Bad or bcl-$x^L$ polypeptide to immobilized bcl-$x^L$ or Bad polypeptide, respectively, is determined by including unlabeled competitor protein(s) (e.g., albumin). After a binding reaction is completed, labeled polypeptide(s) that is/are specifically bound to immobilized polypeptide is detected. For example and not for limitation, after a suitable incubation period for binding, the aqueous phase containing non-immobilized protein is removed and the substrate containing the immobilized polypeptide species and any labeled protein bound to it is washed with a suitable buffer, optionally containing unlabeled blocking agent(s), and the wash buffer(s) removed. After washing, the amount of detectable label remaining specifically bound to the immobilized polypeptide is determined (e.g., by optical, enzymatic, autoradiographic, or other radiochemical methods).

In some embodiments, addition of unlabeled blocking agents that inhibit non-specific binding are included. Examples of such blocking agents include, but are not limited to, the following: calf thymus DNA, salmon sperm DNA, yeast RNA, mixed sequence (random or pseudorandom sequence) oligonucleotides of various lengths, bovine serum albumin, nonionic detergents (NP-40, Tween, Triton X-100, etc.), nonfat dry milk proteins, Denhardt's reagent, polyvinylpyrrolidone, Ficoll, and other blocking agents. Practitioners may, in their discretion, select blocking agents at suitable concentrations to be included in binding assays; however, reaction conditions are selected so as to permit specific binding between a Bad polypeptide and a bcl-2 or bcl-$x^L$ polypeptide in a control binding reaction. Blocking agents are included to inhibit nonspecific binding of labeled protein to immobilized protein and/or to inhibit nonspecific binding of labeled polypeptide to the immobilization substrate.

In embodiments where a polypeptide is immobilized, covalent or noncovalent linkage to a substrate may be used. Covalent linkage chemistries include, but are not limited to, well-characterized methods known in the art (Kadonaga and Tijan (1986) *Proc. Natl. Acad. Sci.* (*U.S.A.*) 83: 5889). One example, not for limitation, is covalent linkage to a substrate derivatized with cyanogen bromide (such as CNBr-derivatized Sepharose 4B). It may be desirable to use a spacer to reduce potential steric hindrance from the substrate. Non-covalent bonding of proteins to a substrate include, but are not limited to, bonding of the protein to a charged surface and binding with specific antibodies.

In one class of embodiments, parallel binding reactions are conducted, wherein one set of reactions serves as control and at least one other set of reactions include various quantities of agents, mixtures of agents, or biological extracts, that are being tested for the capacity to inhibit binding of a Bad polypeptide to a bcl-2 or bcl-$x^L$ polypeptide, and/or to inhibit binding of a Bax polypeptide to form homomultimers (homodimers) with a Bax polypeptide. Agents which, when added to a binding reaction, inhibit formation of Bad:bcl-$x^L$ and/or Bad:bcl-2 complexes (and thus reduce formation of Bax:Bax complexes or free Bax, if present) are thereby identified as Bad inhibitors (e.g., Bad antagonists); such agents enhance the death repressor activity of bcl-$x^L$ and/or bcl-2 and can be used to inhibit apoptosis and senescent cell death. Agents which, when added to a binding reaction, enhance formation of Bad:bcl-$x^L$ and/or Bad:bcl-2 complexes (and thus enhance formation of Bax-:Bax complexes or free Bax, if present) are thereby identified as Bad potentiators (e.g., Bad agonists; such agents reduce the death repressor activity of bcl-$x^L$ and/or bcl-2 and enhance the death effector function of Bax.

In one embodiment, candidate therapeutic agents are identified by their ability to block the binding of a Bad polypeptide to a bcl-$x^L$ polypeptide. The Bad polypeptide preferably comprises the Bad BH1 and BH2 domains, and often is a full-length mature Bad protein. The bcl-$x^L$ polypeptide preferably comprises the bcl-$x^L$ BH1 and BH2 domains, and often is a full-length mature bcl-$x^L$ protein.

In one embodiment, candidate therapeutic agents are identified by their ability to block the binding of a Bad polypeptide to a bcl-2 polypeptide. The Bad polypeptide preferably comprises the Bad BH1 and BH2 domains, and often is a full-length mature Bad protein. The bcl-2 polypeptide preferably comprises the bcl-2 BH1 and BH2 domains, and often is a full-length mature bcl-2 protein.

In one embodiment, candidate therapeutic agents are identified by their ability to block the binding of a Bad polypeptide to a bcl-2-related polypeptide. The Bad polypeptide preferably comprises the human Bad BH1 and BH2 domains, and often is a full-length mature human Bad protein. The bcl-2-related polypeptide preferably comprises the human bcl-2 BH1 and BH2 domains, and often is a full-length mature human bcl-2 protein.

Typically, a Bad polypeptide used in these methods comprises an amino acid sequence identical to a naturally-occurring Bad protein sequence, although mutant Bad polypeptides are sometimes used if the mutant Bad polypeptide binds to the bcl-$x^L$ or bcl-2 polypeptide under control assay conditions (e.g., physiological conditions). Agents are tested for their ability to alter binding between a Bad polypeptide and a bcl-$x^L$ or bcl-2 polypeptide under suitable assay binding conditions.

One means for detecting binding of a Bad polypeptide to a bcl-$x^L$ polypeptide is to immobilize the Bad polypeptide, such as by covalent or noncovalent chemical linkage to a solid support, and to contact the immobilized Bad polypeptide with a bcl-$x^L$ polypeptide that has been labeled with a detectable marker (e.g., by incorporation of radiolabeled amino acid, by epitope tagging and reporting with a fluorescent-labelled anti-epitope tag antibody, and the like). Such contacting is typically performed in aqueous conditions which permit binding of a Bad polypeptide to a bcl-$x^L$ polypeptide comprising a functional Bad binding site. Binding of the labeled bcl-$x^L$ polypeptide to the immobilized Bad is measured by determining the extent to which the labeled bcl-$x^L$ polypeptide is immobilized as a result of a specific binding interaction. Such specific binding may be reversible, or may be optionally irreversible if a cross-linking agent is added in appropriate experimental conditions.

Alternatively, the bcl-$x^L$ polypeptide may be labelled and the Bad polypeptide immobilized. In one variation, the binding assay is performed with soluble (i.e., non-immobilized) bcl-$x^L$ and Bad polypeptides and the resultant bound complexes (bcl-$x^L$:Bad) are separated from unbound bcl-$x^L$ and Bad polypeptides, and the bound complexes are quantitated. Agents that inhibit or augment the formation of bound complexes as compared to a control binding reaction lacking agent are thereby identified as Bad-modulating agents and are candidate therapeutic agents.

Alternatively, the bcl-2 polypeptide may be labelled and the Bad polypeptide immobilized. In one variation, the binding assay is performed with soluble (i.e., non-immobilized) bcl-2 and Bad polypeptides and the resultant bound complexes (bcl-2:Bad) are separated from unbound bcl-2 and Bad polypeptides, and the bound complexes are quantitated. Agents that inhibit or augment the formation of bound complexes as compared to a control binding reaction lacking agent are thereby identified as Bad-modulating agents and are candidate therapeutic agents.

In one variation, the binding assay is performed in vivo in a cell, such as a yeast cell (e.g., Saccharomyces), and agents which inhibit intermolecular binding between a Bad protein and a bcl-$x^L$ or bcl-2 polypeptide are identified as Bad-modulating agents. Frequently, the in vivo screening assay is a yeast two-hybrid system wherein the yeast cells express: (1) a first fusion protein comprising Bad and a first transcriptional regulatory protein sequence (e.g., GAL4 activation domain), (2) a second fusion protein comprising a bcl-$X^L$ or bcl-2 polypeptide and a second transcriptional regulatory protein sequence (e.g., GAL4 DNA-binding domain), and (3) a reporter gene (e.g., β-galactosidase, an auxotroph complementing gene) which is transcribed when an intermolecular complex comprising the first fusion protein and the second fusion protein is formed. If a functional bcl-$x^L$:Bad or bcl-2:Bad polypeptide complex forms, such as in a control assay lacking agent, the cell expresses the reporter gene which can be detected. Agents which inhibit or augment formation of functional bcl-2:Bad or bcl-$x^L$:Bad polypeptide complexes (and thus reporter gene expression) are thereby identified as Bad-modulating agents and candidate drugs and commercial cell culture reagents and cell preservatives (e.g., for explanted organs prior to transplant, etc.) and the like.

Methods for Forensic Identification

The Bad polynucleotide sequences of the present invention can be used for forensic identification of individual humans, such as for identification of decedents, determination of paternity, criminal identification, and the like. For example but not limitation, a DNA sample can be obtained from a person or from a cellular sample (e.g., crime scene evidence such as blood, saliva, semen, blood-stained gloves, blood spots on the door of a white Ford Bronco, and the like) and subjected to RFLP analysis, allele-specific PCR, or PCR cloning and sequencing of the amplification product to determine the structure of the Bad gene region. On the basis of the Bad gene structure, the individual from which the sample originated will be identified with respect to his/her Bad genotype. The Bad genotype may be used alone or in conjunction with other genetic markers to conclusively identify an individual or to rule out the individual as a possible perpetrator.

In one embodiment, human genomic DNA samples from a population of individuals (typically at least 50 persons from various racial origins) are individually aliquoted into reaction vessels (e.g., a well on a microtitre plate). Each aliquot is digested (incubated) with one or more restriction enzymes (e.g., EcoRI, HindIII, SmaI, BamHI, SalI, NotI, AccI, ApaI, BglII, XbaI, PstI) under suitable reaction conditions (e.g., see New England Biolabs 1993 catalog). Corresponding digestion products from each individual are loaded separately on an electrophoretic gel (typically agarose), electrophoresed, blotted to a membrane by Southern blotting, and hybridized with a labeled Bad probe (e.g., a full-length Bad cDNA sequence of FIG. 1 or FIG. 2(*b*) or cognate human Bad cDNA or gene sequence). Restriction fragments (bands) which are polymorphic among members of the population are used as a basis to discriminate Bad genotypes and thereby classify individuals on the basis of their Bad genotype.

Similar categorization of Bad genotypes may be performed by sequencing PCR amplification products from a population of individuals and using sequence polymorphisms to identify alleles (genotypes), and thereby identify or classify individuals.

The invention also provides Bad polynucleotide probes for diagnosis of disease states (e.g., neoplasia or preneoplasia) by detection of a Bad mRNA or rearrangements or amplification of the Bad gene in cells explanted from a patient, or detection of a pathognomonic Bad allele (e.g., by RFLP or allele-specific PCR analysis). Typically, the detection will be by in situ hybridization using a labeled (e.g., $^{32}P$, $^{35}S$, $^{14}C$, $^{3}H$, fluorescent, biotinylated, digoxigeninylated) Bad polynucleotide, although Northern blotting, dot blotting, or solution hybridization on bulk RNA or poly $A^+$ RNA isolated from a cell sample may be used, as may PCR amplification using Bad-specific primers. Cells which contain an altered amount of Bad mRNA as compared to non-neoplastic cells of the same cell type(s) will be identified as candidate diseased cells. Similarly, the detection of pathognomonic rearrangements or amplification of the Bad gene locus or closely linked loci in a cell sample will identify the presence of a pathological condition or a predisposition to developing a pathological condition (e.g., cancer, genetic disease). The polynucleotide probes are also used for forensic identification of individuals, such as for paternity testing or identification of criminal suspects (e.g., O. J. Simpson) or unknown decedents.

Methods of Rational Drug Design

Bad, bcl-$x^L$, and bcl-2 polypeptides, especially those portions which form direct contacts in Bad:bcl-2 or Bad:bcl-$x^L$ heteromultimers, can be used for rational drug design of candidate Bad-modulating agents (e.g., antineoplastics and immunomodulators). The substantially purified Bad/bcl-2 and Bad:bcl-$x^L$ heteromultimers and the identification of Bad as a docking partner for bcl-2 and bcl-$x^L$ as provided herein permits production of substantially pure Bad/bcl-2 polypeptide complexes and substantially pure Bad/bcl-$x^L$ polypeptide complexes. The disclosed sequences and protein sources provide data for computational models which can be used for protein X-ray crystallography or other structure analysis methods, such as the DOCK program (Kuntz et al (1982) *J. Mol. Biol.* 161: 269; Kuntz ID (1992) *Science* 257: 1078) and variants thereof. Potential therapeutic drugs may be designed rationally on the basis of structural information thus provided. In one embodiment, such drugs are designed to prevent formation of a Bad polypeptide:bcl-2 polypeptide complex and/or to prevent formation of a Bad polypeptide:bcl-$x^L$ polypeptide complex. Thus, the present invention may be used to design drugs, including drugs with a capacity to inhibit binding of Bad to bcl-2 and/or bcl-$x^L$. In one variation, such drugs are structural mimics of a bcl-2 BH1 or BH2 domain. In one variation, such drugs are structural mimics of a bcl-$x^L$ BH1 or BH2 domain. In one variation, such drugs are structural mimics of a Bad BH1 or BH2 domain.

The following examples are given to illustrate the invention, but are not to be limiting thereof. All percentages given throughout the specification are based upon weight unless otherwise indicated. All protein molecular weights are based on mean average molecular weights unless otherwise indicated.

EXPERIMENTAL EXAMPLES

Overview

We screened both a yeast two-hybrid system and a lambda expression cloning system for bcl-2 interacting proteins. The screening identified a new interacting protein, Bad, whose homology to bcl-2 clusters primarily in the BH1 and BH2 domains. Bad selectively dimerized with bcl-$x_L$ as well as bcl-2, but not with Bax, bcl-$x_S$, Mcl-1, A1, or itself. Bad binds more strongly to bcl-$x_L$ than bcl-2 in mammalian cells, and reversed the death repressor activity of bcl-$x_L$, but not that of bcl-2. When Bad dimerized with bcl-$x_L$, Bax was displaced and apoptosis was restored. When approximately half of Bax was heterodimerized, death was inhibited. The susceptibility of a cell to a death signal is determined by these competing dimerizations in which levels of Bad influence the effectiveness of bcl-2 versus bcl-$x_L$ in repressing death.

An expanding family of bcl-2 related proteins has recently been noted which share homology that is principally, but not exclusively, clustered within two conserved regions entitled bcl-homology I and 2 (BH1 and BH2) (Williams and Smith (1993) op.cit; Yin et al. 1994) op.cit). This includes Bax, bcl-$X_L$, Mcl-1, and A1, and several open reading frames in DNA viruses including BHRF1 of Epstein-Barr virus and LMW5-HL of African swine fever virus (Oltvai et al. (1993) op.cit; Boise et al. (1993) op.cit; Kozopas et al. (1993) Op.cit; Lin et al (1993) op.cit). Several of these have been shown to regulate cell death, including bcl-$x_L$, which represses apoptosis, and its short form bcl-$x_S$, which favors cell death (Boise et al. (1993) op.cit). The Bax protein has been shown to homodimerize as well as heterodimerize with bcl-2 in vivo. When in excess, Bax counters bcl-2's ability to repress cell death (Oltvai et al. (1993) op.cit).

Mutagenesis analysis of the BH1 and BH2 domains in bcl-2 identified single amino acid substitutions which disrupted bcl-2:Bax heterodimers, but not bcl-2:bcl-2 homodimers. Of note, the bcl-2 mutants that failed to complex with Bax could no longer inhibit apoptosis (Yin et al. (1994) op. cit). We introduced an equivalent BH1 substitution in bcl-$x_L$; a gly159ala substitution in BH1 of bcl-$x_L$ disrupted its heterodimerization with Bax and abrogated its inhibition of apoptosis (death repressor function) in mammalian cells. These data indicate that the family of bcl-2-related proteins functions through protein-protein interactions.

Analysis of the known bcl-2 family members in a yeast two hybrid assay system demonstrated a selectivity to their dimerizations. Wild-type bcl-2 protein, but not BH1 mutants, interacted with Bax in the yeast two-hybrid assay. We identified additional bcl-2-interacting proteins by using bcl-2 protein as bait to screen cDNA libraries in yeast two-hybrid and λ expression cloning. Both approaches identified the same distant homolog, Bad (bcl-$x_L$/bcl-2-associated neath promoter), which was conserved within the BH1 and BH2 domains. Bad displays selectivity in its interactions with bcl-2 family members, heterodimerizing with bcl-$x_L$ as well as bcl-2, but not with other members of the known family. When Bad heterodimerizes with bcl-$x_L$ in mammalian cells, it displaces Bax and promotes cell death.

FIG. 1 shows the nucleotide sequence (SEQ ID NO:1) of the Bad cDNA thus isolated. The deduced amino acid sequence of Bad (SEQ ID NO:2) is shown in FIG. 1 and FIG. 2(*a*). FIG. 2(*b*) shows the coding portion of the mouse Bad cDNA.

Isolation of Bad

To screen for bcl-2-interacting proteins, we utilized the yeast two-hybrid system and λ expression cloning (Chien et al. (1991) op.cit; Blanar and Rutter (1992) *Science* 256: 1014. bcl-2 was fused to the GAL4 DNA binding domain (DB) to generate a bait plasmid for the yeast two-hybrid screen. The carboxy-terminal signal-anchor sequence of bcl-2 was deleted in pPC97Bcl-2ΔC21, to ensure the fusion protein's translocation to the nucleus as depicted in FIG. 3(*a*). For a positive control, pPC86BaxΔC18, a GAL4 activation domain (AD) plasmid containing the murine Bax cDNA deleted of the carboxy-terminal 18 amino acid transmembrane segment, was utilized. When transformed into the yeast reporter strain PCY2, GAL4DB-Bcl-2ΔC21 did not activate transcription by itself, while GAL4DB-Bcl-2ΔC21 heterodimerized with GAL4AD-BaxΔC18 to activate transcription of lacZ in an X-gal filter assay. Subsequently, the GAL4DB-Bcl-2ΔC21 bait plasmid was used to screen an oligo-dT primed mouse embryonic day 14.5 cDNA fusion library in a GAL4AD vector (Chevray and Nathans (1992) *Proc. Natl. Acad. Sci.* (*USA*) 89: 5789). Approximately 400,000 $LEU^+TRP^+$ colonies were screened by the X-gal filter assay. Isolates from blue colonies were tested for their specificity of interaction with bcl-2 both by mating and transformation approaches. These tests compared the isolates' ability to activate lacZ transcription with the GAL4DB vector alone, GAL4DB-BaxΔC18, and GAL4DB with a nonspecific bait. Twelve positive colonies were confirmed in this manner. Sequence analysis of cDNA plasmids rescued from these 12 yeast colonies revealed that four plasmids represented two independent clones of the same gene (FIG. 4(*a*)).

For λ expression cloning, a bacterially synthesized bcl-2 fusion protein containing a 5-amino acid heart muscle kinase domain (Blanar and Rutter (1992) *Science* 256: 1014, GST-HMK-Bcl-2ΔC21, was in vitro labeled with 32P-γ-ATP, and used to screen an oligo-dT primed mouse embryonic day 16 Ex-lox library (Novagen). Twelve positive plaques were identified from 750,000 screened (FIG. 3(*b*)). The 12 rescued plasmids represented 3 overlapping clones of the same gene also isolated from yeast two-hybrid screening (FIG. 3(*b*)). For Western blots performed using either GST alone or GST-bcl-2 as probes against the fusion proteins produced by the three isolates indicated binding was specific for bcl-2 and not GST. Therefore, the same bcl-2-interacting protein was isolated by two interactive cloning strategies using two separate libraries. Alignment of the 5 clones narrowed the bcl-2-interacting region to 64 amino acids at the carboxy-terminus (FIG. 5).

bad cDNA and Protein Sequence

The full length Bad cDNA sequence was determined from clones identified from mouse newborn brain and adult thymus libraries (FIG. 4(*c*)). The gene contains an open reading frame encoding a previously undescribed protein of 204 amino acids with a predicted molecular weight of 22.1 kD (FIG. 1). We will subsequently refer to this gene as Bad (bcl-$x_L$lbcl-2 associated death promoter) for reasons that will be detailed. Comparison of the Bad protein sequence with the known bcl-2 family members revealed limited homology clustered in the BH1 and BH2 domains (FIGS. 5(*b*) and (*c*)). Specifically, Bad contains the highly conserved and functionally significant W/YGR triplet in BH1, the functionally significant W at position 183 and the WD/E at the conserved exon juncture in BH2 (FIG. 5(*c*)) (Yin et al. (1994) op.cit). Moreover, the spacing between the conserved BH1 and BH2 domains in Bad is similar to that of the other bcl-2 homologs. The shortest Bad clone that interacted with bcl-2 possessed the BH1 and BH2 region indicating that these conserved amino acids are be important for binding to bcl-2. It appears that Bad is most similar to the *C. elegans* protein Ced-9 in this region. Unlike the other known bcl-2 family members, Bad does not have a predicted carboxy-terminal signal-anchor sequence, consistent with the model that it does not exist as an integral membrane protein. Like the bcl-2 homolog Mcl-1, Bad contains two predicted PEST sequences flanked by arginine or arginine and histidine residues (FIG. 1, dotted underline). PEST sequences characterize certain proteins targeted for rapid degradation (Rogers et al. (1986) *Science* 234: 364). Bad contains a large number of charged residues (25 Arg+Lys, 23 Asp+Glu), with an estimated isoelectric point of 9.7, and an estimated charge of 2.47 at neutral pH. PROSITE analysis identified several potential phosphorylation and myristoylation sites. BLAST searches revealed no further detectable homologies within the existing databases.

Expression pattern of Bad

Figure 6B:
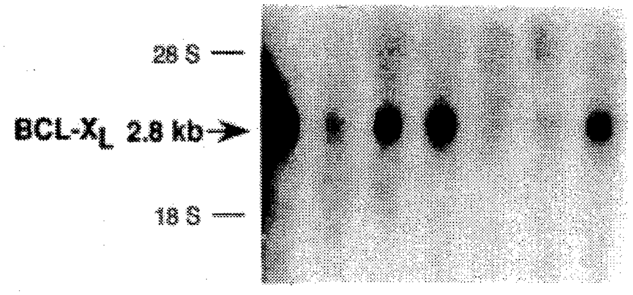
Figure 6C:
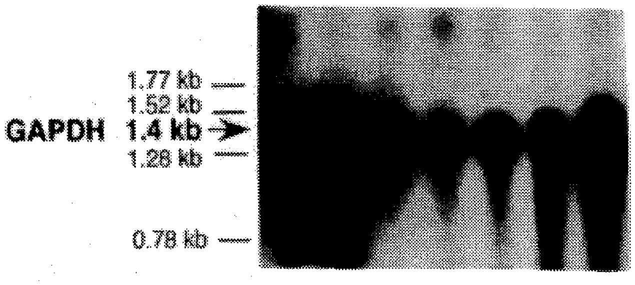
Figures 7A, 7B, 7C:
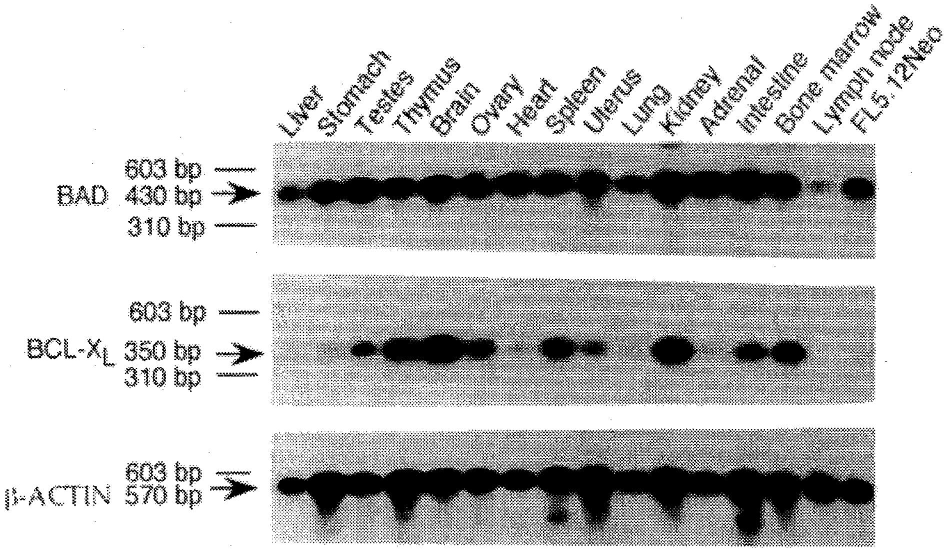
FIG. 7. Tissue Northern analysis and RT-PCR of Bad and bcl-$x_L$. Reverse transcriptase reactions were performed on 1 μg of total RNA from mouse organs. One-fourth (250 ng RNA equivalent) of the RT reaction product was used for Bad and bcl-$x_L$ PCR, while one fortieth (25 ng RNA equivalent) of the RT reaction product was used for β-actin PCR. All PCRs were carried out for 25 cycles. Total RNA from FL5.12Neo cells was used as control.
Figure 8A:
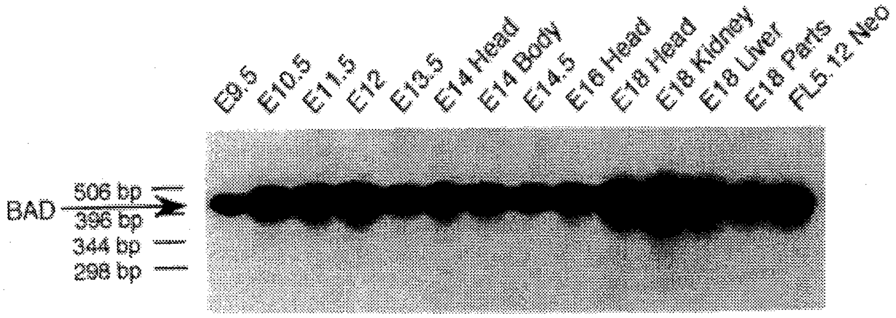
FIG. 8. RT-PCR of embryo RNAs. 1 μg of total RNA isolated from mouse embryos was used as substrate in random hexamer primed reverse transcriptase reactions. The equivalent of 250 ng of RNA was used for subsequent PCR reactions for Bad and bcl-$x_L$. The equivalent of 25 ng of RNA was used for β-actin PCR reactions. All PCRs were carried out for 25 cycles.
Figure 8B:
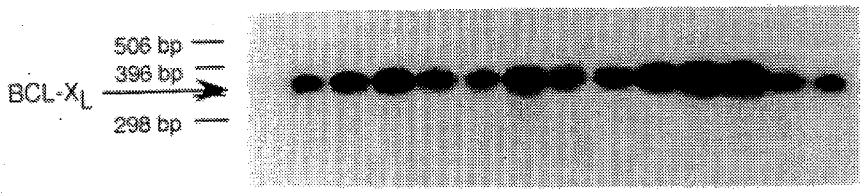
Figure 8C:

Northern analysis was performed on total RNA from various mouse organs to examine the tissue distribution of bad (FIG. 6). A PCR-labeled Bad coding region probe revealed a 1.1 kb RNA species. To increase the sensitivity, a semi-quantitative RT-PCR assay was developed using primers from separate exons of Bad. A tissue survey compared expression of bad to another bcl-2 homolog, bcl-$x_L$, by both Northern and RT-PCR assays, using either gapdh or β-actin as a control for RNA quality. Bad and bcl-$x_L$ are coexpressed in many tissues (FIG. 7). Bad appears to be ubiquitously expressed at a low level, and shows less tissue variation than bcl-$x_L$ (FIG. 7). The Bad mRNA level is several fold lower in lymph nodes than other organs examined, a finding also true for bcl-$x_L$. RT-PCR was also employed to examine Bad mRNA expression from day 9.5 to 18 during embryonic development (FIG. 8). Expression of Bad appears to precede that of bcl-$x_L$ at E9.5. Thereafter, the levels of Bad and bcl-$x_L$ relative to β-actin remain roughly constant during embryonic development (FIG. 8).

Interaction of Bad and Other bcl-2 Family Members

Since Bad interacted with bcl-2 and possesses BH1 and BH2 domains, we sought to determine whether it would also bind other bcl-2 family members. The full-length Bad cDNA was cloned into two other yeast two-hybrid vectors, pAS (GAL4DB) and PACTII (GAL4AD), which are 2μ-based multi-copy plasmids rather than centromeric low-copy plasmids (Durfee et al. (1993) op.cit). pASBad and pACTIIBad were systematically tested with the mammalian bcl-2 homologs, by both the X-gal filter assay and the liquid ONPG assay (FIG. 9). Bad interacted strongly with bcl-$X_L$ and bcl-2 in both the DNA binding domain and activation domain plasmids. However, Bad did not interact with Bax, bcl-xs, Mcl-1, or A1. Unlike bcl-2 or Bax, analysis in yeast two-hybrid indicates Bad substantially does not homodimerize.

Bad Heterodimerizes with bcl-2 and bcl-$X_L$ in Mammalian Cells

Figure 10:
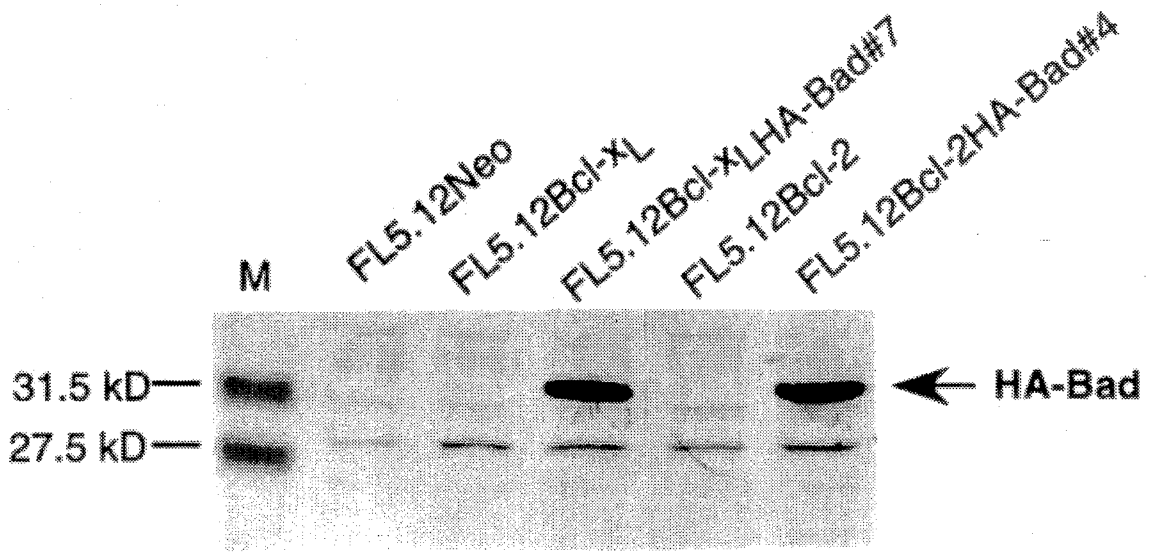
FIG. 10. Western blot analysis and viability of Bad-expressing FL5.12 clones. 75 μg of protein lysate was loaded in each lane. The anti-HA (hemagglutinin) mAb 12CA5 was used to detect the presence of HA-Bad. The blot was developed with DAB.
Figure 11:
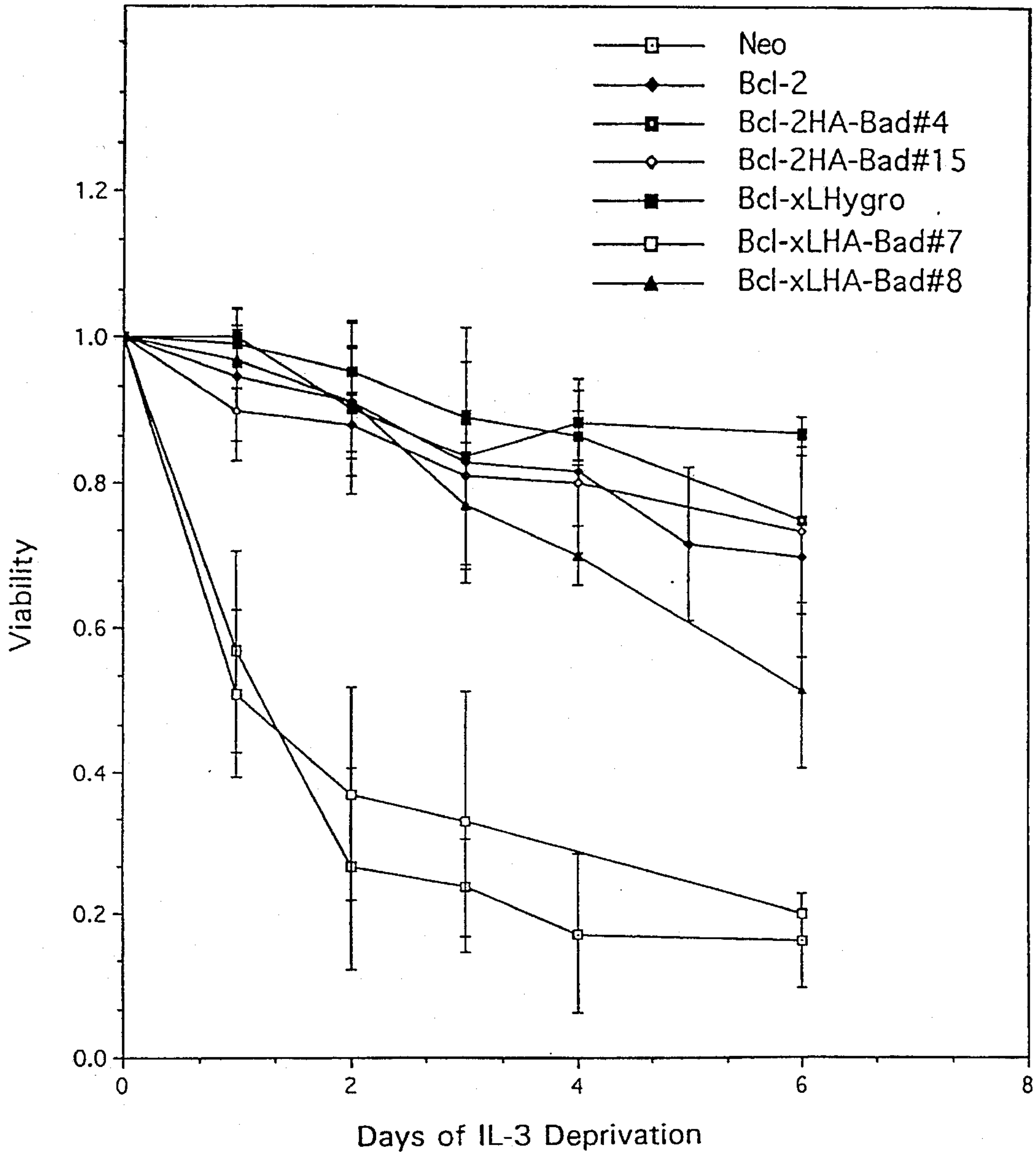
FIG. 11. Viability assays. Culture of independent clones indicated by the symbols were deprived of IL-3 and the fraction of viable cells ±SEM was assessed by trypan blue exclusion on the days indicated, and plotted. Data points and standard deviations were obtained from 3 or more experiments.

To determine whether Bad actually binds to bcl-2 and bcl-$x_L$ in mammalian cells, an expression plasmid was constructed placing Bad under the control of the splenic focus forming virus (SFFV) LTR (Fulbrigge et al. (1988) *Proc. Natl. Acad. Sci.* (*USA*) 85: 5649). A 9-amino acid hemagglutinin epitope tag was placed at the N-terminus of full-length Bad by a PCR approach (Kolodziej and Young (1991) op.cit). The resultant pSFFVHA-Bad plasmid was electroporated into the IL-3 dependent cell line FL5.12 (McKearn et al. (1985) *Proc. Natl. Acad. Sci.* (*USA*) 82: 7414), and into FL5.12 clones already overexpressing bcl-2 (Nuñez et al. (1990) op.cit) or bcl-$x_L$ (Boise et al. (1993) op.cit). Stable transfectants were selected by limiting dilution in G418 containing media, yielding 6 FL5.12HA-Bad clones, 4 FL5.12Bcl-2HA-Bad clones, and 4 FL5.12Bcl-$X_L$HA-Bad clones. The expression levels of HA-Bad in these clones was determined by Western blot analysis using either the monoclonal antibody to the HA tag (12CA5) or a newly generated polyclonal antibody to Bad (anti-Bad Ab). While the predicted MW of HA-Bad was 22.1 kD, it migrated at 30 kD in SDS-PAGE gels (FIG. 10). This apparent molecular weight was also noted with bacterially produced protein indicating that the anomalous migration is due to primary structure rather than post-translational modification. The FL5.12Bcl-2HA-Bad#4 and FL5.12Bcl-$X_L$HA-Bad#7 clones which expressed comparable amounts of Bad (FIG. 10) were selected for analysis of in vivo heterodimerizations. FIG. 11 shows viability curves deprived of IL-3.

Immunoprecipitation of Bad, bcl-2, and bcl-$X_L$ were performed with $^{35}S$—labeled cells solubilized in 0.2% NP-40, which permits dimers of the bcl-2 family to remain intact. The monoclonal antibody to human bcl-2, 6C8, immunoprecipitated the expected 25 kD bcl-2 protein and its heterodimerizing partner Bax from FL5.12Bcl-2 cells (FIG.

12($a$)). Immunoprecipitation of lysates from FL5.12Bcl-2HA-Bad#4 with 6C8 mAb yielded a 30 kD species in addition to bcl-2 and Bax. The 12CA5 mAb immunoprecipitated the same 30 kD band, confirming its identity as HA-Bad (FIG. 12($a$)). The 12CA5 primary immunoprecipitate also contained a 25 kD band, which proved to be bcl-2 by Western blot analysis (FIG. 12($b$)). In addition, the anti-Bad polyclonal antibody showed the same immunoprecipitation pattern as 12CA5. Therefore, we demonstrated that Bad co-precipitates with bcl-2, and bcl-2 co-precipitates with Bad. However, no Bax band was seen in the 12CA5 immunoprecipitation lane, confirming the absence of Bad/Bax heterodimerization, consistent with the yeast two-hybrid data. This also demonstrates that bcl-2 which is bound to HA-Bad is not substantially heterodimerized with Bax. Thus, there is no evidence for the presence of Bad/bcl-2/Bax heterotrimers.

A parallel series of immunoprecipitations was performed on FL5.12Bcl-$X_L$HA-Bad clones, using an anti-bcl-x polyclonal antibody. In FL5.12Bcl-$x_L$ cells, anti-bcl-x Ab captured the 28 kD bcl-$x_L$ protein and a 21 kD protein that has been proven to be Bax (FIG. 13($a$)). In FL5.12Bcl-$X_L$HA-Bad#7 lysates, anti-bcl-x Ab precipitated bcl-$X_L$ and a 30 kD species consistent with HA-Bad, the identity of which was confirmed on a Western blot using anti-Bad Ab (FIG. 13($c$)). Similarly, both the 12CA5 mAb and anti-Bad Ab precipitated a 28 kD species as well as the 30 kD HABad. Subsequent Western blot analysis of these primary immunoprecipitates with the anti-bcl-x Ab confirmed that the 28 kD protein was bcl-$x_L$ (FIG. 13($b$)). Thus, HA-Bad co-precipitates with bcl-$x_L$, and bcl-$x_L$ also co-precipitates with Bad. Once again, the bcl-$x_L$ molecules which are bound to Bad are not heterodimerized with Bax. Moreover, in the primary immunoprecipitate of FL5.12Bcl-$X_L$HA-Bad#7 with anti-bcl-x Ab, little or no Bax is present, indicating that nearly all of the bcl-$x_L$ is dimerized with HA-Bad (FIG. 13($a$)).

To further assess the extent to which HA-Bad had complexed with the available bcl-2 or bcl-$x_L$, secondary immunoprecipitations were performed on the supernatants of the aforementioned experiments. In lysates of FL5.12Bcl-2 HA-Bad#4 cells, the intensity of bcl-2 to HA-Bad bands in the primary immunoprecipitates with the 6C8 anti-bcl-2 mAb showed a ratio of 2:1, as assessed by phosphoimager scanning (FIG. 13($c$)). When the supernatant of this bcl-2-depleted immunoprecipitate was reprecipitated with anti-Bad Ab, a reversed ratio of bcl-2 to HA-Bad of 1:3 was noted (FIG. 13($c$)). This indicates that Bad was in excess, because free HA-Bad, not heterodimerized with bcL-2, existed. However, a parallel experiment with FL5.12Bcl-$x_L$ HA-Bad#7 cells revealed a bcl-$x_L$ to HA-Bad ratio of 1:1 in primary immunoprecipitates with anti-bcl-x Ab (FIG. 13($d$)). Whereas, when the supernatant of this bcl-$x_L$-depleted immunoprecipitate was reprecipitated with anti-Bad Ab or 12CA5, only small amounts of either protein were detected. The residual bcl-$x_L$ and HA-Bad detected were at a 1:1 ratio, consistent with the model that these minimal amounts of protein were complexed as heterodimers. These data are consistent with a strong affinity between bcl-$x_L$ and HA-Bad. In FL5.12Bcl-$X_L$HA-Bad#7 cells, nearly all the bcl-$x_L$ heterodimerized with HA-Bad and virtually none with Bax (FIG. 13($a$)). In FL5.1-2 Bcl-2 HA-Bad#4 cells, despite an excess of HA-Bad, a substantial fraction of bcl-2 is still heterodimerized with the endogenous Bax (FIG. 12($a$)). This is consistent with a comparatively weaker association between Bad and bcl-2 than Bad and bcl-$x_L$.

Bad Counters Death Inhibition By bcl-$x_L$ Not By bcl-2

The IL-3 dependent FL5.12 cell line normally dies by apoptosis following factor deprivation. Both bcl-2 and bcl-$x_L$ function as death repressors, extending the viability of these cells following IL-3 withdrawal. The six FL5.12HA-Bad clones were deprived of IL-3 to determine if overexpressed Bad affected apoptosis in this cell line with minimal to absent endogenous Bad protein. None of the viability curves of these six clones were convincingly different from that of FL5.12Neo control lines. We next examined whether the survival function of either bcl-2 or bcl-$x_L$ would be altered by the presence of Bad. The survival curves for two independent bcl-2 and Bad overexpressing clones, FL5.12Bcl-2 HABad#4 and #15 did not vary significantly from that of FL5.12Bcl-2 cells (FIG. 11). This indicates that at these expression levels, Bad protein has no substantial effect on the death repressor function of bcl-2 in this cell line. In contrast, the viability of clones co-expressing bcl-$x_L$ and Bad proved significantly different from that of FL5.12Bcl-$x_L$ cells. FL5.12Bcl-$x_L$ HA-Bad clone#7 expresses a high level of Bad and exhibits a viability that has nearly reverted to the pattern of several FL5.12Neo control lines (FIG. 11). FL5.12Bcl-$x_L$ HA-Bad#8 expresses a low amount of Bad protein (FIG. 14($a$)) and shows a slightly diminished viability compared to FL5.12Bcl-$x_L$ upon IL-3 withdrawal. Therefore, overexpressed Bad counters bcl-$x_L$'s death repressor activity, while similar levels of Bad (FIG. 10) were not effective in countering bcl-2 in this death assay. Immunoprecipitations using mouse thymocytes revealed an association of endogenous bcl-$x_L$ and Bad in vivo, indicating that this interaction is relevant in normal cells.

Bad Competes bcl-$X_L$ Resulting in Free Bax

Figure 12A:
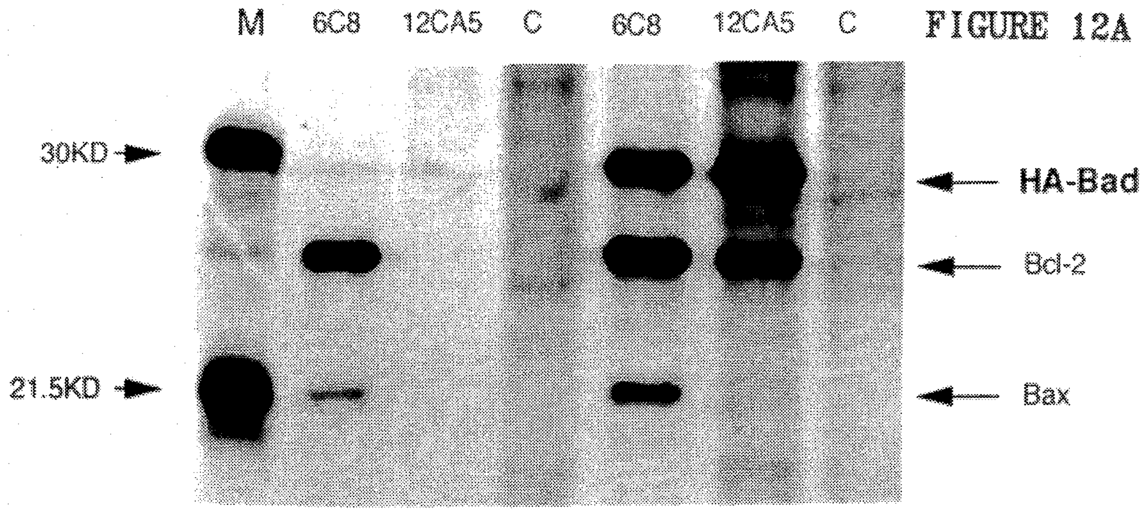
FIGS. 12(*a–c*). Co-immunoprecipitation of bcl-2 and Bad. (2*a*) Primary immunoprecipitation of the $^{35}$S-labeled FL5.12Bcl-2 line (lanes 2, 3, 4) and FL5.12Bcl-2 transfected with pSFFVHA-Bad, clone #4 (lanes 5, 6, 7). 6C8 is a mAb specific for human bcl-2, 12CA5 is a mAb specific for the influenza virus hemagglutinin (HA) epitope. C is a mouse anti-human cyclin antibody used as an isotype control, M denotes marker lane. Immunoprecipitated complexes were captured by protein A-Separose beads; one-half of each sample was loaded on a 12.5% SDS-PAGE gel, which was fluorographed. (12*b*) Western blot analysis of primary immunoprecipitates. One-half of each sample from (12*a*) was used in immunoblotting with 6C8 mAb and developed with ECL. (12*c*) Primary immunoprecipitation of $^{35}$S-labeled FL5.12Bcl-2HA-Bad#4 with 6C8 (lane 2), and secondary immunoprecipitation of that supernatant with anti-Bad Ab (lane 3).
Figure 12B:
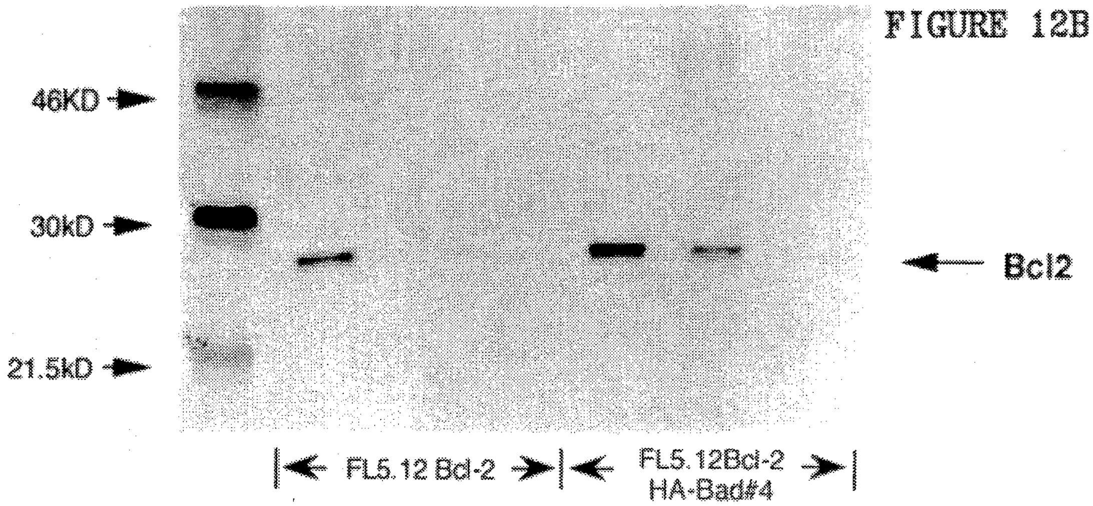
Figure 12C:
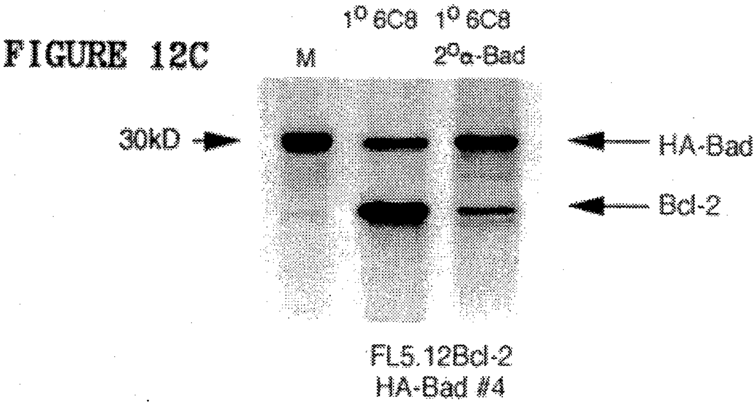

The differential effectiveness of Bad in countering bcl-$x_L$ but not bcl-2 activity may be explained by the observation that more of the available Bad is bound to bcl-$x_L$ than to bcl-2 (FIGS. 12, 13). Bad/bcl-$x_L$ heterodimerization appeared to preclude binding of bcl-$x_L$ to Bax, in that anti-bcl-x Ab no longer co-precipitated any Bax (FIG. 13($a$)). In contrast, despite an apparent excess of Bad in FL5.12Bcl-2 HA-Bad#4 cells, anti-bcl-2 mAb still co-precipitated some Bax as well as Bad (FIG. 12($a$)). Since heterotrimers do not appear to exist, this indicates that the amount of Bax that is "free" and not heterodimerized, would be affected by the presence of Bad.

Figures 14A, 14B, 14C:
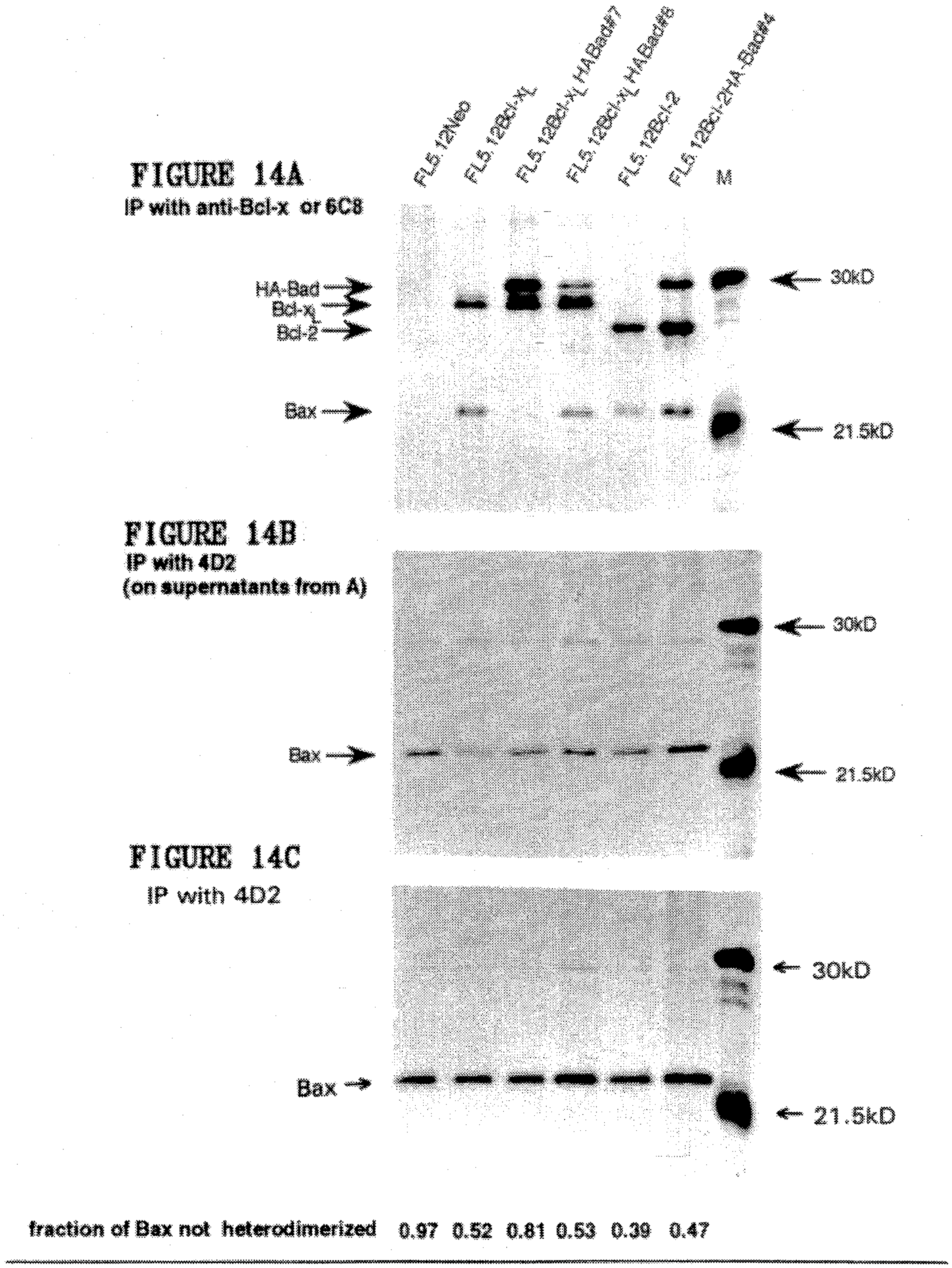
FIGS. 14(*a–c*). Amount of Bax not found in heterodimers in cells correlates with cell death. Sequential immunoprecipitations were performed on the clones indicated above the lanes. 20×$10^6$ cells of each were metabolically labeled. (14*a*) Primary immunoprecipitations with anti-bcl-x Ab or 6C8 mab. Using one-half of the $^{35}$S-labeled cells from each clone, anti-bcl-x Ab was incubated with 0.2% NP-40 lysates of clones expressing bcl-$X_L$, and 6C8 mAb was incubated with those expressing human bcl-2. Primary immunoprecipitations were separated on 12.5% SDS-PAGE gels and fluorographed. (14*b*) Immunoprecipitation of Bax from supernatants. Immunoprecipitations were performed on supernatants from cells in panel (14*a*). The supernatants from panel (14*a*) were cleared a second time with the same Ab to remove all bcl-$x_L$ and bcl-2 complexes. These doubly cleared supernatants were incubated with the 4D2 anti-BaxmAb and electrophoresed on 12.5% SDS-PAGE gels to quantitate the amount of Bax not complexed with either bcl-$x_L$ or bcl-2. (14*c*) Primary immunoprecipitation of total Bax. The other one-half of the original $^{35}$S-labeled cells were lysed in RIPA buffer and immunoprecipitated with the 4D2 MAb to quantitate the total amount of Bax. Bands were quantitated using a phosphoimager. The fraction of Bax that was not in heterodimers, and presumably homodimerized, was determined in 3 experiments and the average value is shown.

To test this hypothesis, the amount of Bax not involved in bcl-$x_L$:Bax or bcl-2:Bax heterodimers was determined in these clones. Sequential immunoprecipitations were performed in the following manner: primary immunoprecipitations were performed on $^{35}$S-labeled FL5.12Bcl-$x_L$ HA-Bad and FL5.12Bcl-2 HA-Bad clones lysed in 0.2% NP-40 using either anti-bcl-x Ab or 6C8 mAb, respectively (FIG. 14($a$)); the supernatants were cleared a second time with these antibodies to remove all bcl-$x_L$ or bcl-2 complexes; finally, these heterodimer-depleted supernatants were immunoprecipitated with the monoclonal anti-Bax antibody, 4D2 (FIG. 14($b$)). One-half of the original $^{35}$S-labeled cells were lysed in RIPA buffer, which disrupts dimers of this family, and immunoprecipitated with 4D2 mAb to establish the total amount of cellular Bax in each, preparation (FIG. 14($c$)). The amount of Bax present in each precipitation was quantitated by phosphoimager scanning. This experiment was performed three times and the average value for the fraction of Bax not found in heterodimers is presented (FIG. 14).

In FL5.12Neo control cells, most of the Bax (97%) was not heterodimerized, presumably present as homodimers, as shown previously (Oltvai et al. (1993) op.cit). The primary immunoprecipitation with 6C8 mAb and anti-bcl-x Ab confirmed the persistence of bcl-2:Bax heterodimers in FL5.12Bcl-2 HA-Bad#4 (FIG. 14(*a*)). bcl-$x_L$ :Bax heterodimers were noted in FL5.12Bcl-$x_L$HA-Bad#8 but not in FL5.12Bcl-$x_L$ HA-Bad clone #7 (FIG. 14(*a*)). Reciprocally, the amount of Bad committed to bcl-$x_L$:Bad heterodimers in clone #7 appeared greater than the amount of bcl-2:Bad heterodimers in clone #4 (FIG. 14(*a*)). This resulted in a marked difference in the fraction of Bax not present in heterodimers. In FL5.12Bcl-$x_L$ and FL5.12Bcl-2 cells which are protected from apoptosis, half or less of the total Bax was not heterodimerized (52% and 39%, respectively, FIG. 14). In FL5.12Bcl-$x_L$HA-Bad#7 cells which have regained susceptibility to death, as much as 79% of the total Bax was not complexed to bcl-$x_L$. In contrast, in FL5.12Bcl-$x_L$HA-Bad clone #8 and FL5.12Bcl-2HA-Bad#4, which still retained considerable protection, the percent of "free" Bax, not found in heterodimers, was 53% and 47%, respectively (FIG. 14).

Review

Both yeast two-hybrid and lambda expression cloning identified the same new bcl-2 family member, Bad. Several criteria qualify Bad for membership: Bad possesses the key amino acid motifs of BH1 and BH2 domains; a small region of Bad containing BH1 and BH2 binds bcl-2; and the molecular weight of Bad falls within the range of other bcl-2 family members. However, outside BH1 and BH2, Bad is quite distinct from other members. Moreover, Bad lacks the classic carboxy-terminal signal-anchor sequence responsible for the integral membrane position of other family members.

Initial immunofluorescence studies reveal a punctate cytoplasmic distribution for Bad similar to that of bcl-2 or bcl-$x_L$, perhaps reflecting its heterodimerization with these integral membrane proteins.

Figure 15:
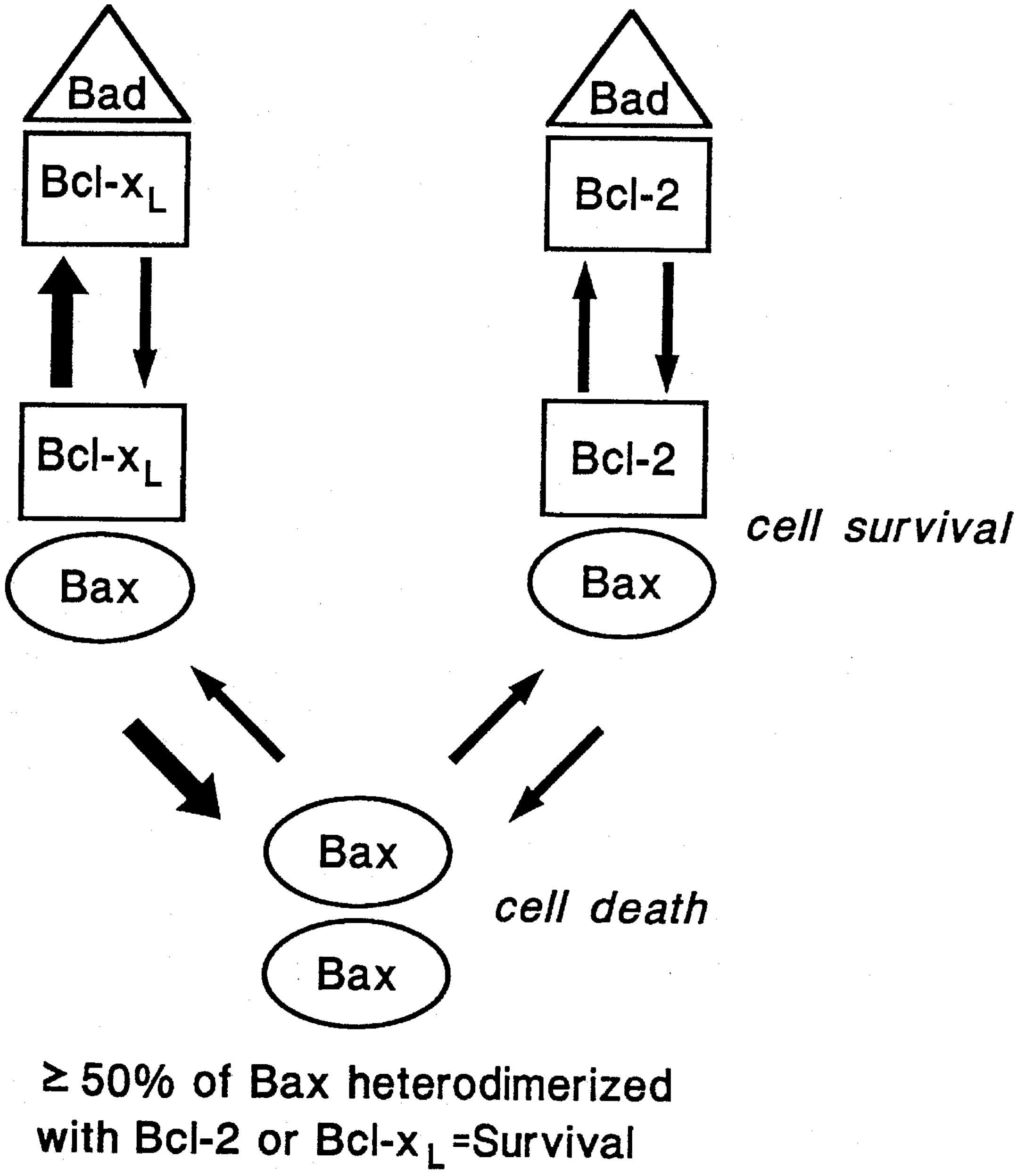
FIG. 15. Schematic representation of the competition of Bad for either bcl-$x_L$ or bcl-2. While bcl-2:Bad heterodimers are detected. they do not markedly change the amount of Bax homodimers. In contrast, the bcl-$x^L$:Bad interaction is apparently stronger, displacing bcl-$x_L$ from Bax, resulting in more Bax:Bax homodimers.

Yeast two-hybrid analysis indicated that Bad was selective in its interactions with family members, but that it would recognize bcl-$x_L$ as well as bcl-2. Assessment of Bad in mammalian cells confirmed this prediction. The immunoprecipitation data favor a model of simple dimers in which Bad competes with Bax for association with bcl-2 or bcl-$x_L$ (FIG. 15). There was no evidence for the existence of any heterotrimers. Although the quantitative ONPG assay in yeast two-hybrid indicated that the interaction of Bad is stronger for bcl-2 than bcl-$x_L$, studies in mammalian cells showed the opposite. When comparable levels of Bad were added to cells expressing either bcl-2 or bcl-$x_L$, more bcl-$x_L$:Bad than bcl-2:Bad heterodimers were detected. The binding of Bad appeared to preclude the binding of Bax to either bcl-$x_L$ or bcl-2. In cells with abundant bcl-$x_L$:Bad heterodimers, no bcl-$x_L$:Bax heterodimers were present. Since less bcl-2 is complexed with Bad, bcl-2:Bax heterodimers were still present in bcl-2 expressing cells. This is consistent with the model that Bad has a higher affinity for bcl-$x_L$ than for bcl-2. Studies within a cell death assay corroborated the significance of Bad heterodimerizations. When expressed as a sole molecule, Bad had no effect upon the death course of FL5.12 cells deprived of factor. This indicates that Bad itself does not function as a singular, downstream death effector molecule. FL5.12 cells express little bcl-2, no detectable bcl-$x_L$, and abundant Bax protein. Given the heterodimerization pattern of Bad, we asked if it would alter the apoptotic response in bcl-2 or bcl-$x_L$ protected cells. We found that Bad countered the death inhibition-by bcl-$x_L$ much more than bcl-2. This correlated with the proclivity of Bad to heterodimerize with bcl-$x_L$ more than bcl-2.

bcl-$x_L$ heterodimerizes with Bax in mammalian cells as well as yeast two-hybrid. A WAR for WGR substitution of the critical glycine in the BH1 domain was generated for bcl-$x_L$. Parallel to this mutation in bcl-2, this bcl-$x_L$ mI-3 protein no longer heterodimerized with Bax and also lost its death repressor activity. This provides further evidence for a model in which both bcl-$x_L$ and bcl-2 must dimerize with Bax to repress death. Bad further supports this thesis.

Overall, the data are consistent with a competition in which Bad binds bcl-$X_L$, displacing Bax into homodimers (FIG. 15). Susceptibility to cell death is best correlated with the percent of Bax in heterodimers versus homodimers. If roughly half of Bax is complexed in heterodimers, FL5.12 cells are protected from death.

Bad is a regulator of apoptosis that functions by sequestering bcl-$x_L$ or by altering its distribution between bcl-$x_L$:Bax versus bcl-$x_L$:Bad heterodimers. The susceptibility to cell death is dictated by a set point determined by the relative levels and interactions of bcl-$x_L$, bcl-2, Bax, and Bad proteins. Cells have been noted that vary in their capacity to be protected from death by bcl-$x_L$ versus bcl-2. The presence of the newly described protein, Bad, is a regulator that can determine whether the bcl-2 or the bcl-$x_L$ molecule will be effective in repressing apoptosis.

Experimental Procedures

Standard PCR reactions were used to construct all yeast fusion plasmids. Restriction enzyme sites were incorporated into oligonucleotide primers used to amplify bcl-2 family member cDNAs such that ligation to yeast vectors produced in-frame fusions with either the GAL4 DNA binding domain or the GAL4 transcription activation domain. The amino acids in the COOH-terminal transmembrane segments were deleted from bcl-2 homologs as follows: 21 amino acids from mubcl-2, 18 from muBax, 19 from hubcl-$x_L$, 19 from hubcl-$x_S$, 21 from muMcl-1, and 21 from muA1. pASBAD and PACTIIBAD constructs contained full-length cDNA. The yeast vectors pPC97 and pAS contain the GAL4 DNA binding,domain and express the LEU and TRP markers, respectively; pPC86 and PACTII contain the GAL4 transcription activation domain and express the TRP and LEU markers, respectively.

The expression plasmid SFFVHA-Bad was constructed by using PCR primers which incorporated the 9 codons of the HA (hemagglutinin) epitope onto the 5' end of Bad. The PCR product was ligated into PSFFV vector at the EcoRI site.

Strains and Cell Lines

The yeast strain used in yeast two-hybrid screening was PCY2 (MATαΔgal4Δgal80URA3::GAL1-lacZlys2-801amberhis3-Δ200trp1-Δ63leu2ade2-101$^{ochre}$). The strain used in matings to test non-specific interactions was Y190 (MATagal4gal80his3trp1-901ade2101ura3-52leu2-3,-112URA3::GAL-lacZLYS::GAL-HIS3cyh$^r$). Yeast transformations were done using the standard lithium acetate procedure.

The murine IL-3 dependent early hematopoietic cell line, FL5.12, and its derivatives were grown in Iscove's modified Dulbecco's medium supplemented with 10% fetal calf serum and 10% WEHI-3B conditioned medium as a source of IL-3.

Yeast Two-Hybrid Screening

PCY2 transformed with pPC97bcl-2 was maintained in -leu medium. This strain was transformed with 4 μg of an oligo-dT primed mouse 14.5 day embryo fusion cDNA library constructed in the activating domain vector pPC67. Approximately 400,000 LEU+TRP+ colonies were screened by the filter X-gal assay. Blue colonies were grown in +Leu liquid medium to allow for loss of the bait plasmid and replica plated onto -leu-trp plates. Those colonies which grew on +Leu-trp but not on -leu-trp plates were mated to Y190 carrying either pPC97 vector alone, pPC97bcl-2, or a non-specific plasmid pPC97HoxII, and assayed for blue color by the filter assay. The cDNA plasmids were rescued from the positive yeast colonies and co-transformed with the various DNA binding domain plasmids back into PCY2. Only those cDNA plasmids which were specifically positive with bcl-2 both by mating and transformation were sequenced. Standard quantitative liquid ONPG assays were performed using yeast lysates, according to the protocol of Rose and Botstein.

Expression Cloning

Bacterially produced GST-HMK-Bcl-2 AC21 was purified using glutathione-agarose beads. 1 μg of protein was labeled with 100 μCi of $^{32}$P-γ-ATP using heart muscle kinase (Sigma) to a specific activity of >$10^7$ cpms/μg. Screening of phage filters was performed in 0.05% NP-40 and 1 mMDTT, according to the protocol of Blanar and Rutter.

cDNA Screening

A Bad coding region probe was used to screen $10^6$ plaques each of a mouse newborn brain and an adult thymus λZAPII cDNA library. Standard phage screening techniques were employed. Positive plaques were excised in vivo and sequenced.

Northern Blot Analysis and RT-PCR

Total RNA was extracted from mouse organs and embryos using RNazol. For Northern analysis, 30 μg were loaded in each lane of a 1.2% agarose formaldehyde gel which was transferred to Zetaprobe and hybridized with PCR-labeled Bad and bcl-$x_L$ coding region probes or a random primer labeled GAPDH probe. Blots were hybridized at 42° C. overnight and washed at 65° C. Bad and bcl-$x_L$ bands were quantitated by normalizing to GAPDH by phosphoimager scanning. For RT-PCR, reverse transcriptase reactions were performed using 1 μg of total RNA as template, random hexamers as primers, and GIBCO Superscript in 20 μl reactions. The reactions were incubated at room temperature for 10 minutes, 42° C. for 15 minutes, 99° C. for 5 minutes, and 5° C. for 5 minutes. ¼ of the RT reaction (or 250 ng RNA equivalent) was used for each Bad and bcl-$x_L$ PCR reaction. 1/40 of the RT reaction (or 25 ng RNA equivalent) was used for β-actin PCR. All primer pairs spanned intron/exon junctions. For Bad, the primers (sense: 5'TCGGAGTCGCCACAGTTCGTA3' [SEQ ID NO.:53], antisense: 5'GACTCAAGCTGTACGTCAGCT3' [SEQ ID NO.:54]) generated a product of 430 bp. For bcl-$X_L$, the sense primer was 5'ATGACTTTGAACTGCGGTACC3' [SEQ ID NO.:55] and the antisense primer was 5'AAGCGCTCCTGGCCTTTCCGG3' [SEQ ID NO.:56], generating a product of 350 bp. The β-actin primers were sense: 5'ATGGATGACGATATCGCT [SEQ ID NO.:57], antisense 5'ATGAGGTAGTCTGTCATGGT3' [SEQ ID NO.:58], yielding a product of 570 bp. PCR cycles consisted of melting at 94° C. for 1 minute, annealing at 58° C. for 2 minutes, extension at 72° C. for 1 minute, for a total of 25 cycles. PCR products were run out in agarose gels, blotted, and hybridized with random primer labeled probes appropriate for each RT-PCR. Bad and bcl-$x_L$ bands were quantitated by normalizing to β-actin bands by phosphoimager scanning.

Transfections

FL5.12 cells were electroporated at 200 volts and 900 μF. 48 hours later, the cells were plated in medium containing 1 mg/ml G418 in 96-well microtiter dishes. Single cell origin clones were picked 10–14 days later.

Viability Assays

FL5.12 clones were washed 4 times in medium without serum or IL-3, and plated in medium without IL-3 at a concentration of $10^6$ cells/ml in microtiter wells. Aliquots of cells were removed from different wells and stained with trypan blue at indicated time points. Typically, at least 100 cells were counted in triplicate for each time point. Viability assays were performed at least three independent times for each clone.

Antibodies

6C8 is a human bcl-2-specific hamster monoclonal antibody. 12CA5 is a murine monoclonal antibody against influenza virus hemagglutinin protein epitope. 4D2 is a hamster monoclonal antibody against murine Bax. Anti-bcl-x Ab is a polyclonal antibody against bcl-x, the production of which will be described elsewhere. The rabbit polyclonal anti-Bad Ab was raised against bacterially produced protein and was protein A-purified. For immunoprecipitations, 6C8 was used at a final concentration of 20 μg/ml, 12CA5 was used at 40 μg/ml, anti-bcl-x Ab was used at 10 μl/$10^7$ cells. 4D2 and anti-Bad antibody were empirically titrated to be maximally efficient at 24 μg/ml and 60 μg/ml.

Western Blot Analysis

Cells were lysed in 100 mM Tris pH7.5, 75 mM NaCl, 1% Triton X-100, 1% PMSF, and 1% aprotinin. SDS-PAGE gels were transferred to Nitroplus filters and blocked in PBS, 0.05% Tween-20, and 3% nonfat milk. Antibody incubations were carried out for 1 hr at room temperature. 12CA5 mAb supernatant was used at 1:50 dilution, anti-bcl-x Ab at 1:1000, anti-Bad Ab at 1:1000, and 6C8 at 1:100. Biotinylated secondary goat antibody (Caltag) was used at 1:500, and horseradish peroxidase conjugated streptavidin (Zymed) was used at 1:1000 when developed with 3-aminodiazobenzidine, and 1:20,000 when developed with ECL.

Immunoprecipitations

Each immunoprecipitation was carried out using $10^7$ cells resuspended at $2\times10^6$ cells/ml in methionine-free Dulbecco's modified Eagle's medium supplemented with 10% dialyzed fetal calf serum and 10% WEHI-3B supernatant. 100 μCi Trans $^{35}$S-label was added to the medium for 12 hrs. Cultures were then washed with ice-cold PBS, and lysed in 0.5 ml of NP-40 isotonic buffer (10 mm HEPES pH 8.0, 142.5 mM KCl, 5 mM MgCl2, 0.2% NP-40, 1 mM PMSF, 1% aprotinin, 3 μg/ml pepstatin) or RIPA buffer for 30 minutes at 4°. Nuclei and cell debris were removed by centrifugation at 15,000×g for 10 minutes. Lysates were precleared with 50 μl of 50% v/v protein A-Sepharose for 30 minutes at 4° C. Antibody was added, and incubated at 4° C. for 60 minutes, followed by incubation with 50 μl of protein A-Sepharose for 45 minutes. The protein A-Sepharose beads were collected by a 30 second microfuge spin and washed 3 times with 1 ml of lysis buffer. In some experiments, the supernatants were incubated with a second antibody and the protein A-Sepharose steps were repeated. Immunoprecipitates were solubilized by boiling in sample loading buffer, and fractionated on 12.5% SDS-PAGE gels, fixed in 30% methanol 10% acetic acid, enhanced, dried, and exposed to X-ray film at −70° C. $^{35}$S-labeled bands were quantitated by phosphoimager scanning.

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
( A ) LENGTH: 1472 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

```
GGCACGAGCG GACCCCGCCC CCTAGCTTGT GTCTGCAGGC CCCGCGTCCG GCCCGGGGCA   60
GCGTACGCAC ACCTATCCTG GCAGCAGAGG CCCCTGGAGC CCCACGGCTC GCCTTCCTGG  120
GCGCCCCGTC CCTTCTTCCG CACCCGGGCG GCCATCCTGC CGTAAAGGAG CTCCCGAAAT  180
GGCGCGGGGG GTTGTCCCCA AGACGGGCAG TGCAAGGCCC TCCACGATCG GGAAGAAGGA  240
GCTGGTCTTC CCATCCCGGT CACTCGGTCC AGGGGGAGCA ATAACCATCG CAACGACCAT  300
TGCATCCGAC GGCCGAGCTT CAGTGAACGG CTCTATAAGT AATCACTAAG CTGTTTACAG  360
AGTTTTCACC AGCTCCCCAG GGAGGTGTCA TTAACCCCAT TTTACAGGAG GGAATTCGGG  420
CCCAGAAGGG CTGGAGGACT TATCAGCCGA AGCAGGCCTC CAGGATCCAA ATGGGAACCC  480
CAAAGCAGCC CTCGCTGGCT CCTGCACACG CCCTAGGCTT GAGGAAGTCC GATCCCGGAA  540
TCCGGAGCCT GGGGAGCGAC GCGGGAGGAA GGCGGTGGAG ACCAGCAGCC CAGAGTATGT  600
TCCAGATCCC AGAGTTTGAG CCGAGTGAGC AGGAAGACGC TAGTGCTACA GATAGGGGCC  660
TGGGCCCTAG CCTCACTGAG GACCAGCCAG GTCCCTACCT GGCCCCAGGT CTCCTGGGGA  720
GCAACATTCA TCAGCAGGGA CGGGCAGCCA CCAACAGTCA TCATGGAGGC GCAGGGGCTA  780
TGGAGACTCG GAGTCGCCAC AGTTCGTACC CAGCGGGGAC CGAGGAGGAT GAAGGGATGG  840
AGGAGGAGCT TAGCCCTTTT CGAGGACGCT CGCGTTCGGC TCCCCCCAAT CTCTGGGCAG  900
CGCAGCGCTA CGGCCGTGAG CTCCGAAGGA TGAGCGATGA GTTTGAGGGT TCCTTCAAGG  960
GACTTCCTCG CCCAAAGAGC GCAGGCACTG CAACACAGAT GCGACAAAGC GCCGGCTGGA 1020
CGCGCATTAT CCAGTCCTGG TGGGATCGAA ACTTGGGCAA AGGAGGCTCC ACCCCCTCCC 1080
AGTGATCTTC TGCTCCACAT CCCGGAACTC TACCCGCTCC CGTCGCCCGC CATATTGGGT 1140
GTGGGCGGAA GTCTTTCGAG GCCTTAGGAA AAAAAAAGAG GATCGCTGTG TCCCTTTAAC 1200
AGGGAGAAGA GCTGACGTAC AGCTTGAGTC CCTTCCGGTG CGTGCAATAG CCACGGAGGG 1260
GTGGCTCCTG TTTGGAGTTT CAAAGTTTTC CACGCACCCC ACCCCCTAAG CCTCCGGAAG 1320
TGGCTGTTTT CCCTCTCCTG TTCTGGACTG CCCTCGGGTG CCTGTGCTAA GTTGGGGGTC 1380
TGGGTGCTGT CCTGTCATAA CTGGGGACCC GAGGTCGCGA GAAACGTGCT TTATAATAAA 1440
```

-continued

GCCTGCGCAT GTGCAAAAAA AAAAAAAAAA AA 1472

( 2 ) INFORMATION FOR SEQ ID NO:2:

( i ) SEQUENCE CHARACTERISTICS:
( A ) LENGTH: 204 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..204
( D ) OTHER INFORMATION: /note= "Deduced amino acid sequence of mouse BAD."

( x i ) SEQUENCE DESCRIPTION: SEQ ID NO:2:

```
Met Gly Thr Pro Lys Gln Pro Ser Leu Ala Pro Ala His Ala Leu Gly
1               5                   10                  15

Leu Arg Lys Ser Asp Pro Gly Ile Arg Ser Leu Gly Ser Asp Ala Gly
            20                  25                  30

Gly Arg Arg Trp Arg Pro Ala Ala Gln Ser Met Phe Gln Ile Pro Glu
        35                  40                  45

Phe Glu Pro Ser Glu Gln Glu Asp Ala Ser Ala Thr Asp Arg Gly Leu
    50                  55                  60

Gly Pro Ser Leu Thr Glu Asp Gln Pro Gly Pro Tyr Leu Ala Pro Gly
65                  70                  75                  80

Leu Leu Gly Ser Asn Ile His Gln Gln Gly Arg Ala Ala Thr Asn Ser
                85                  90                  95

His His Gly Gly Ala Gly Ala Met Glu Thr Arg Ser Arg His Ser Ser
            100                 105                 110

Tyr Pro Ala Gly Thr Glu Glu Asp Glu Gly Met Glu Glu Glu Leu Ser
        115                 120                 125

Pro Phe Arg Gly Arg Ser Arg Ser Ala Pro Pro Asn Leu Trp Ala Ala
    130                 135                 140

Gln Arg Tyr Gly Arg Glu Leu Arg Arg Met Ser Asp Glu Phe Glu Gly
145                 150                 155                 160

Ser Phe Lys Gly Leu Pro Arg Pro Lys Ser Ala Gly Thr Ala Thr Gln
                165                 170                 175

Met Arg Gln Ser Ala Gly Trp Thr Arg Ile Ile Gln Ser Trp Trp Asp
            180                 185                 190

Arg Asn Leu Gly Lys Gly Gly Ser Thr Pro Ser Gln
        195                 200
```

( 2 ) INFORMATION FOR SEQ ID NO:3:

( i ) SEQUENCE CHARACTERISTICS:
( A ) LENGTH: 615 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: misc_feature
( B ) LOCATION: 1..615
( D ) OTHER INFORMATION: /note= "Polynucleotide coding sequence of mouse BAD cDNA."

( x i ) SEQUENCE DESCRIPTION: SEQ ID NO:3:

-continued

| | | | | | | |
|---|---|---|---|---|---|---|
| ATGGGAACCC | CAAAGCAGCC | CTCGCTGGCT | CCTGCACACG | CCCTAGGCTT | GAGGAAGTCC | 60 |
| GATCCCGGAA | TCCGGAGCCT | GGGGAGCGAC | GCGGGAGGAA | GGCGGTGGAG | ACCAGCAGCC | 120 |
| CAGAGTATGT | TCCAGATCCC | AGAGTTTGAG | CCGAGTGAGC | AGGAAGACGC | TAGTGCTACA | 180 |
| GATAGGGGCC | TGGGCCCTAG | CCTCACTGAG | GACCAGCCAG | GTCCCTACCT | GGCCCCAGGT | 240 |
| CTCCTGGGGA | GCAACATTCA | TCAGCAGGGA | CGGGCAGCCA | CCAACAGTCA | TCATGGAGGC | 300 |
| GCAGGGGCTA | TGGAGACTCG | GAGTCGCCAC | AGTTCGTACC | CAGCGGGGAC | CGAGGAGGAT | 360 |
| GAAGGGATGG | AGGAGGAGCT | TAGCCCTTTT | CGAGGACGCT | CGCGTTCGGC | TCCCCCCAAT | 420 |
| CTCTGGGCAG | CGCAGCGCTA | CGGCCGTGAG | CTCCGAAGGA | TGAGCGATGA | GTTTGAGGGT | 480 |
| TCCTTCAAGG | GACTTCCTCG | CCCAAAGAGC | GCAGGCACTG | CAACACAGAT | GCGACAAAGC | 540 |
| GCCGGCTGGA | CGCGCATTAT | CCAGTCCTGG | TGGGATCGAA | ACTTGGGCAA | AGGAGGCTCC | 600 |
| ACCCCCTCCC | AGTGA | | | | | 615 |

( 2 ) INFORMATION FOR SEQ ID NO:4:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

Glu Phe Phe Arg Asp Gly Val Asn Trp Gly Arg Ile Val Ala Phe Phe
1 5 10 15

Glu Phe Gly Gly
20

( 2 ) INFORMATION FOR SEQ ID NO:5:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:5:

Asp Met Phe Ala Asp Gly Asn Phe Asn Trp Gly Arg Val Val Ala Leu
1 5 10 15

Phe Tyr Phe Ala Ser
20

( 2 ) INFORMATION FOR SEQ ID NO:6:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:6:

Glu Leu Phe Arg Asp Gly Val Asn Trp Gly Arg Ile Val Ala Phe Phe
1 5 10 15

Ser Phe Gly Gly
20

-continued ( 2 ) INFORMATION FOR SEQ ID NO:7:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

Lys Glu Phe Glu Asp Gly Ile Ile Asn Trp Gly Arg Ile Val Thr Ile
1 5 10 15

Phe Ala Phe Gly Gly
20

( 2 ) INFORMATION FOR SEQ ID NO:8:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

His Val Phe Lys Asp Gly Val Thr Asn Trp Gly Arg Ile Val Thr Leu
1 5 10 15

Ile Ser Phe Gly Ala
20

( 2 ) INFORMATION FOR SEQ ID NO:9:

( i ) SEQUENCE CHARACTERISTICS:
( A ) LENGTH: 21 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

Ala Gln Thr Asp Gln Cys Pro Met Ser Tyr Gly Arg Leu Ile Gly Leu
1 5 10 15

Ile Ser Phe Gly Gly
20

( 2 ) INFORMATION FOR SEQ ID NO:10:

( i ) SEQUENCE CHARACTERISTICS:
( A ) LENGTH: 23 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:10:

Pro Pro Asn Leu Trp Ala Ala Gln Arg Tyr Gly Arg Glu Leu Arg Arg
1 5 10 15

Met Ser Asp Glu Phe Glu Gly
20

( 2 ) INFORMATION FOR SEQ ID NO:11:

( i ) SEQUENCE CHARACTERISTICS:
( A ) LENGTH: 17 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:11:

Thr Trp Ile Gln Asp Asn Gly Gly Trp Asp Ala Phe Val Glu Leu Tyr
1 5 10 15

Gly ( 2 ) INFORMATION FOR SEQ ID NO:12:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

Val Trp Ile Gln Asp Gln Gly Gly Trp Glu Gly Leu Leu Ser Tyr Phe
1 5 10 15

Gly ( 2 ) INFORMATION FOR SEQ ID NO:13:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:13:

Pro Trp Ile Gln Glu Asn Gly Gly Trp Asp Thr Phe Val Asp Leu Tyr
1 5 10 15

Gly ( 2 ) INFORMATION FOR SEQ ID NO:14:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:14:

Glu Trp Ile Arg Gln Asn Gly Gly Trp Glu Asp Gly Phe Ile Lys Lys
1 5 10 15

Phe ( 2 ) INFORMATION FOR SEQ ID NO:15:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:15:

Asp Trp Leu Val Lys Gln Arg Gly Trp Asp Gly Phe Val Glu Phe Phe
1 5 10 15

His (2) INFORMATION FOR SEQ ID NO:16:

(i) SEQUENCE CHARACTERISTICS:
(A) LENGTH: 17 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:16:

Asn Trp Lys Glu His Asn Arg Ser Trp Asp Asp Phe Met Thr Leu Gly
1 5 10 15

Lys (2) INFORMATION FOR SEQ ID NO:17:

(i) SEQUENCE CHARACTERISTICS:
(A) LENGTH: 16 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:17:

Gly Trp Thr Arg Ile Ile Gln Ser Trp Trp Asp Arg Asn Leu Gly Lys
1 5 10 15

(2) INFORMATION FOR SEQ ID NO:18:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:18:

Gly Thr Pro Lys Gln Pro Ser Leu Ala Pro Ala His Ala Leu
1 5 10

(2) INFORMATION FOR SEQ ID NO:19:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:19:

Arg Lys Ser Asp Pro Gly Ile Arg Ser Leu Gly Ser Asp Ala
1 5 10

(2) INFORMATION FOR SEQ ID NO:20:

(i) SEQUENCE CHARACTERISTICS:
(A) LENGTH: 17 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:20:

Arg Trp Arg Pro Ala Ala Gln Ser Met Phe Gln Ile Pro Glu Phe Glu
1 5 10 15

Pro ( 2 ) INFORMATION FOR SEQ ID NO:21:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:21:

Glu Gln Glu Asp Ala Ser Ala Thr Asp Arg Gly Leu Gly Pro Ser Leu
1 5 10 15

Thr ( 2 ) INFORMATION FOR SEQ ID NO:22:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:22:

Pro Gly Pro Tyr Leu Ala Pro Gly Leu Leu Gly Ser Asn Ile His Gln
1 5 10 15

Gln ( 2 ) INFORMATION FOR SEQ ID NO:23:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:23:

Arg Ala Ala Thr Asn Ser His His Gly Gly Ala Gly Ala Met Glu Thr
1 5 10 15

Arg Ser ( 2 ) INFORMATION FOR SEQ ID NO:24:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:24:

His Ser Ser Tyr Pro Ala Gly Thr Glu Glu Asp Glu Gly
1 5 10

( 2 ) INFORMATION FOR SEQ ID NO:25:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:25:

Glu Glu Leu Ser Pro Phe Arg Gly Arg Ser Arg Ser Ala Pro Pro Asn
1 5 10 15

( 2 ) INFORMATION FOR SEQ ID NO:26:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:26:

Trp Ala Ala Gln Arg Tyr Gly Arg Glu Leu Arg Arg Met Ser Asp Glu
1 5 10 15

( 2 ) INFORMATION FOR SEQ ID NO:27:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:27:

Ser Phe Lys Gly Leu Pro Arg Pro Lys Ser Ala Gly Thr Ala Thr Gln
1 5 10 15

Met ( 2 ) INFORMATION FOR SEQ ID NO:28:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:28:

Ser Ala Gly Trp Thr Arg Ile Ile Gln Ser Trp Trp Asp Arg Asn Leu
1 5 10 15

( 2 ) INFORMATION FOR SEQ ID NO:29:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:29:

ATAAAGCACG TTTCTCGCGA CCTC 24

( 2 ) INFORMATION FOR SEQ ID NO:30:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:30:

GGCACGAGCG GACCCCGCCC CCTAG 25

( 2 ) INFORMATION FOR SEQ ID NO:31:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:31:

GGGAACCCCA AAGCAGCCCT CGCTG 25

( 2 ) INFORMATION FOR SEQ ID NO:32:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:32:

CACACGCCCT AGGCTTGAGG AAGTCC 26

( 2 ) INFORMATION FOR SEQ ID NO:33:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:33:

CGGAATCCGG AGCCTGGGGA GCG 23

( 2 ) INFORMATION FOR SEQ ID NO:34:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:34:

AGGAAGGCGG TGGAGACCAG CAGCCCAG 28

( 2 ) INFORMATION FOR SEQ ID NO:35:

( i ) SEQUENCE CHARACTERISTICS:
( A ) LENGTH: 29 base pairs

-continued ( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:35:

AGTATGTTCC AGATCCCAGA GTTTGAGCC 29

( 2 ) INFORMATION FOR SEQ ID NO:36:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:36:

AGTGAGCAGG AAGACGCTAG TGCTACAGAT 30

( 2 ) INFORMATION FOR SEQ ID NO:37:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:37:

GCCTGGGCCC TAGCCTCACT GAGGAC 26

( 2 ) INFORMATION FOR SEQ ID NO:38:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:38:

CAGCCAGGTC CCTACCTGGC CCCAGGTCTC 30

( 2 ) INFORMATION FOR SEQ ID NO:39:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:39:

GCAACATTCA TCAGCAGGGA CGGGCAGCCA 30

( 2 ) INFORMATION FOR SEQ ID NO:40:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (oligo)

-continued ( x i ) SEQUENCE DESCRIPTION: SEQ ID NO:40:

CAACAGTCAT CATGGAGGCG CAGGGGCTAT G 31

( 2 ) INFORMATION FOR SEQ ID NO:41:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:41:

GACTCGGAGT CGCCACAGTT CGTACCCAG 29

( 2 ) INFORMATION FOR SEQ ID NO:42:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:42:

CGGGGACCGA GGAGGATGAA GGGATGGAGG A 31

( 2 ) INFORMATION FOR SEQ ID NO:43:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:43:

AGCTTAGCCC TTTTCGAGGA CGCTCGCGT 29

( 2 ) INFORMATION FOR SEQ ID NO:44:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:44:

GTTCGGCTCC CCCCAATCTC TGGGCAGCGC AGCG 34

( 2 ) INFORMATION FOR SEQ ID NO:45:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:45:

ACGGCCGTGA GCTCCGAAGG ATGAGCGATG 30

( 2 ) INFORMATION FOR SEQ ID NO:46:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:46:

GTTTGAGGGT TCCTTCAAGG GACTTCCTC 29

( 2 ) INFORMATION FOR SEQ ID NO:47:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:47:

CAAAGAGCGC AGGCACTGCA ACACAGATG 29

( 2 ) INFORMATION FOR SEQ ID NO:48:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:48:

AGCGCCGGCT GGACGCGCAT TATCCAG 27

( 2 ) INFORMATION FOR SEQ ID NO:49:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:49:

GCATTATCCA GTCCTGGTGG GATCGAAACT TG 32

( 2 ) INFORMATION FOR SEQ ID NO:50:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:50:

GGATCGAAAC TTGGGCAAAG GAGGCTCCAC CCCCTCCCA 39

( 2 ) INFORMATION FOR SEQ ID NO:51:

( i ) SEQUENCE CHARACTERISTICS:
( A ) LENGTH: 239 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:51:

Met Ala His Ala Gly Arg Thr Gly Tyr Asp Asn Arg Glu Ile Val Met
1 5 10 15

Lys Tyr Ile His Tyr Lys Leu Ser Gln Arg Gly Tyr Glu Trp Asp Ala
20 25 30

Gly Asp Val Gly Ala Ala Pro Pro Gly Ala Ala Pro Ala Pro Gly Ile
35 40 45

Phe Ser Ser Gln Pro Gly His Thr Pro His Pro Ala Ala Ser Arg Asp
50 55 60

Pro Val Ala Arg Thr Ser Pro Leu Gln Thr Pro Ala Ala Pro Gly Ala
65 70 75 80

Ala Ala Gly Pro Ala Leu Ser Pro Val Pro Pro Val Val His Leu Ala
85 90 95

Leu Arg Gln Ala Gly Asp Asp Phe Ser Arg Arg Tyr Arg Gly Asp Phe
100 105 110

Ala Glu Met Ser Ser Gln Leu His Leu Thr Pro Phe Thr Ala Arg Gly
115 120 125

Arg Phe Ala Thr Val Val Glu Glu Leu Phe Arg Asp Gly Val Asn Trp
130 135 140

Gly Arg Ile Val Ala Phe Phe Glu Phe Gly Gly Val Met Cys Val Glu
145 150 155 160

Ser Val Asn Arg Glu Met Ser Pro Leu Val Asp Asn Ile Ala Leu Trp
165 170 175

Met Thr Glu Tyr Leu Asn Arg His Leu His Thr Trp Ile Gln Asp Asn
180 185 190

Gly Gly Trp Asp Ala Phe Val Glu Leu Tyr Gly Pro Ser Met Arg Pro
195 200 205

Leu Phe Asp Phe Ser Trp Leu Ser Leu Lys Thr Leu Leu Ser Leu Ala
210 215 220

Leu Val Gly Ala Cys Ile Thr Leu Gly Ala Tyr Leu Ser His Lys
225 230 235

( 2 ) INFORMATION FOR SEQ ID NO:52:

( i ) SEQUENCE CHARACTERISTICS:
( A ) LENGTH: 205 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:52:

Met Ala His Ala Gly Arg Thr Gly Tyr Asp Asn Arg Glu Ile Val Met
1 5 10 15

Lys Tyr Ile His Tyr Lys Leu Ser Gln Arg Gly Tyr Glu Trp Asp Ala
20 25 30

Gly Asp Val Gly Ala Ala Pro Pro Gly Ala Ala Pro Ala Pro Gly Ile
35 40 45

Phe Ser Ser Gln Pro Gly His Thr Pro His Pro Ala Ala Ser Arg Asp
50 55 60

Pro Val Ala Arg Thr Ser Pro Leu Gln Thr Pro Ala Ala Pro Gly Ala
65 70 75 80

-continued

| | | | | | | | | | | | | | | | |
|---|---|---|---|---|---|---|---|---|---|---|---|---|---|---|---|
| Ala | Ala | Gly | Pro | Ala | Leu | Ser | Pro | Val | Pro | Pro | Val | Val | His | Leu | Ala |
| | | | | 85 | | | | | 90 | | | | | 95 | |
| Leu | Arg | Gln | Ala | Gly | Asp | Asp | Phe | Ser | Arg | Arg | Tyr | Arg | Gly | Asp | Phe |
| | | | 100 | | | | | 105 | | | | | 110 | | |
| Ala | Glu | Met | Ser | Ser | Gln | Leu | His | Leu | Thr | Pro | Phe | Thr | Ala | Arg | Gly |
| | | 115 | | | | | 120 | | | | | 125 | | | |
| Arg | Phe | Ala | Thr | Val | Val | Glu | Glu | Leu | Phe | Arg | Asp | Gly | Val | Asn | Trp |
| | 130 | | | | | 135 | | | | | 140 | | | | |
| Gly | Arg | Ile | Val | Ala | Phe | Phe | Glu | Phe | Gly | Gly | Val | Met | Cys | Val | Glu |
| 145 | | | | | 150 | | | | | 155 | | | | | 160 |
| Ser | Val | Asn | Arg | Glu | Met | Ser | Pro | Leu | Val | Asp | Asn | Ile | Ala | Leu | Trp |
| | | | | 165 | | | | | 170 | | | | | 175 | |
| Met | Thr | Glu | Tyr | Leu | Asn | Arg | His | Leu | His | Thr | Trp | Ile | Gln | Asp | Asn |
| | | | 180 | | | | | 185 | | | | | 190 | | |
| Gly | Gly | Trp | Val | Gly | Ala | Ser | Gly | Asp | Val | Ser | Leu | Gly | | | |
| | | 195 | | | | | 200 | | | | | 205 | | | |

( 2 ) INFORMATION FOR SEQ ID NO:53:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:53:

TCGGAGTCGC CACAGTTCGT A 21

( 2 ) INFORMATION FOR SEQ ID NO:54:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:54:

GACTCAAGCT GTACGTCAGC T 21

( 2 ) INFORMATION FOR SEQ ID NO:55:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:55:

ATGACTTTGA ACTGCGGTAC C 21

( 2 ) INFORMATION FOR SEQ ID NO:56:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:56:

AAGCGCTCCT GGCCTTTCCG G 21

( 2 ) INFORMATION FOR SEQ ID NO:57:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:57:

ATGGATGACG ATATCGCT 18

( 2 ) INFORMATION FOR SEQ ID NO:58:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (oligo)

( x i ) SEQUENCE DESCRIPTION: SEQ ID NO:58:

ATGAGGTAGT CTGTCATGGT 20

( 2 ) INFORMATION FOR SEQ ID NO:59:

( i ) SEQUENCE CHARACTERISTICS:
( A ) LENGTH: 233 amino acids
( B ) TYPE: amino acid
( C ) STRANDEDNESS: single
( D ) TOPOLOGY: unknown ( i i ) MOLECULE TYPE: peptide ( x i ) SEQUENCE DESCRIPTION: SEQ ID NO:59:

| | | | | | | | | | | | | | | | |
|---|---|---|---|---|---|---|---|---|---|---|---|---|---|---|---|
| Met | Ser | Gln | Ser | Asn | Arg | Glu | Leu | Val | Val | Asp | Phe | Leu | Ser | Tyr | Lys |
| 1 | | | | 5 | | | | | 10 | | | | | 15 | |
| Leu | Ser | Gln | Lys | Gly | Tyr | Ser | Trp | Ser | Gln | Phe | Ser | Asp | Val | Glu | Glu |
| | | | 20 | | | | | 25 | | | | | 30 | | |
| Asn | Arg | Thr | Glu | Ala | Pro | Glu | Gly | Thr | Glu | Ser | Glu | Met | Glu | Thr | Pro |
| | | 35 | | | | | 40 | | | | | 45 | | | |
| Ser | Ala | Ile | Asn | Gly | Asn | Pro | Ser | Trp | His | Leu | Ala | Asp | Ser | Pro | Ala |
| | 50 | | | | | 55 | | | | | 60 | | | | |
| Val | Asn | Gly | Ala | Thr | Gly | His | Ser | Ser | Ser | Leu | Asp | Ala | Arg | Glu | Val |
| 65 | | | | | 70 | | | | | 75 | | | | | 80 |
| Ile | Pro | Met | Ala | Ala | Val | Lys | Gln | Ala | Leu | Arg | Glu | Ala | Gly | Asp | Glu |
| | | | | 85 | | | | | 90 | | | | | 95 | |
| Phe | Glu | Leu | Arg | Tyr | Arg | Arg | Ala | Phe | Ser | Asp | Leu | Thr | Ser | Gln | Leu |
| | | | 100 | | | | | 105 | | | | | 110 | | |
| His | Ile | Thr | Pro | Gly | Thr | Ala | Tyr | Gln | Ser | Phe | Glu | Gln | Val | Val | Asn |
| | | 115 | | | | | 120 | | | | | 125 | | | |
| Glu | Leu | Phe | Arg | Asp | Gly | Val | Asn | Trp | Gly | Arg | Ile | Val | Ala | Phe | Phe |
| | 130 | | | | | 135 | | | | | 140 | | | | |
| Ser | Phe | Gly | Gly | Ala | Leu | Cys | Val | Glu | Ser | Val | Asp | Lys | Glu | Met | Gln |
| 145 | | | | | 150 | | | | | 155 | | | | | 160 |
| Val | Leu | Val | Ser | Arg | Ile | Ala | Ala | Trp | Met | Ala | Thr | Tyr | Leu | Asn | Asp |
| | | | | 165 | | | | | 170 | | | | | 175 | |

-continued

| | | | | | | | | | | | | | | | |
|---|---|---|---|---|---|---|---|---|---|---|---|---|---|---|---|
| His | Leu | Glu | Pro<br>180 | Trp | Ile | Gln | Glu | Asn<br>185 | Gly | Gly | Trp | Asp | Thr<br>190 | Phe | Val |
| Glu | Leu | Tyr<br>195 | Gly | Asn | Asn | Ala | Ala<br>200 | Ala | Glu | Ser | Arg | Lys<br>205 | Gly | Gln | Glu |
| Arg | Phe<br>210 | Asn | Arg | Trp | Phe | Leu<br>215 | Thr | Gly | Met | Thr | Val<br>220 | Ala | Gly | Val | Val |
| Leu<br>225 | Leu | Gly | Ser | Leu | Phe<br>230 | Ser | Arg | Lys | | | | | | | |

I claim:

1. A polynucleotide, free of homologous chromosomal DNA, comprising a sequence encoding a mammalian Bad polypeptide, wherein said polypeptide a) lacks the carboxyl terminal signal-anchor sequence characteristic of the membrane bound members of the bcl-2 family, b) has a BH-1 and BH-2 domain, and c) selectively heterodimerizes with bcl-2, and bcl-$x_L$.

2. An isolated polynucleotide of claim 1, wherein said polynucleotide encodes Bad polypeptide of SEQ ID NO:2.

3. An isolated polynucleotide of claim 1, wherein said polynucleotide comprises a nucleotide sequence selected from the group of sequences consisting of:

5'-GGGAACCCCAAAGCAGCCCTCGCTG-3' (SEQ ID NO:31);

5'-CACACGCCCTAGGCTTGAGGAAGTCC-3' (SEQ ID NO:32);

5'-CGGAATCCGGAGCCTGGGGAGCG-3' (SEQ ID NO:33);

5'-AGGAAGGCGGTGGAGACCAGCAGCCCAG-3' (SEQ ID NO:34);

5'-AGTATGTTCCAGATCCCAGAGTTTGAGCC-3' (SEQ ID NO:35);

5'-AGTGAGCAGGAAGACGCTAGTGCTACAGAT-3' (SEQ ID NO:36);

5'-GCCTGGGCCCTAGCCTCACTGAGGAC-3' (SEQ ID NO:37);

5'-CAGCCAGGTCCCTACCTGGCCCCAGGTCTC-3' (SEQ ID NO:38);

5'-GCAACATTCATCAGCAGGGACGGGCAGCCA-3' (SEQ ID NO:39);

5'-CAACAGTCATCATGGAGGCGCAGGGGCTATG-3' (SEQ ID NO:40);

5'-GACTCGGAGTCGCCACAGTTCGTACCCAG-3' (SEQ ID NO:41);

5'-CGGGGACCGAGGAGGATGAAGGGATGGAGGA-3' (SEQ ID NO:42);

5'-AGCTTAGCCCTTTTCGAGGACGCTCGCGT-3' (SEQ ID NO:43);

5'-GTTCGGCTC-CCCCCAATCTCTGGGCAGCGCAGCG-3' (SEQ ID NO:44);

5'-ACGGCCGTGAGCTCCGAAGGATGAGCGATG-3' (SEQ ID NO:45);

5'-GTTTGAGGGTTCCTTCAAGGGACTTCCTC-3' (SEQ ID NO:46);

5'-CAAAGAGCGCAGGCACTGCAACACAGATG-3' (SEQ ID NO:47);

5'-AGCGCCGGCTGGACGCGCATTATCCAG-3' (SEQ ID NO:48);

5'-GCATTATCCAGTCCTGGTGGGATCGAAACTTG-3' (SEQ ID NO:49); and

5'-GGATCGAAACTTGGGCAAAGGAGGCTC-CACCCCCTCCCA-3' (SEQ ID NO:50).

4. An isolated polynucleotide of claim 3, wherein said polynucleotide comprises at least two nucleotide sequence selected from the group of sequences consisting of:

5'-GGGAACCCCAAAGCAGCCCTCGCTG-3' (SEQ ID NO:31);

5'-CACACGCCCTAGGCTTGAGGAAGTCC-3' (SEQ ID NO:32);

5'-CGGAATCCGGAGCCTGGGGAGCG-3' (SEQ ID NO:33);

5'-AGGAAGGCGGTGGAGACCAGCAGCCCAG-3' (SEQ ID NO:34);

5'-AGTATGTTCCAGATCCCAGAGTTTGAGCC-3' (SEQ ID NO:35);

5'-AGTGAGCAGGAAGACGCTAGTGCTACAGAT-3' (SEQ ID NO:36);

5'-GCCTGGGCCCTAGCCTCACTGAGGAC-3' (SEQ ID NO:37);

5'-CAGCCAGGTCCCTACCTGGCCCCAGGTCTC-3' (SEQ ID NO:38);

5'-GCAACATTCATCAGCAGGGACGGGCAGCCA-3' (SEQ ID NO:39);

5'-CAACAGTCATCATGGAGGCGCAGGGGCTATG-3' (SEQ ID NO:40);

5'-GACTCGGAGTCGCCACAGTTCGTACCCAG-3' (SEQ ID NO:41);

5'-CGGGGACCGAGGAGGATGAAGGGATGGAGGA-3' (SEQ ID NO:42);

5'-AGCTTAGCCCTTTTCGAGGACGCTCGCGT-3' (SEQ ID NO:43);

5'-GTTCGGCTC-CCCCCAATCTCTGGGCAGCGCAGCG-3' (SEQ ID NO:44);

5'-ACGGCCGTGAGCTCCGAAGGATGAGCGATG-3' (SEQ ID NO:45);

5'-GTTTGAGGGTTCCTTCAAGGGACTTCCTC-3' (SEQ ID NO:46);

5'-CAAAGAGCGCAGGCACTGCAACACAGATG-3' (SEQ ID NO:47);

5'-AGCGCCGGCTGGACGCGCATTATCCAG-3' (SEQ ID NO:48);

5'-GCATTATCCAGTCCTGGTGGGATCGAAACTTG-3' (SEQ ID NO:49); and

5'-GGATCGAAACTTGGGCAAAGGAGGCTC-CACCCCCTCCCA-3' (SEQ ID NO:50).

5. An isolated polynucleotide of claim 3, wherein said polynucleotide comprises the sequence:

5'-ATGGGAACCCCAAAGCAGCCCTCGCTG-GCTCCTGCACACGCCCTAGGCTTGAGGAAGTCC GATCCCGGAATCCGGAGCCTGGGGAGC-GACGCGGGAGGAAGGCGGTGGAGACCAG-CAGCCCAG AGTATGTTCCAGATCCCA-GAGTTTGAGCCGAGTGAGCAGGAAGACGCTA GTGCTACAGATAGG GGCCTGGGCCCTAGCCT-CACTGAGGACCAGCCAGGTCCCTACCTG-

GCCCCAGGTCTCCTGGGG AGCAACATTCATCAG-CAGGGACGGGCAGCCACCAACAGTCATCATGG AGGC GCAGGGGCTATG GAGACTCGGAGTCGC-CACAGTTCGTACCCAGCGGGGACCGAG-GAGGATGAAGGGATGGAGGAG GAGCTTAGC-CCTTTTCGAGGACGCTCGCGTTCGGCTCCCCCC AATCTCTGGG CAGCGCAGCGC TACGGCCGT-GAGCTCCGAAGGATGAGCGAT-GAGTTTGAGGGTTCCTTCAAGGGACTTCCTCGC CCAAAGAGCGCAGGCACTGCAACACA-GATGCGACAAAGCGCCGG CTGGACG CGCAT-TATCCAG TCCTGGTGGGATCGAAACT-TGGGCAAAGGAGGCTCCACCCCCTCCCAGTGA-3' (SEQ ID NO:3).

6. A polynucleotide of claim 1, wherein said polynucleotide encodes a fusion protein.

7. A Bad polynucleolide encoding a Bad polypeptide of comprising SEQ ID NO:10 and SEQ ID NO:17.

8. An isolated host cell comprising a recombinant polynucleotide.

9. A composition comprising:

a) a fusion gene comprising the polynucleotide of claim 10 fused in frame with a polynucleotide encoding an activator domain of a transcriptional activator protein, b) a fusion gene comprising a sequence encoding bcl-2 or bcl-$x_L$ fused in frame to a polynucleotide encoding a DNA-binding domain of said transcriptional activator protein of a) and c) a reporter gene functionally linked to a transcriptional regulatory element whose transcriptional activity is dependent upon the amount of a heterodimer of polypeptides encoded by the fusion genes of a) and b).

* * * * *

UNITED STATES PATENT AND TRADEMARK OFFICE

CERTIFICATE OF CORRECTION

PATENT NO. : 5,622,852

DATED : April 22, 1997

INVENTOR(S) : Stanley J. Korsmeyer

It is certified that error appears in the above-indentified patent and that said Letters Patent is hereby corrected as shown below:

Column 1, line 9, delete "49712-05" and substitute therefor --CA 50239--.

Column 5, line 33, delete "neath" and substitute therefor --death--.

Column 50, line 33, delete "neath" and substitute therefor --death--.

Column 92, line 1, delete "of".

Column 92, line 4, after the word nucleotide add --of claim 1--.

Column 92, line 7, delete "10" and substitute therefor --1--.

Signed and Sealed this

Twenty-fifth Day of August, 1998

Attest:

BRUCE LEHMAN

Attesting Officer

Commissioner of Patents and Trademarks